(12) United States Patent
Grillari et al.

(10) Patent No.: US 11,814,680 B2
(45) Date of Patent: Nov. 14, 2023

(54) BIOMARKERS FOR DETECTING SENESCENT CELLS

(71) Applicants: Universität für Bodenkultur Wien, Vienna (AT); Buck Institute for Research on Aging, Novato, CA (US)

(72) Inventors: Johannes Grillari, Bisamberg (AT); Matthias Hackl, Bisamberg (AT); Judith Campisi, Berkeley, CA (US); Abhijit Kale, Novato, CA (US)

(73) Assignees: BUCK INSTITUTE FOR RESEARCH ON AGING, Novato, CA (US); UNIVERSITÄT FÜR BODENKULTUR WIEN, Vienna (AT)

( * ) Notice: Subject to any disclaimer, the term of this patent is extended or adjusted under 35 U.S.C. 154(b) by 301 days.

(21) Appl. No.: 16/625,632

(22) PCT Filed: Jun. 26, 2018

(86) PCT No.: PCT/EP2018/067063
§ 371 (c)(1),
(2) Date: Dec. 20, 2019

(87) PCT Pub. No.: WO2019/002265
PCT Pub. Date: Jan. 3, 2019

(65) Prior Publication Data
US 2022/0228213 A1    Jul. 21, 2022

(30) Foreign Application Priority Data
Jun. 26, 2017 (EP) .................................... 17177840

(51) Int. Cl.
*C12Q 1/6883* (2018.01)
*C12Q 1/6851* (2018.01)

(52) U.S. Cl.
CPC ......... *C12Q 1/6883* (2013.01); *C12Q 1/6851* (2013.01); *C12Q 2600/178* (2013.01)

(58) Field of Classification Search
None
See application file for complete search history.

(56) References Cited

U.S. PATENT DOCUMENTS

| | | |
|---|---|---|
| 5,912,148 A | 6/1999 | Eggerding |
| 6,130,073 A | 10/2000 | Eggerding |
| 6,258,568 B1 | 7/2001 | Nyren |
| 6,818,395 B1 | 11/2004 | Quake et al. |
| 6,833,246 B2 | 12/2004 | Balasubramanian |
| 6,911,345 B2 | 6/2005 | Quake et al. |
| 6,969,488 B2 | 11/2005 | Bridgham et al. |
| 7,115,400 B1 | 10/2006 | Adessi et al. |
| 7,169,560 B2 | 1/2007 | Lapidus et al. |
| 7,170,050 B2 | 1/2007 | Turner et al. |
| 7,282,337 B1 | 10/2007 | Harris |
| 7,302,146 B2 | 11/2007 | Turner et al. |
| 7,313,308 B2 | 12/2007 | Turner et al. |
| 7,329,492 B2 | 2/2008 | Hardin et al. |
| 7,476,503 B2 | 1/2009 | Turner et al. |
| 7,482,120 B2 | 1/2009 | Buzby |
| 7,501,245 B2 | 3/2009 | Quake et al. |
| 2009/0163430 A1 | 6/2009 | Johnson et al. |
| 2013/0274147 A1 | 10/2013 | Eshoo et al. |
| 2014/0038831 A1 | 2/2014 | Suter et al. |
| 2014/0342370 A1 | 11/2014 | Wang |
| 2017/0022571 A1* | 1/2017 | Malafa ................ C12Q 1/6886 |
| 2017/0042129 A1 | 2/2017 | Campisi et al. |

FOREIGN PATENT DOCUMENTS

| | | |
|---|---|---|
| JP | 2016-144439 | 8/2016 |
| WO | 2011/014476 A1 | 2/2011 |
| WO | 2012/010905 A2 | 1/2012 |
| WO | 2012/105826 A1 | 8/2012 |

OTHER PUBLICATIONS

Schlosser et al PLoS ONE. 2015. 10(5): e0127443 and Table S1, total of 23 pages (Year: 2015).*
Zellars, K.N. ((2017) "Advancing Automated Methods for Microrna Profiling" Doctoral Dissertation. 45 pages, available via URL: <scholarcommons.sc.edu/etd/4421> (Year: 2017).*
Abouheif et al., "Silencing microRNA-34a inhibits chondrocyte apoptosis in a rat osteoarthritis model in vitro", Rheumatology, 2010, vol. 49, No. 11, pp. 2054-2060.
Adams et al., "The Tumor-Suppressive and Potential Therapeutic Functions of miR-34a in Epithelial Carcinomas", Expert Opin. Ther. Targets, 2016, vol. 20, No. 6, pp. 737-753.
Anonymous, "TaqMan Array Human MicroRNA Cards", Applied Biosystems, 2010, pp. 1-2, XP002672200.
Baar et al., "Targeted Apoptosis of Senescent Cells Restores Tissue Homeostasis in Response to Chemotoxicity and Aging", Cell, 2017, vol. 169, No. 1, pp. 132-147.
Bai et al., "miR-335 and miR-34a Promote Renal Senescence by Suppressing Mitochondrial Antioxidative Enzymes", J. Am Soc. Nephrol., 2011, vol. 22, No. 7, pp. 1251-1261.
Baker et al., "Clearance of p16lnk4a-positive senescent cells delays ageing-associated disorders", Nature, 2011, vol. 179, No. 7372, pp. 232-236.
Baker et al., "Naturally occurring p16lnk4a-positive cells shorten healthy lifespan". Nature, 2016, vol. 530, No. 7589, pp. 184-189.
Bejhati et al., "What is next generation sequencing?", Arch. Dis. Child Educ. Pract. Ed., 2013, vol. 98, pp. 236-238.
Beyer et al., "Signature of circulating microRNAs in osteoarthritis", Ann. Rheum. Dis., 2015, vol. 74, No. 3, p. e18.
Bhatnagar et al., "Increased microRNA-34c abundance in Alzheimer's disease circulating blood plasma", Frontiers in Molecular Neuroscience, 2014, vol. 7, Article 2, pp. 1-11.
Blondal et al., "Assessing sample and miRNI profile quality in serum and plasma or other biofluids", Methods, 2013, vol. 59, No. 1, pp. 1-6.

(Continued)

*Primary Examiner* — Carla J Myers
(74) *Attorney, Agent, or Firm* — LOZA & LOZA, LLP; Michael F. Fedrick

(57) ABSTRACT

The present invention provides a method of detecting senescent cells or diagnosing cellular senescence in a subject wherein the level of one or more selected miRNAs is quantified in a sample from said subject.

Figure 1:
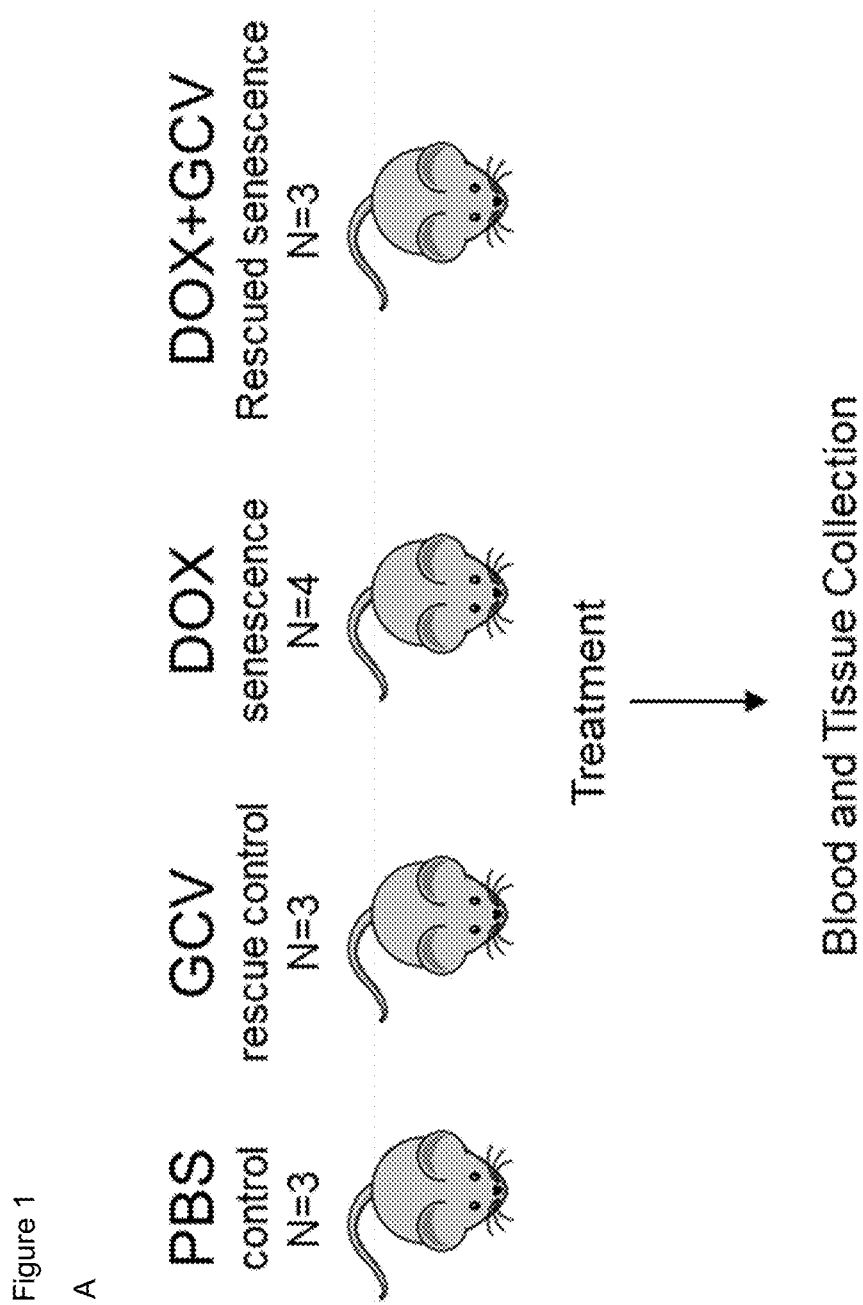
Figure 1B:
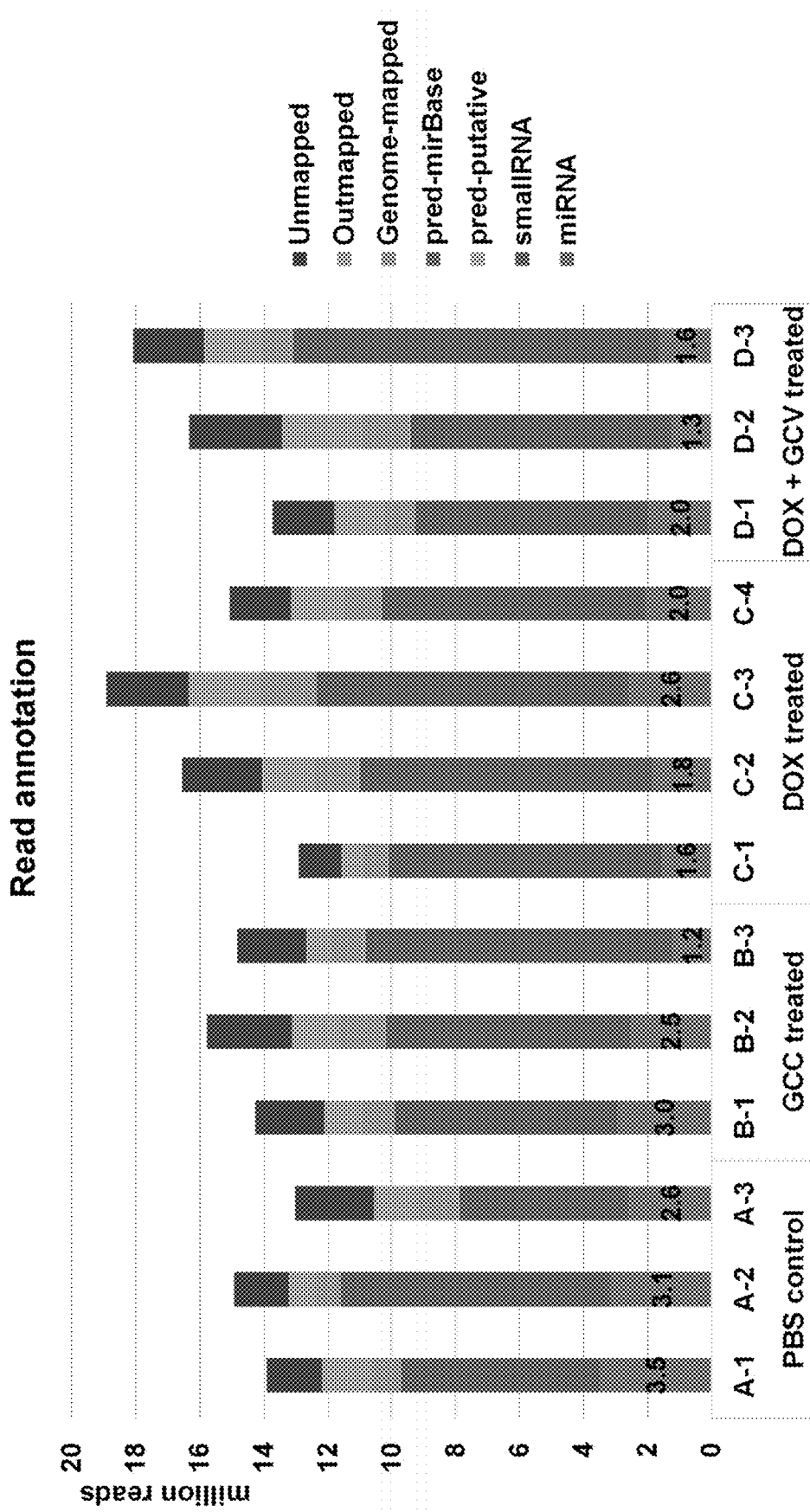

12 Claims, 9 Drawing Sheets
Specification includes a Sequence Listing.

(56) References Cited

OTHER PUBLICATIONS

Boeckel et al., Heparin Selectively Affects the Quantification of MicroRNAs in Human Blood Samples, Clinical Chemistry, 2013, vol. 59, No. 7, pp. 1125-1127.

Bonafe et al., "Circulating microRNAs in aging", Oncotarget, 2015, vol. 6, No. 3, pp. 1340-1341.

Cermelli et al., "Circulating MicroRNAs in Patients with Chronic Hepatitis C and Non-Alcoholic Fatty Liver Disease", PLoS One, 2011, vol. 6, e23937.

Chang et al., "Clearance of senescent cells by ABT263 rejuvenates aged hematopoietic stem cells in mice", Nat. Med., 2016, vol. 22, No. 1, pp. 78-83.

Chen et al., "Characterization of microRNAs in serum: a novel class of biomarkers for diagnosis of cancer and other diseases", Cell Research, 2008, vol. 18, No. 10, pp. 997-1006.

Cheng et al., "Plasma Processing Conditions Substantially Influence Circulating microRNA Biomarker Levels", PLoS One, 2013, vol. 8, No. 6, e64795.

Christoffersen et al., "p53-independent upregulation of miR-34a during oncogene-induced senescence represses MYC", Cell Death Differ, 2010, vol. 17, No. 2, pp. 236-245.

Corcoran eta l., "miR-34a is an Intracellular and Exosomal Predictive Biomarker for Response to Docetaxel with Clinical Relevance to Prostate Cancer Progression", Prostate, 2014, vol. 74, pp. 1320-1334.

De Gonzalo-Calvo et al., "Circulating inflammatory miRNA signature in response to different doses of aerobic exercise", J. Appl. Physiol., 2015, vol. 119, pp. 124-134.

Dellago et al., "High levels of oncomiR-21 contribute to the senescence-induced growth arrest in normal human cells and its knock-down increases the replicative lifespan", Aging Cell, 2013, vol. 12, No. 3 p. 446-458.

Demaria et al., "An Essential Role for Senescent Cells in Optimal Wound Healing through Secretion of PDGF-AA", Developmental Cell, 2014, vol. 31, No. 6, pp. 722-733.

Fan et al., "MicroRNA-34a Promotes Cardiomyocyte Apoptosis Post Myocardial Infarction Through Down-regulating Aldehyde Dehydrogenase 2", Curr. Pharm. Des., 2013, vol. 19, No. 27, pp. 4865-4873.

Franchina et al., "Circulating miR-22, miR-24 and miR-34a as Novel Predictive Biomarkers to Pemetrexed-Based Chemotherapy in Advanced Non-Small Cell Lung Cancer", J. Cell. Physiol, 2014, vol. 229, No. 1, pp. 97-99.

Fu et al., "MicroRNA-34a and Impaired FGF19/21 Signaling in Obesity", Vitam. Horm., 2016, vol. 101, pp. 175-196.

Garcia et al., "Anticoagulants Interfere with PCR Used to Diagnose Invasive Aspergillosis", J. Clin. Mircrobiol., 2002, vol. 40, No. 4, pp. 1567-1568.

Gombar et al., "Comprehensive microRNA profiling in B-cells of human centenarians by massively parallel sequencing", BMC Genomics, 2012, 13:353 (12 pages).

Grillari et al., "Novel modulators of senescence, aging, and longevity: Small non-coding RNAs enter the stage", Exp. Gerontol., 2010, vol. 45, No. 4, pp. 302-311.

Gustafson et al., "Frailty and constellations of factors in aging HIV-infected and uninfected women—the women's ingeragency HVI study", J. frailty aging, 2016, vol. 5, No. 1, pp. 43-48.

Hackl et al., "miR-17, miR-19b, miR-20a, and miR-106a are down-regulated in human aging", Aging Cell, 2010, vol. 9, No. 2, pp. 291-296.

Hackl et al., "Circulating microRNAs as novel biomarkers for bone diseases—Complex signatures for multifactorial diseases?", Mol. Cell. Endocrinol., 2016, vol. 432, pp. 83-95.

Han et al., "MiR-34a, miR-21 and miR-23a as potential biomarkers for coronary artery disease: a pilot microarray study and confirmation in a 32 patient cohort", Exp. Mol. Med., 2015, vol. 47, e138.

He et al., "The Guardian's Little Helper: MicroRNAs in the p53 Tumor Suppressor Network", Cancer Res., 2007, vol. 37, No. 23, pp. 11099-11101.

Head et al., "Library construction for next-generation sequencing: Overviews and challenges", Biotechniques, 2015, vol. 56, No. 2, pp. 61-77.

Hooten et al., "Age-related changes in microRNA levels in serum", Aging, 2013, vol. 5, No. 10, pp. 725-740.

Ito et al., "MicroRNA-34a regulation of endothelial senescence", Biochem. Biophays. Res. Commun., 2010, vol. 398, No. 4, pp. 735-740.

Kim et al., "Plasma Components Affect Accuracy of Circulating Cancer-Related MicroRNA Quantitation", J. Mol. Diagn., 2012, Epub: 2011, vol. 14, No. 1, pp. 71-80.

Kong et al., "Significance of serum microRNAs in pre-diabetes and newly diagnosed type 2 diabetes: a clinical study", Acta Diabetol., 2011, vol. 48, No. 1, pp. 61-69.

Krzeszinskia et al., "miR-34a Blocks Osteoporosis and Bone Metastasis by Inhibiting Osteoclastogenesis and Tgif2", et al., Nature, 2014, vol. 512, No. 7515, pp. 431-435.

Lee et al., "Histone deacetylase regulates high mobility grou A2-targeting microRNAs in human cord blood-derived multipotent stem cell aging", Cellular and Molecular Life Sciences, 2011, vol. 68, No. 2, pp. 325-336.

Lv et al., "Circulating miR-208b and miR-34a Are Associated with Left Ventricular Remodeling after Acute Myocardial Infarction", Int. J. Mol. Sci., 2014, vol. 15, No. 4, pp. 5774-5788.

Maes et al., "Stepwise Up-Regulation of MicroRNA Expression Levels From Replicating to Reversible and Irreversible Growth Arrest States in WI-38 Human Fibroblasts", J. Cell. Physiol., 2009, vol. 221, No. 1, pp. 109-119.

Matjusaitis et al., "Biomarkers to identify and isolate senescent cells", Aging Research Reviews, 2016, vol. 29, pp. 1-12.

Metsalu et al., "ClustVis: a web tool for visualizing clustering of multivariate data using Principal Component Analysis and heatmap", Nucleic Acids Res., 2015, vol. 43, Web Server issue, W566-W570k, doi: 10.1093/nar/gkv468.

Metzker, Michael L., "Sequencing technologies—the next generation", Nat. Rev. Genet., 2010, vol. 11, No. 1, pp. 31-46.

Mitchell et al., "Circulating microRNAs as stable blood-based markers for cancer detection", Proc. Natl. Acad. Sci., 2008, vol. 105, No. 30, pp. 10513-10518.

Munoz-Espin et al., "Cellular senescence: from physiology to pathology", Nat. Rev. Mol. Cell Biol., 2014, vol. 15, No. 7, pp. 482-496.

Pang et al., "Circulating miR-34a levels correlate with age-related hearing loss in mice and humans", Exp. Gerontol., 2016, vol. 76, pp. 58-67.

Piegari et al., "MicroRNA-34a regulates doxorubicin-induced cardiotoxicity in rat", Oncotarget, 2016, vol. 7, No. 38, pp. 62312-62326.

Reynoso et al., "MicroRNAs differentially present in the plasma of HIV elite controllers reduce HIV infection in vitro", Sci. Rep., 2014, 4:5915.

Rippo et al., "MitomiRs in human inflamm-aging: A hypothesis involving miR-181a, miR-34a and miR-146a", Exp. Gerontol., 2014, vol. 56, pp. 154-163.

Salvoza et al., "Association of Circulating Serum miR-34a and miR-122 with Dyslipidemia among Patients with Non-Alcoholic Fatty Liver Disease", PLoS One, 2016, vol. 11, No. 4, e0153497.

Schmittgen et al., "Real-time PCR quantification of precursor and mature microRNA", Methods 2008, vol. 44, No. 1, pp. 31-38.

Schraml et al., "From cellular senescence to age-associated diseases: the miRNA connection", Longev. Healthspan., 2012, 1:10 (15 pages).

Serna et al., "Centenarians, but not octogenarians, up-regulate the expression of microRNAs", Scientific Reports, 2012, 2:961.

Tarasov et al., "Differential Regulation of microRNAs by p53 Revealed by Massively Parallel Sequencing; miR-34a is a p53 Target That Induces Apoptosis and G1-arrest", Cell Cycle, 2007, vol. 6, No. 13, pp. 1586-1593.

Tazawa et al., "Tumor-suppressive miR-34a induces senescence-like growth arrest through modulation of the E2F pathway in human colon cancer cells", Proc Natl. Acad. Sci, 2007, vol. 104, No. 39, pp. 15472-15477.

(56) References Cited

OTHER PUBLICATIONS

Todorova et al., "Circulating miRCA Profiles of Doxorubicin-induced Cardiotoxicity in Breast Cancer Patients", Annals of Clinical and Laboratory Science, 2017, vol. 47, No. 2, pp. 115-119.
Tome-Carneiro et al., "One-Year Supplementation with a Grape Extract Containing Resveratrol Modulates Inflammatory-Related microRNAs and Cytokines Expression in Peripheral Blood Mononuclear Cells of Type 2 Diabetes and Hypertensive Patients with Coronary Artery Disease", Pharmacol. Res., 2013, vol. 72, pp. 69-82.
Turchinovich et al., "CirculatingmiRNAs:cell-cellcommunicationfunction?", Front. Genet., 2013, vol. 4, No. 119, pp. 1-10.
Weilner et al., "Secretion of microvesicular miRNAs in cellular and organismal aging", Experimental Gerontology, 2012, vol. 48, No. 7, pp. 626-633.
Williams et al., "Are microRNAs true sensors of ageing and cellular senescence?", Ageing Research Reviews, 2016, vol. 35, pp. 350-363.
Xue et al., "Small RNA combination therapy for lung cancer", PNAS, 2014, vol. 111, No. 34, pp. E3553-E3561.
Yamada et al., "Associations between circulating microRNAs (miR-21, miR-34a, miR-122 and miR-451) and nonalcoholic fatty liver", Clin. Chim. Acta., 2013, vol. 424, pp. 99-103.
Yamakuchi et al., "miR-34a repression of SIRT1 regulates apoptosis", PNAS, 2008, vol. 105, No. 36, pp. 13421-13426.
Yang et al., "Induction of Cellular Senescence by Doxorubicin Is Associated with Upregulated miR-375 and Induction of Autophagy in K562 Cells", PLOS ONE, 2012, vol. 7, No. 5, pp. e37205.
Zampetaki et al., "Plasma MicroRNA Profiling Reveals Loss of Endothelial MiR-126 and Other MicroRNAs in Type 2 Diabetes", Circ. Res., 2010, vol. 107, No. 6, pp. 810-817.
Zampetaki et al., "Prospective Study on Circulating MicroRNAs and Risk of Myocardial Infarction", J. Am Coll. Cardiol., 2012, vol. 60, No. 4, pp. 290-299.
Zhou et al., "Secreted fibroblast-derived miR-34a induces tubular cell apoptosis in fibrotic kidney", J. Cell Sci., 2014, vol. 127, pp. 4494-4506.
Zhu et al., "The Achilles' heel of senescent cells: from transcriptome to senolytic drugs", Aging Cell, 2015, vol. 14, pp. 644-658.
Zhu et al., "Identification of a novel senolytic agent, navitoclax, targeting the Bcl-2 family of anti-apoptotic factors", Aging Cell, 2016, vol. 15, No. 3, pp. 428-435.
Partial European Search Report for EP 17177840.0 dated Jept. 28, 2017; 15 pages.
Extended European Search Report for EP 17177840.0 dated Jan. 11, 2018; 13 pages.
International Search Report for PCT/EP18/67063 dated Sep. 24, 2018; 9 pages.
Written Opinion of the ISA for PCT/EP18/67063 dated Sep. 24, 2018; 11 pages.
Invitation to Pay Additional Fees for PCT/EP18/67063 dated Jul. 30, 2018; 8 pages.
International Preliminary Report on Patentability for PCT/EP18/67063 dated Dec. 31, 2019; 12 pages.
Office Action in corrresponding Japanese Patent Appln. No. 2020-520725, dated Jun. 22, 2022.
Hatse et al., "Circulating MicroRNAs as Easy-to-Measure Aging Biomarkers in Older Breast Cancer Patients Correlation with Chronological Age but Not with Fitness/Frailty Status," PLOS ONE, vol. 9, Issue 10, e110644 (Oct. 2014).
Urbanelli et al., "Extracellular Vesicles as New Players in Cellular Senescence," Int'l. J. Molecular Sciences, 17:1408; doi:10.3390/ijms17091408 (2016).

* cited by examiner

A

B

A

B

SEQUENCE LISTING

<160> NUMBER OF SEQ ID NOS: 92

<210> SEQ ID NO 1
<211> LENGTH: 22

```
<212> TYPE: RNA
<213> ORGANISM: Homo sapiens
<220> FEATURE:
<223> OTHER INFORMATION: hsa-miR-34a-5p

<400> SEQUENCE: 1
uggcaguguc uuagcugguu gu                                                    22

<210> SEQ ID NO 2
<211> LENGTH: 22
<212> TYPE: RNA
<213> ORGANISM: Homo sapiens
<220> FEATURE:
<223> OTHER INFORMATION: hsa-let-7f-5p

<400> SEQUENCE: 2
ugagguagua gauuguauag uu                                                    22

<210> SEQ ID NO 3
<211> LENGTH: 22
<212> TYPE: RNA
<213> ORGANISM: Homo sapiens
<220> FEATURE:
<223> OTHER INFORMATION: hsa-let-7a-5p

<400> SEQUENCE: 3
ugagguagua gguuguauag uu                                                    22

<210> SEQ ID NO 4
<211> LENGTH: 21
<212> TYPE: RNA
<213> ORGANISM: Homo sapiens
<220> FEATURE:
<223> OTHER INFORMATION: hsa-miR-143-3p

<400> SEQUENCE: 4
ugagaugaag cacguagcu c                                                      21

<210> SEQ ID NO 5
<211> LENGTH: 21
<212> TYPE: RNA
<213> ORGANISM: Homo sapiens
<220> FEATURE:
<223> OTHER INFORMATION: hsa-miR-27a-3p

<400> SEQUENCE: 5
uucacagugg cuaaguuccg c                                                     21

<210> SEQ ID NO 6
<211> LENGTH: 22
<212> TYPE: RNA
<213> ORGANISM: Homo sapiens
<220> FEATURE:
<223> OTHER INFORMATION: hsa-miR-143-5p

<400> SEQUENCE: 6
ggugcagugc ugcaucucug gu                                                    22

<210> SEQ ID NO 7
<211> LENGTH: 22
<212> TYPE: RNA
<213> ORGANISM: Homo sapiens
<220> FEATURE:
<223> OTHER INFORMATION: hsa-miR-144-5p

<400> SEQUENCE: 7
```
ggauaucauc auauacugua ag                                             22

<210> SEQ ID NO 8
<211> LENGTH: 21
<212> TYPE: RNA
<213> ORGANISM: Homo sapiens
<220> FEATURE:
<223> OTHER INFORMATION: mmu-miR-3058-3p

<400> SEQUENCE: 8
uuccugucag ccgugggugc c                                              21

<210> SEQ ID NO 9
<211> LENGTH: 22
<212> TYPE: RNA
<213> ORGANISM: Homo sapiens
<220> FEATURE:
<223> OTHER INFORMATION: hsa-miR-30b-5p

<400> SEQUENCE: 9
uguaaacauc cuacacucag cu                                             22

<210> SEQ ID NO 10
<211> LENGTH: 23
<212> TYPE: RNA
<213> ORGANISM: Homo sapiens
<220> FEATURE:
<223> OTHER INFORMATION: hsa-miR-339-5p

<400> SEQUENCE: 10
ucccuguccu ccaggagcuc acg                                            23

<210> SEQ ID NO 11
<211> LENGTH: 23
<212> TYPE: RNA
<213> ORGANISM: Homo sapiens
<220> FEATURE:
<223> OTHER INFORMATION: hsa-miR-423-3p

<400> SEQUENCE: 11
agcucggucu gaggccccuc agu                                            23

<210> SEQ ID NO 12
<211> LENGTH: 22
<212> TYPE: RNA
<213> ORGANISM: Homo sapiens
<220> FEATURE:
<223> OTHER INFORMATION: mmu-miR-6395

<400> SEQUENCE: 12
cuggcccucu cugcccuguu ua                                             22

<210> SEQ ID NO 13
<211> LENGTH: 21
<212> TYPE: RNA
<213> ORGANISM: Homo sapiens
<220> FEATURE:
<223> OTHER INFORMATION: hsa-miR-652-3p

<400> SEQUENCE: 13
aauggcgcca cuaggguugu g                                              21

<210> SEQ ID NO 14
<211> LENGTH: 23
<212> TYPE: RNA
<213> ORGANISM: Homo sapiens

```
<220> FEATURE:
<223> OTHER INFORMATION: hsa-miR-18b-5p

<400> SEQUENCE: 14
uaaggugcau cuagugcagu uag                                          23

<210> SEQ ID NO 15
<211> LENGTH: 22
<212> TYPE: RNA
<213> ORGANISM: Homo sapiens
<220> FEATURE:
<223> OTHER INFORMATION: hsa-miR-92a-3p

<400> SEQUENCE: 15
uggcaguguc uuagcugguu gu                                           22

<210> SEQ ID NO 16
<211> LENGTH: 22
<212> TYPE: RNA
<213> ORGANISM: Homo sapiens
<220> FEATURE:
<223> OTHER INFORMATION: hsa-miR-10a-3p

<400> SEQUENCE: 16
caaauucgua ucuagggaa ua                                            22

<210> SEQ ID NO 17
<211> LENGTH: 21
<212> TYPE: RNA
<213> ORGANISM: Homo sapiens
<220> FEATURE:
<223> OTHER INFORMATION: hsa-miR-151a-5p

<400> SEQUENCE: 17
ucgaggagcu cacagucuag u                                            21

<210> SEQ ID NO 18
<211> LENGTH: 23
<212> TYPE: RNA
<213> ORGANISM: Homo sapiens
<220> FEATURE:
<223> OTHER INFORMATION: hsa-miR-191-5p

<400> SEQUENCE: 18
caacggaauc ccaaaagcag cug                                          23

<210> SEQ ID NO 19
<211> LENGTH: 22
<212> TYPE: RNA
<213> ORGANISM: Homo sapiens
<220> FEATURE:
<223> OTHER INFORMATION: hsa-miR-223-3p

<400> SEQUENCE: 19
ugucaguuug ucaauacccc ca                                           22

<210> SEQ ID NO 20
<211> LENGTH: 21
<212> TYPE: RNA
<213> ORGANISM: Homo sapiens
<220> FEATURE:
<223> OTHER INFORMATION: hsa-miR-23a-3p

<400> SEQUENCE: 20
aucacauugc cagggauuuc c                                            21
```

```
<210> SEQ ID NO 21
<211> LENGTH: 22
<212> TYPE: RNA
<213> ORGANISM: Homo sapiens
<220> FEATURE:
<223> OTHER INFORMATION: hsa-miR-24-3p

<400> SEQUENCE: 21
uggcucaguu cagcaggaac ag                                                  22

<210> SEQ ID NO 22
<211> LENGTH: 22
<212> TYPE: RNA
<213> ORGANISM: Homo sapiens
<220> FEATURE:
<223> OTHER INFORMATION: hsa-miR-29a-3p

<400> SEQUENCE: 22
uagcaccauc ugaaaucggu ua                                                  22

<210> SEQ ID NO 23
<211> LENGTH: 23
<212> TYPE: RNA
<213> ORGANISM: Homo sapiens
<220> FEATURE:
<223> OTHER INFORMATION: hsa-miR-20b-5p

<400> SEQUENCE: 23
caaagugcuc auagugcagg uag                                                 23

<210> SEQ ID NO 24
<211> LENGTH: 23
<212> TYPE: RNA
<213> ORGANISM: Homo sapiens
<220> FEATURE:
<223> OTHER INFORMATION: hsa-miR-93-5p

<400> SEQUENCE: 24
caaagugcug uucgugcagg uag                                                 23

<210> SEQ ID NO 25
<211> LENGTH: 23
<212> TYPE: RNA
<213> ORGANISM: Homo sapiens
<220> FEATURE:
<223> OTHER INFORMATION: hsa-miR-106a-5p

<400> SEQUENCE: 25
aaaagugcuu acagugcagg uag                                                 23

<210> SEQ ID NO 26
<211> LENGTH: 21
<212> TYPE: RNA
<213> ORGANISM: Homo sapiens
<220> FEATURE:
<223> OTHER INFORMATION: hsa-miR-106b-5p

<400> SEQUENCE: 26
uaaagugcug acagugcaga u                                                   21

<210> SEQ ID NO 27
<211> LENGTH: 23
<212> TYPE: RNA
<213> ORGANISM: Homo sapiens
<220> FEATURE:
<223> OTHER INFORMATION: hsa-miR-18a-5p
```

-continued

```
<400> SEQUENCE: 27
uaaggugcau cuagugcaga uag                                              23

<210> SEQ ID NO 28
<211> LENGTH: 23
<212> TYPE: RNA
<213> ORGANISM: Homo sapiens
<220> FEATURE:
<223> OTHER INFORMATION: hsa-miR-19a

<400> SEQUENCE: 28
ugugcaaauc uaugcaaaac uga                                              23

<210> SEQ ID NO 29
<211> LENGTH: 23
<212> TYPE: RNA
<213> ORGANISM: Homo sapiens
<220> FEATURE:
<223> OTHER INFORMATION: hsa-miR-19b

<400> SEQUENCE: 29
ugugcaaauc caugcaaaac uga                                              23

<210> SEQ ID NO 30
<211> LENGTH: 22
<212> TYPE: RNA
<213> ORGANISM: Homo sapiens
<220> FEATURE:
<223> OTHER INFORMATION: hsa-miR-17-3p

<400> SEQUENCE: 30
acugcaguga aggcacuugu ag                                               22

<210> SEQ ID NO 31
<211> LENGTH: 23
<212> TYPE: RNA
<213> ORGANISM: Homo sapiens
<220> FEATURE:
<223> OTHER INFORMATION: hsa-miR-17-5p

<400> SEQUENCE: 31
caaagugcuu acagugcagg uag                                              23

<210> SEQ ID NO 32
<211> LENGTH: 22
<212> TYPE: RNA
<213> ORGANISM: Homo sapiens
<220> FEATURE:
<223> OTHER INFORMATION: hsa-miR-20a-3p

<400> SEQUENCE: 32
acugcauuau gagcacuuaa ag                                               22

<210> SEQ ID NO 33
<211> LENGTH: 23
<212> TYPE: RNA
<213> ORGANISM: Homo sapiens
<220> FEATURE:
<223> OTHER INFORMATION: hsa-miR-20a-5p

<400> SEQUENCE: 33
uaaagugcuu auagugcagg uag                                              23

<210> SEQ ID NO 34
```

```
<211> LENGTH: 22
<212> TYPE: RNA
<213> ORGANISM: Homo sapiens
<220> FEATURE:
<223> OTHER INFORMATION: hsa-miR-15a-5p

<400> SEQUENCE: 34
uagcagcaca uaaugguuug ug                                          22

<210> SEQ ID NO 35
<211> LENGTH: 22
<212> TYPE: RNA
<213> ORGANISM: Homo sapiens
<220> FEATURE:
<223> OTHER INFORMATION: hsa-miR-15b-3p

<400> SEQUENCE: 35
caggccauau ugugcugccu ca                                          22

<210> SEQ ID NO 36
<211> LENGTH: 22
<212> TYPE: RNA
<213> ORGANISM: Homo sapiens
<220> FEATURE:
<223> OTHER INFORMATION: hsa-miR-16-5p

<400> SEQUENCE: 36
uagcagcacg uaaauauugg cg                                          22

<210> SEQ ID NO 37
<211> LENGTH: 22
<212> TYPE: RNA
<213> ORGANISM: Homo sapiens
<220> FEATURE:
<223> OTHER INFORMATION: hsa-miR-16-1-3p

<400> SEQUENCE: 37
ccaguauuaa cugugcugcu ga                                          22

<210> SEQ ID NO 38
<211> LENGTH: 22
<212> TYPE: RNA
<213> ORGANISM: Homo sapiens
<220> FEATURE:
<223> OTHER INFORMATION: hsa-let-7b-5p

<400> SEQUENCE: 38
ugagguagua gguugugugg uu                                          22

<210> SEQ ID NO 39
<211> LENGTH: 22
<212> TYPE: RNA
<213> ORGANISM: Homo sapiens
<220> FEATURE:
<223> OTHER INFORMATION: hsa-let-7c-5p

<400> SEQUENCE: 39
ugagguagua gguuguaugg uu                                          22

<210> SEQ ID NO 40
<211> LENGTH: 22
<212> TYPE: RNA
<213> ORGANISM: Homo sapiens
<220> FEATURE:
<223> OTHER INFORMATION: hsa-let-7c-5p

<400> SEQUENCE: 40
```

-continued ugagguagua gguuguaugg uu                    22

<210> SEQ ID NO 41
<211> LENGTH: 22
<212> TYPE: RNA
<213> ORGANISM: Homo sapiens
<220> FEATURE:
<223> OTHER INFORMATION: hsa-let-7d-5p

<400> SEQUENCE: 41
agagguagua gguugcauag uu                    22

<210> SEQ ID NO 42
<211> LENGTH: 22
<212> TYPE: RNA
<213> ORGANISM: Homo sapiens
<220> FEATURE:
<223> OTHER INFORMATION: hsa-let-7d-3p

<400> SEQUENCE: 42
cuauacgacc ugcugccuuu cu                    22

<210> SEQ ID NO 43
<211> LENGTH: 22
<212> TYPE: RNA
<213> ORGANISM: Homo sapiens
<220> FEATURE:
<223> OTHER INFORMATION: hsa-let-7f

<400> SEQUENCE: 43
ugagguagua gauuguauag uu                    22

<210> SEQ ID NO 44
<211> LENGTH: 21
<212> TYPE: RNA
<213> ORGANISM: Homo sapiens
<220> FEATURE:
<223> OTHER INFORMATION: hsa-let-7g-3p

<400> SEQUENCE: 44
cuguacaggc cacugccuug c                     21

<210> SEQ ID NO 45
<211> LENGTH: 22
<212> TYPE: RNA
<213> ORGANISM: Homo sapiens
<220> FEATURE:
<223> OTHER INFORMATION: hsa-let-7i-3p

<400> SEQUENCE: 45
cugcgcaagc uacugccuug cu                    22

<210> SEQ ID NO 46
<211> LENGTH: 22
<212> TYPE: RNA
<213> ORGANISM: Homo sapiens
<220> FEATURE:
<223> OTHER INFORMATION: hsa-miR-23a-5p

<400> SEQUENCE: 46
gggguuccug gggaugggau uu                    22

<210> SEQ ID NO 47
<211> LENGTH: 21
<212> TYPE: RNA

```
<213> ORGANISM: Homo sapiens
<220> FEATURE:
<223> OTHER INFORMATION: hsa-miR-23b-3p

<400> SEQUENCE: 47
aucacauugc cagggauuac c                                              21

<210> SEQ ID NO 48
<211> LENGTH: 22
<212> TYPE: RNA
<213> ORGANISM: Homo sapiens
<220> FEATURE:
<223> OTHER INFORMATION: hsa-miR-24-1-5p

<400> SEQUENCE: 48
ugccuacuga gcugauauca gu                                             22

<210> SEQ ID NO 49
<211> LENGTH: 21
<212> TYPE: RNA
<213> ORGANISM: Homo sapiens
<220> FEATURE:
<223> OTHER INFORMATION: hsa-miR-27b-3p

<400> SEQUENCE: 49
uucacagugg cuaaguucug c                                              21

<210> SEQ ID NO 50
<211> LENGTH: 23
<212> TYPE: RNA
<213> ORGANISM: Homo sapiens
<220> FEATURE:
<223> OTHER INFORMATION: hsa-miR-29b-3p

<400> SEQUENCE: 50
uagcaccauu ugaaaucagu guu                                            23

<210> SEQ ID NO 51
<211> LENGTH: 22
<212> TYPE: RNA
<213> ORGANISM: Homo sapiens
<220> FEATURE:
<223> OTHER INFORMATION: hsa-miR-29c-3p

<400> SEQUENCE: 51
uagcaccauu ugaaaucggu ua                                             22

<210> SEQ ID NO 52
<211> LENGTH: 22
<212> TYPE: RNA
<213> ORGANISM: Homo sapiens
<220> FEATURE:
<223> OTHER INFORMATION: hsa-miR-30a-3p

<400> SEQUENCE: 52
cuuucagucg gauguuugca gc                                             22

<210> SEQ ID NO 53
<211> LENGTH: 22
<212> TYPE: RNA
<213> ORGANISM: Homo sapiens
<220> FEATURE:
<223> OTHER INFORMATION: hsa-miR-30a-5p

<400> SEQUENCE: 53
uguaaacauc cucgacugga ag                                             22
```

<210> SEQ ID NO 54
<211> LENGTH: 23
<212> TYPE: RNA
<213> ORGANISM: Homo sapiens
<220> FEATURE:
<223> OTHER INFORMATION: hsa-miR-30c

<400> SEQUENCE: 54
uguaaacauc cuacacucuc agc                                              23

<210> SEQ ID NO 55
<211> LENGTH: 22
<212> TYPE: RNA
<213> ORGANISM: Homo sapiens
<220> FEATURE:
<223> OTHER INFORMATION: hsa-miR-30d

<400> SEQUENCE: 55
uguaaacauc cccgacugga ag                                               22

<210> SEQ ID NO 56
<211> LENGTH: 22
<212> TYPE: RNA
<213> ORGANISM: Homo sapiens
<220> FEATURE:
<223> OTHER INFORMATION: hsa-miR-30e-3p

<400> SEQUENCE: 56
cuuucagucg gauguuuaca gc                                               22

<210> SEQ ID NO 57
<211> LENGTH: 23
<212> TYPE: RNA
<213> ORGANISM: Homo sapiens
<220> FEATURE:
<223> OTHER INFORMATION: hsa-miR-34b-5p

<400> SEQUENCE: 57
uaggcagugu cauuagcuga uug                                              23

<210> SEQ ID NO 58
<211> LENGTH: 23
<212> TYPE: RNA
<213> ORGANISM: Homo sapiens
<220> FEATURE:
<223> OTHER INFORMATION: hsa-miR-34c

<400> SEQUENCE: 58
aggcagugua guuagcugau ugc                                              23

<210> SEQ ID NO 59
<211> LENGTH: 22
<212> TYPE: RNA
<213> ORGANISM: Homo sapiens
<220> FEATURE:
<223> OTHER INFORMATION: hsa-miR-34a-3p

<400> SEQUENCE: 59
caaucagcaa guauacugcc cu                                               22

<210> SEQ ID NO 60
<211> LENGTH: 22
<212> TYPE: RNA
<213> ORGANISM: Homo sapiens
<220> FEATURE:

<223> OTHER INFORMATION: hsa-miR-34a-5p

<400> SEQUENCE: 60
uggcaguguc uuagcugguu gu                                    22

<210> SEQ ID NO 61
<211> LENGTH: 22
<212> TYPE: RNA
<213> ORGANISM: Homo sapiens
<220> FEATURE:
<223> OTHER INFORMATION: hsa-miR-146a-5p

<400> SEQUENCE: 61
ugagaacuga auuccauggg uu                                    22

<210> SEQ ID NO 62
<211> LENGTH: 22
<212> TYPE: RNA
<213> ORGANISM: Homo sapiens
<220> FEATURE:
<223> OTHER INFORMATION: hsa-miR-146b-5p

<400> SEQUENCE: 62
ugagaacuga auuccauagg cu                                    22

<210> SEQ ID NO 63
<211> LENGTH: 21
<212> TYPE: RNA
<213> ORGANISM: Homo sapiens
<220> FEATURE:
<223> OTHER INFORMATION: hsa-miR-376a-3p

<400> SEQUENCE: 63
aucauagagg aaaauccacg u                                     21

<210> SEQ ID NO 64
<211> LENGTH: 22
<212> TYPE: RNA
<213> ORGANISM: Homo sapiens
<220> FEATURE:
<223> OTHER INFORMATION: hsa-miR-376b-3p

<400> SEQUENCE: 64
aucauagagg aaaauccaug uu                                    22

<210> SEQ ID NO 65
<211> LENGTH: 21
<212> TYPE: RNA
<213> ORGANISM: Homo sapiens
<220> FEATURE:
<223> OTHER INFORMATION: hsa-miR-376c-3p

<400> SEQUENCE: 65
aacauagagg aaauuccacg u                                     21

<210> SEQ ID NO 66
<211> LENGTH: 22
<212> TYPE: RNA
<213> ORGANISM: Homo sapiens
<220> FEATURE:
<223> OTHER INFORMATION: hsa-miR-663a

<400> SEQUENCE: 66
aggcggggcg ccgcgggacc gc                                    22

```
<210> SEQ ID NO 67
<211> LENGTH: 22
<212> TYPE: RNA
<213> ORGANISM: Homo sapiens
<220> FEATURE:
<223> OTHER INFORMATION: hsa-miR-663b

<400> SEQUENCE: 67
gguggcccgg ccgugccuga gg                                          22

<210> SEQ ID NO 68
<211> LENGTH: 22
<212> TYPE: RNA
<213> ORGANISM: Homo sapiens
<220> FEATURE:
<223> OTHER INFORMATION: hsa-miR-181a-3p

<400> SEQUENCE: 68
accaucgacc guugauugua cc                                          22

<210> SEQ ID NO 69
<211> LENGTH: 23
<212> TYPE: RNA
<213> ORGANISM: Homo sapiens
<220> FEATURE:
<223> OTHER INFORMATION: hsa-miR-181a-5p

<400> SEQUENCE: 69
aacauucaac gcugucggug agu                                         23

<210> SEQ ID NO 70
<211> LENGTH: 23
<212> TYPE: RNA
<213> ORGANISM: Homo sapiens
<220> FEATURE:
<223> OTHER INFORMATION: hsa-miR-181b-5p

<400> SEQUENCE: 70
aacauucauu gcugucggug ggu                                         23

<210> SEQ ID NO 71
<211> LENGTH: 22
<212> TYPE: RNA
<213> ORGANISM: Homo sapiens
<220> FEATURE:
<223> OTHER INFORMATION: hsa-miR-181c-5p

<400> SEQUENCE: 71
aacauucaac cugucgguga gu                                          22

<210> SEQ ID NO 72
<211> LENGTH: 22
<212> TYPE: RNA
<213> ORGANISM: Homo sapiens
<220> FEATURE:
<223> OTHER INFORMATION: hsa-miR-21-5p

<400> SEQUENCE: 72
uagcuuauca gacugauguu ga                                          22

<210> SEQ ID NO 73
<211> LENGTH: 21
<212> TYPE: RNA
<213> ORGANISM: Homo sapiens
<220> FEATURE:
<223> OTHER INFORMATION: hsa-miR-21-3p
```

<400> SEQUENCE: 73
caacaccagu cgaugggcug u                                              21

<210> SEQ ID NO 74
<211> LENGTH: 23
<212> TYPE: RNA
<213> ORGANISM: Homo sapiens
<220> FEATURE:
<223> OTHER INFORMATION: hsa-miR-137

<400> SEQUENCE: 74
uuauugcuua agaauacgcg uag                                            23

<210> SEQ ID NO 75
<211> LENGTH: 22
<212> TYPE: RNA
<213> ORGANISM: Homo sapiens
<220> FEATURE:
<223> OTHER INFORMATION: hsa-miR-766-3p

<400> SEQUENCE: 75
acuccagccc cacagccuca gc                                             22

<210> SEQ ID NO 76
<211> LENGTH: 22
<212> TYPE: RNA
<213> ORGANISM: Homo sapiens
<220> FEATURE:
<223> OTHER INFORMATION: hsa-miR-424-5p

<400> SEQUENCE: 76
cagcagcaau ucauguuuug aa                                             22

<210> SEQ ID NO 77
<211> LENGTH: 22
<212> TYPE: RNA
<213> ORGANISM: Homo sapiens
<220> FEATURE:
<223> OTHER INFORMATION: hsa-miR-193a-3p

<400> SEQUENCE: 77
aacuggccua caaaguccca gu                                             22

<210> SEQ ID NO 78
<211> LENGTH: 22
<212> TYPE: RNA
<213> ORGANISM: Homo sapiens
<220> FEATURE:
<223> OTHER INFORMATION: hsa-miR-193b-3p

<400> SEQUENCE: 78
aacuggcccu caaagucccg cu                                             22

<210> SEQ ID NO 79
<211> LENGTH: 22
<212> TYPE: RNA
<213> ORGANISM: Homo sapiens
<220> FEATURE:
<223> OTHER INFORMATION: hsa-miR-214-3p

<400> SEQUENCE: 79
acagcaggca cagacaggca gu                                             22

<210> SEQ ID NO 80
<211> LENGTH: 23

```
<212> TYPE: RNA
<213> ORGANISM: Homo sapiens
<220> FEATURE:
<223> OTHER INFORMATION: hsa-miR-155-5p

<400> SEQUENCE: 80
uuaaugcuaa ucgugauagg ggu                                              23

<210> SEQ ID NO 81
<211> LENGTH: 23
<212> TYPE: RNA
<213> ORGANISM: Homo sapiens
<220> FEATURE:
<223> OTHER INFORMATION: miR-199a-5p

<400> SEQUENCE: 81
cccaguguuc agacuaccug uuc                                              23

<210> SEQ ID NO 82
<211> LENGTH: 23
<212> TYPE: RNA
<213> ORGANISM: Homo sapiens
<220> FEATURE:
<223> OTHER INFORMATION: miR-199b-5p

<400> SEQUENCE: 82
cccaguguuu agacuaucug uuc                                              23

<210> SEQ ID NO 83
<211> LENGTH: 22
<212> TYPE: RNA
<213> ORGANISM: Homo sapiens
<220> FEATURE:
<223> OTHER INFORMATION: miR-345-5p

<400> SEQUENCE: 83
gcugacuccu aguccagggc uc                                               22

<210> SEQ ID NO 84
<211> LENGTH: 23
<212> TYPE: RNA
<213> ORGANISM: Homo sapiens
<220> FEATURE:
<223> OTHER INFORMATION: miR-181b-5p

<400> SEQUENCE: 84
aacauucauu gcugucggug ggu                                              23

<210> SEQ ID NO 85
<211> LENGTH: 22
<212> TYPE: RNA
<213> ORGANISM: Homo sapiens
<220> FEATURE:
<223> OTHER INFORMATION: miR-183-3p

<400> SEQUENCE: 85
gugaauuacc gaagggccau aa                                               22

<210> SEQ ID NO 86
<211> LENGTH: 21
<212> TYPE: RNA
<213> ORGANISM: Homo sapiens
<220> FEATURE:
<223> OTHER INFORMATION: miR-215-5p

<400> SEQUENCE: 86
```

| | |
|---|---|
| augaccuaug aauugacaga c | 21 |

<210> SEQ ID NO 87
<211> LENGTH: 21
<212> TYPE: RNA
<213> ORGANISM: Homo sapiens
<220> FEATURE:
<223> OTHER INFORMATION: miR-31-5p

<400> SEQUENCE: 87

| | |
|---|---|
| aggcaagaug cuggcauagc u | 21 |

<210> SEQ ID NO 88
<211> LENGTH: 22
<212> TYPE: RNA
<213> ORGANISM: Homo sapiens
<220> FEATURE:
<223> OTHER INFORMATION: miR-375-5p

<400> SEQUENCE: 88

| | |
|---|---|
| uuuguucguu cggcucgcgu ga | 22 |

<210> SEQ ID NO 89
<211> LENGTH: 22
<212> TYPE: RNA
<213> ORGANISM: Homo sapiens
<220> FEATURE:
<223> OTHER INFORMATION: miR-409-3p

<400> SEQUENCE: 89

| | |
|---|---|
| gaauguugcu cggugaaccc cu | 22 |

<210> SEQ ID NO 90
<211> LENGTH: 24
<212> TYPE: RNA
<213> ORGANISM: Homo sapiens
<220> FEATURE:
<223> OTHER INFORMATION: miR-125a-5p

<400> SEQUENCE: 90

| | |
|---|---|
| ucccugagac ccuuuaaccu guga | 24 |

<210> SEQ ID NO 91
<211> LENGTH: 22
<212> TYPE: RNA
<213> ORGANISM: Homo sapiens
<220> FEATURE:
<223> OTHER INFORMATION: miR-483-5p

<400> SEQUENCE: 91

| | |
|---|---|
| aagacgggag gaaagaaggg ag | 22 |

<210> SEQ ID NO 92
<211> LENGTH: 22
<212> TYPE: RNA
<213> ORGANISM: Homo sapiens
<220> FEATURE:
<223> OTHER INFORMATION: miR-150-5p

<400> SEQUENCE: 92

| | |
|---|---|
| ucucccaacc cuuguaccag ug | 22 |

BIOMARKERS FOR DETECTING SENESCENT CELLS

GOVERNMENT LICENSE RIGHTS

This invention was made with Unites States government support under Grant No. P01-AG017242 awarded by the NIH. The United States government has certain rights in this invention.

CROSS-REFERENCE TO RELATED APPLICATIONS

This application is the U.S. national stage of International Patent Application No. PCT/EP2018/067063, filed on Jun. 26, 2018 and entitled NOVEL BIOMARKERS FOR DETECTING SENESCENT CELLS, which claims the benefit of priority under 35 U.S.C. § 119 from European Patent Application No. 17177840.0, filed Jun. 26, 2017. The disclosures of the foregoing applications are incorporated herein by reference in their entirety.

SEQUENCE LISTING

The entire content of a Sequence Listing titled "Sequence_ Listing.txt," created on Dec. 19, 2019 and having a size of 16 kilobytes, which has been submitted in electronic form in connection with the present application, is hereby incorporated by reference herein in its entirety.

FIELD OF THE INVENTION

The present invention provides a method, specifically an in vitro method, of detecting senescent cells or diagnosing cellular senescence in a subject wherein the level of one or more selected miRNAs is quantified in a sample from said subject.

BACKGROUND OF THE INVENTION

Cellular senescence, a stable form of cell cycle arrest, is a mechanism that limits the proliferative potential of cells. The senescence response can be triggered in many cell types in response to diverse cellular stressors. It is a potent barrier to tumorigenesis and contributes to the cytotoxicity of certain anti-cancer agents. While senescence limits tumorigenesis and tissue damage in a cell autonomous manner, senescent cells can induce inflammation, tissue ageing and destruction, and promote tumorigenesis and metastasis in a cell non-autonomous manner.

Senescent cells contribute to the decline of body functions and promote the onset of age-associated diseases by the pro-inflammatory secretory activity termed the senescence-associated secretory phenotype (SASP), by loss of replicative potential and thus loss of regenerative capacity, and by loss of tissue and cell type specific functionality including de- or transdifferentiation. Removal of senescent cells by a p16 promoter-driven suicide gene or by compounds that specifically kill senescent cells has beneficial effects on the healthspan of mouse models, delaying the onset of kidney failure, osteoporosis and other age-associated diseases.

Recent research has transitioned cellular senescence from being regarded as a debatable cell culture model of aging to being accepted as contributing factor to age-associated diseases and a potential drug target. By now it is clear that senescent cells occur in vivo in a variety of human tissues, including the skin, cardiovascular system, kidney, liver, the immune system, bone, white adipose tissue and lung, as well as in brain associated with Alzheimers disease or glioblastoma and also in mice, especially in the lung, spleen, dermis, liver and gut epithelium.

In genetically altered mouse models, where such senescent cells can be removed by activation of recombinant suicide genes controlled by the p16 promoter, a marker of senescent cells and later onset of age-associated diseases was observed (Baker et al. 2011, 2016). Among the age-associated diseases specifically tested in this model system are kidney diseases (Baker et al. 2016), but senescent cells are also involved in osteoporosis, osteoarthritis, atherosclerosis and cardiac fibrosis.

This negative impact of accumulated senescent cells in tissues is thought to be caused primarily by the senescence-associated secretory phenotype (SASP). SASP is characterized by an increase of pro-inflammatory, but also extracellular matrix remodelling factors that promote normal and tumor cell proliferation. However, the cells can also have a negative impact—the changed physiology or differentiation status of senescent cells themselves might contribute to the aging process.

Still, the transient presence of senescent cells has been found to be beneficial in wound healing, limiting liver fibrosis and fine-tuning embryonic development.

The search for chemical compounds that specifically kill senescent cells has started and already identified several such compounds, including quercetin, dasatinib (Zhu et al. 2015), navitoclax (Zhu et al. 2016), ABT263 (Chang et al. 2016) and FOXO4 inhibiting peptides (Baar et al. 2017). These pharmacologic compounds are intended for the treatment of age-associated diseases, as well as to alleviate side-effects of therapies resulting in stress-induced cellular senescence, such as chemotherapy.

To develop senolytic therapeutics, novel biomarkers are required. Biomarkers are defined as measurable indicators of a specific biological state, particularly one relevant to the risk of the presence or the stage of disease. In the context of senolytic therapies, biomarkers would be present before therapy and missing after therapy, reflecting the presence and then absence of senescent cells. Some opinion papers claim the use of several SASP proteins that might be secreted into the circulation for this purpose (Matjusaitis et al. 2016).

Biomarkers frequently find clinical utility in the form of companion (CDx) or complementary diagnostic tests. CDx are diagnostic tests that provide information required for the safe and efficacious use of a corresponding drug or biological product. In the context of senolytic therapies, such biomarkers (or CDx tests) must be sensitive and specific to the presence or absence of senescent cells in various tissues.

To date, cell-free (circulating) miRNAs have not been discussed as potential biomarkers for cellular senescence. In cell-free blood, miRNAs have been identified either as bound to protein complexes or as packaged into extracellular vesicles (Turchinovich et al. 2013). They also have been suggested as potential diagnostic or prognostic indicators of several diseases (Schraml and Grillari 2012; Hackl et al. 2015), including cancer (Mitchell et al. 2008a), osteoporosis, osteoarthritis (Beyer et al. 2015) and cardiovascular disease (Zampetaki et al. 2010, 2012). However, it is unclear if cell-free, circulating microRNAs can be used to detect the presence or removal of senescent cells in vivo.

Currently, the monitoring of senescent cell removal in wild type animals and humans is challenging, since the identification of senescent cells require invasive techniques such as tissue biopsies. This is a major disadvantage, because the analysis is locally restricted to a specific tissue, potentially missing effects that are ongoing in other tissues. In addition, the use of biomarkers to specifically distinguish senescent from non-senescent cells in human tissues is still a matter of debate. Therefore, there is an unmet demand for minimally-invasive novel biomarkers and diagnostic methods to detect the presence of senescent cells.

DESCRIPTION OF THE INVENTION

It is an object of the invention to provide senolytic biomarkers for detecting and monitoring the presence, as well as accumulation, of scenescent cells, for diagnosing cellular senescence in a subject, and determining the presence of senescent cells in the context of diagnosing the risk of senescence-related diseases, and monitoring the efficacy of senolytic drugs.

The object is solved by the subject matter of the present invention.

It has been shown in the embodiment of the invention that cell-free, circulating microRNAs can be used to detect the presence or removal of senescent cells in a subject.

It is claimed that cell-free (circulating) miRNAs, which can be detected in cell-free biofluids such as serum, plasma, urine and saliva, can be used to identify the presence, accumulation and removal of senescent cells, which, as a companion or complementary diagnostic method for senolytic therapies, is required to identify individuals with high levels of senescent cells, for dosing of senolytic drugs as well as for monitoring treatment response.

The present invention provides a method of detecting senescent cells or diagnosing cellular senescence and/or monitoring senolytic treatment success in a subject, the method comprising the sequential steps of:
a) providing a cell-free sample from said subject,
b) quantifying the level of one or more miRNAs selected from the group consisting of miRNAs listed in Table 1 or isoforms thereof in said sample and
c) optionally comparing the level of b) with the reference level of said one or more miRNAs in a reference sample, wherein a difference between said levels is indicative of the presence of senescent cells or cellular senescence.

In an embodiment of the present invention, the level of said one or more miRNAs is measured and compared with a reference level, wherein the magnitude of difference of the level comparison is indicative of the presence of senescent cells or indicative for cellular senescence.

The present invention encompasses also an in vitro method of detecting senescent cells or diagnosing cellular senescence and/or monitoring senolytic treatment success in a subject, the method comprising the steps of:
a) providing a cell-free sample from said subject,
b) measuring the level of one or more miRNAs selected from the group consisting of miRNAs listed in Table 1 or isoforms thereof, and
c) comparing the level of said miRNAs with the level of said one or more miRNAs in a reference sample, wherein the magnitude of difference when comparing the respective miRNA levels is indicative of the presence of senescent cells or indicative of cellular senescence. The level of miRNAs in the reference sample is the reference level.

In a further embodiment, the level of (i) miR-34a-5p (ii) miR-27a-3p, and (iii) one or more further miRNAs listed in Table 1 is quantified. According to a further embodiment, further the level of miR-137, miR-766-3p, miR-424-5p or any combination thereof is quantified.

In a further embodiment herein provided is an in vitro method of detecting senescent cells, diagnosing cellular senescence and/or monitoring senolytic treatment success in a subject, the method comprising the steps of:
a) providing a cell-free sample from said subject,
b) quantifying the level of one or more miRNAs selected from the group consisting of miRNAs listed in Table 19 or isoforms thereof in said sample, and
c) optionally comparing the level of b) with the reference level of said one or more miRNAs in a reference sample wherein a difference between said levels is indicative of the presence of senescent cells or cellular senescence.

In a specific embodiment, the level of one or more of miRNAs selected from the group consisting of let-7a-5p, let-7b-5p, miR-199a-5p, miR-345-5p, miR-423-3p, and miR-125a-5p is quantified.

In a further embodiment, the level of one or more miRNAs selected from the group consisting of let-7a-5p, let-7b-5p, miR-34a-5p, miR-34a-3p, miR-151-5p, miR-155-5p, miR-199a-5p, miR-199b-5p and miR-345-5p is quantified.

In yet a further embodiment, the level of one or more miRNAs selected from the group consisting of miR-23a-3p, miR-23b-3p, miR-24-3p, miR-27a-3p, miR-146a-5p, miR-423-3p, miR-181b-5p, miR-183-3p, miR-215-5p, miR-31-5p, miR-375-5p, miR-409-3p, miR-125a-5p, miR-483-5p, and miR-150-5p is quantified.

According to a further embodiment, the level of one or more further miRNAs selected from the group consisting of miRNAs listed in Table 2 is quantified.

According to a further embodiment, the level of one or more further miRNAs selected from the group consisting of miRNAs listed in Table 3 is quantified.

According to a further embodiment, the level of one or more further miRNAs selected from the group consisting of miRNAs listed in Table 4 is quantified.

According to a further embodiment, the level of one or more further miRNAs selected from the group consisting of miRNAs listed in Table 5 is quantified.

According to a further embodiment, the level of one or more further miRNAs selected from the group consisting of miRNAs listed in Table 6 is quantified.

According to a further embodiment, the level of one or more further miRNAs selected from the group consisting of miRNAs listed in Table 7 is quantified.

According to a further embodiment, the level of one or more further miRNAs selected from the group consisting of miRNAs listed in Table 8 is quantified.

According to a further embodiment, the level of one or more further miRNAs selected from the group consisting of miRNAs listed in Table 9 is quantified.

According to a further embodiment, the level of one or more further miRNAs selected from the group consisting of miRNAs listed in Table 10 is quantified.

According to a further embodiment, the level of one or more further miRNAs selected from the group consisting of miRNAs listed in Table 11 is quantified.

According to a further embodiment, the level of one or more further miRNAs selected from the group consisting of miRNAs listed in Table 12 is quantified.

According to a further embodiment, the level of one or more further miRNAs selected from the group consisting of miRNAs listed in Table 13 is quantified.

According to a further embodiment, the level of one or more further miRNAs selected from the group consisting of miRNAs listed in Table 14 is quantified.

According to a further embodiment, the level of one or more further miRNAs selected from the group consisting of miRNAs listed in Table 15 is quantified.

According to a further embodiment, the level of one or more further miRNAs selected from the group consisting of miRNAs listed in any one of Tables 2 to 15 in any combination is quantified.

According to a further embodiment, the levels of two or more miRNAs from at least 2, 3, 4, 5, 6, 7, 8, 9, 10, 11, 12, 13, 14, 15, 16, 17, 18, 19 different groups as listed in any one of Tables 2 to 15 and Tables 19 to 22 are quantified.

According to a further embodiment, the level of at least 3, or at least 4, or at least 5, specifically up to 30 miRNAs or more is quantified.

In an alternative embodiment, the levels of 2, 3, 4, 5, 6, 7, 8, 9, 10, 11, 12, 13, 14, 15, 16, 17, 18, 19, 20, 21, 22, 23, 24 or more miRNAs are quantified.

According to a further embodiment, the reference level is the level of the corresponding miRNAs in a sample of a healthy subject or the miRNA level of a pool of samples from healthy subjects and/or the level of the respective miRNA in a subject prior to a pharmacologic, such as senolytic, dietary or life-style intervention or of a pool of samples from subjects prior to a pharmacologic, dietary or life-style intervention or the average level of said miRNAs in the pool of samples.

According to a further embodiment, a difference by more than one standard deviations of the level comparison is indicative of the presence of senescent cells or indicative of cellular senescence.

According to a further embodiment, herein provided is an in vitro method for monitoring senolytic treatment response in a subject, comprising the steps
a) providing a cell-free sample from said subject,
b) quantifying the level of one or more miRNAs selected from the group consisting of miRNAs listed in Table 1 or isoforms thereof in said sample, and
c) comparing the level of b) with the reference level of said one or more miRNAs in an earlier sample from said subject, wherein a more than 1.5 fold difference between said levels is indicative of the response to senolytic treatment.

According to a further embodiment, herein provided is an in vitro method for monitoring senolytic treatment response in a subject, comprising the steps
a) providing a cell-free sample from said subject,
b) quantifying the level of one or more miRNAs selected from the group consisting of miRNAs listed in Tables 19, 21 or 22 or isoforms thereof in said sample, and
c) comparing the level of b) with the reference level of said one or more miRNAs in an earlier sample from said subject. Specifically, a more than 1.5 fold difference between said levels is indicative of the response to senolytic treatment.

According to a further embodiment, the difference in miRNA levels is determined by quantitative or digital PCR, sequencing, microarray, LUMINEX™ bead-based immunoassay for the detection of analytes, such as nucleic acids, or other hybridization-based techniques.

According to a further embodiment, further the level of one or more proteins secreted by senescent cells is measured and compared to a protein reference level, wherein the magnitude of difference in said protein level when compared to the protein reference level is indicative of the presence of senescent cells or cellular senescence.

According to a specific embodiment, the difference by more than one standard deviations of the protein level comparison in combination with the respective miRNA biomarker measurement is indicative of the presence of senescent cells or indicative of cellular senescence.

According to a further embodiment, the subject is at least 30, 40, 50, 60, 70, 80, 90 years of age, specifically it is a subject at risk of age-associated disease and/or at risk of SASP.

According to a further embodiment, the cell-free sample is a cell-free blood sample, specifically a serum or plasma sample.

According to a further embodiment, the cell-free sample is a urine or saliva sample.

A further embodiment of the invention relates to the use of the method described herein for detecting a decline of senescent cells or reduction of cellular senescence, wherein the level of said miRNAs is compared with the level of corresponding miRNAs prior to a treatment with senolytics, anti-aging agents or any anti-aging intervention.

According to a further embodiment, a diagnostic device is herein provided, comprising a panel of miRNAs for detecting senescent cells, diagnosing cellular senescence and/or monitoring senolytic treatment success comprising miRNAs selected from the group consisting of miR-34a-5p, miR-7f-5p, miR-7a-5p, miR-143-3p, miR-27a-3p, miR-143-5p, miR-144-5p, miR-3058-3p, miR-30b-5p, miR-339-5p, miR-423-3p, miR-6395, miR-652-3p, miR-18b-5p, miR-92a-3p and and optionally further comprising one or more of the miRNAs listed in tables 2 to 15 and 19 to 22.

According to a further embodiment, a diagnostic device is herein provided, comprising a panel of miRNAs for detecting senescent cells, diagnosing cellular senescence and/or monitoring senolytic treatment success comprising miRNAs selected from the group consisting of let-7a-5p, let-7b-5p, miR-199a-5p, miR-345-5p, miR-423-3p, miR-125a-5p and optionally further comprising one or more of the miRNAs listed in tables 19, 20 and/or 21.

According to a further embodiment, a diagnostic device is herein provided comprising a panel of miRNAs for detecting senescent cells, diagnosing cellular senescence and/or monitoring senolytic treatment success comprising one or more of the miRNAs listed in tables 19, 20 and/or 21.

According to an alternative embodiment, a diagnostic device is herein provided comprising a panel of miRNAs for detecting senescent cells, diagnosing cellular senescence and/or monitoring senolytic treatment success comprising miRNAs selected from the group consisting of let-7a-5p, let-7b-5p, miR-34a-5p, miR-34a-3p, miR-151-5p, miR-155-5p, miR-199a-5p, miR-199b-5p and miR-345-5p.

According to an alternative embodiment, a diagnostic device is herein provided comprising a panel of miRNAs for detecting senescent cells, diagnosing cellular senescence and/or monitoring senolytic treatment success comprising miRNAs selected from the group consisting of miR-23a-3p, miR-23b-3p, miR-24-3p, miR-27a-3p, miR-146a-5p, miR-423-3p, miR-181b-5p, miR-183-3p, miR-215-5p, miR-31-5p, miR-375-5p, miR-409-3p, miR-125a-5p, miR-483-5p, and miR-150-5p.

According to a further embodiment, the method as described herein can also be used for detecting senescent cells in a sample from a cell culture or from isolated cells cultivated in vitro. Specifically, herein provided is an in vitro method of detecting senescent cells in a sample from a cell culture, the method comprising the steps of:
a) providing sample from said cell culture,
b) quantifying the level of one or more miRNAs selected from the group consisting of miRNAs listed in Table 1 or Table 19 or isoforms thereof in said sample, and c) optionally comparing the level of b) with the reference level of said one or more miRNAs in a reference sample wherein a difference between said levels is indicative of the presence of senescent cells or cellular senescence.

In a further embodiment, a kit of parts is also provided herein comprising a panel of miRNAs as described above together with reference samples or reference level and a software for automation of data normalization and interpretation, specifically the calculation of a single-indexed score, which quantitatively reflects the burden of senescence in said subject, using a classification model.

An apparatus, configured for carrying out the inventive method as described herein, optionally using a software protocol.

A further embodiment of the invention provides an apparatus for detecting senescent cells or diagnosing cellular senescence using the method and biomarkers described herein and configured using a software protocol.

FIGURES

FIG. 1: A) Experiment overview. B) Sequencing results: total reads and annotation.

Figure 2:
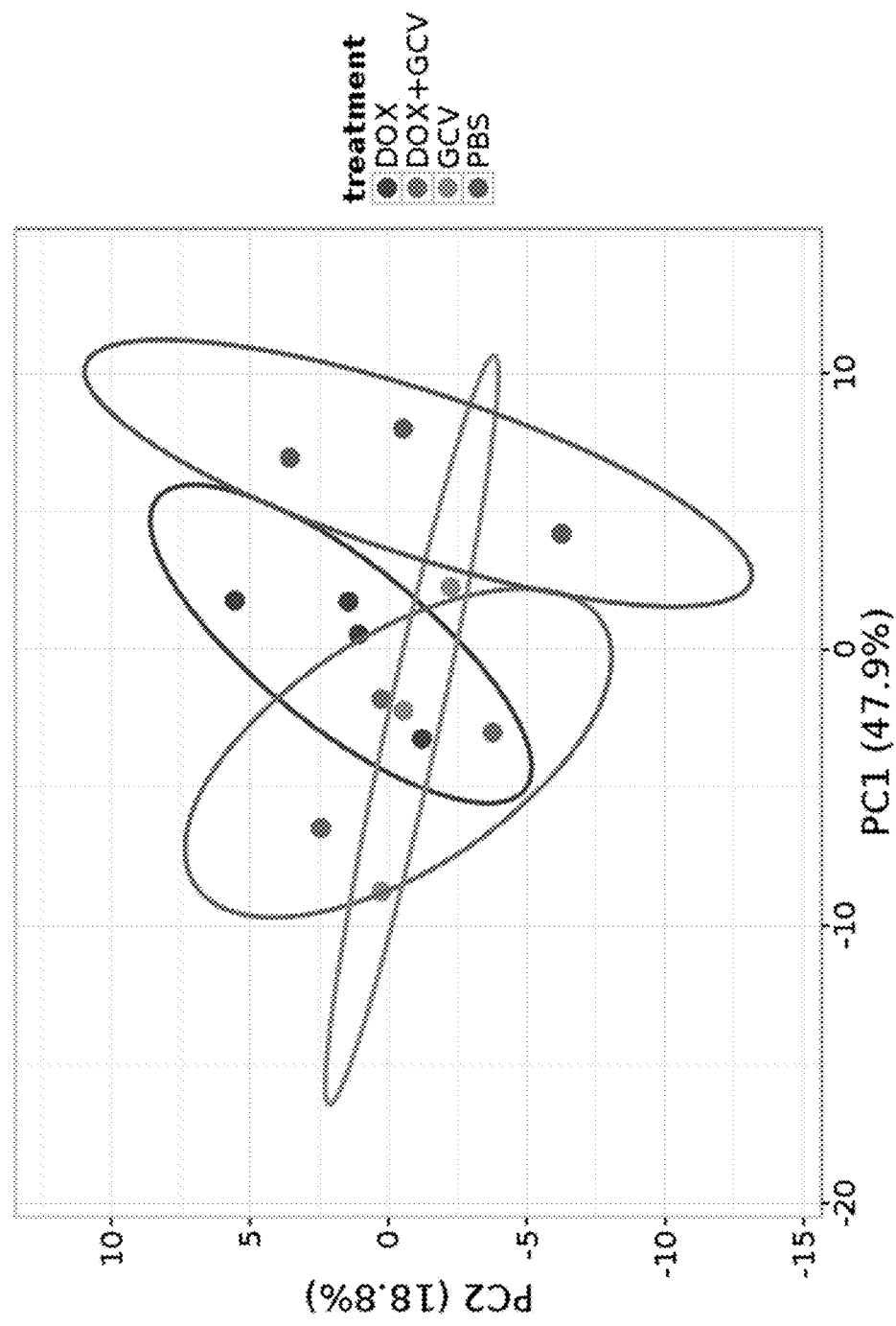

FIG. 2: Principal component analysis. 50 microRNAs with the highest variation across all 13 samples were used for the analysis. The first two principal components explain 66.7% of the variation.

Figure 3:
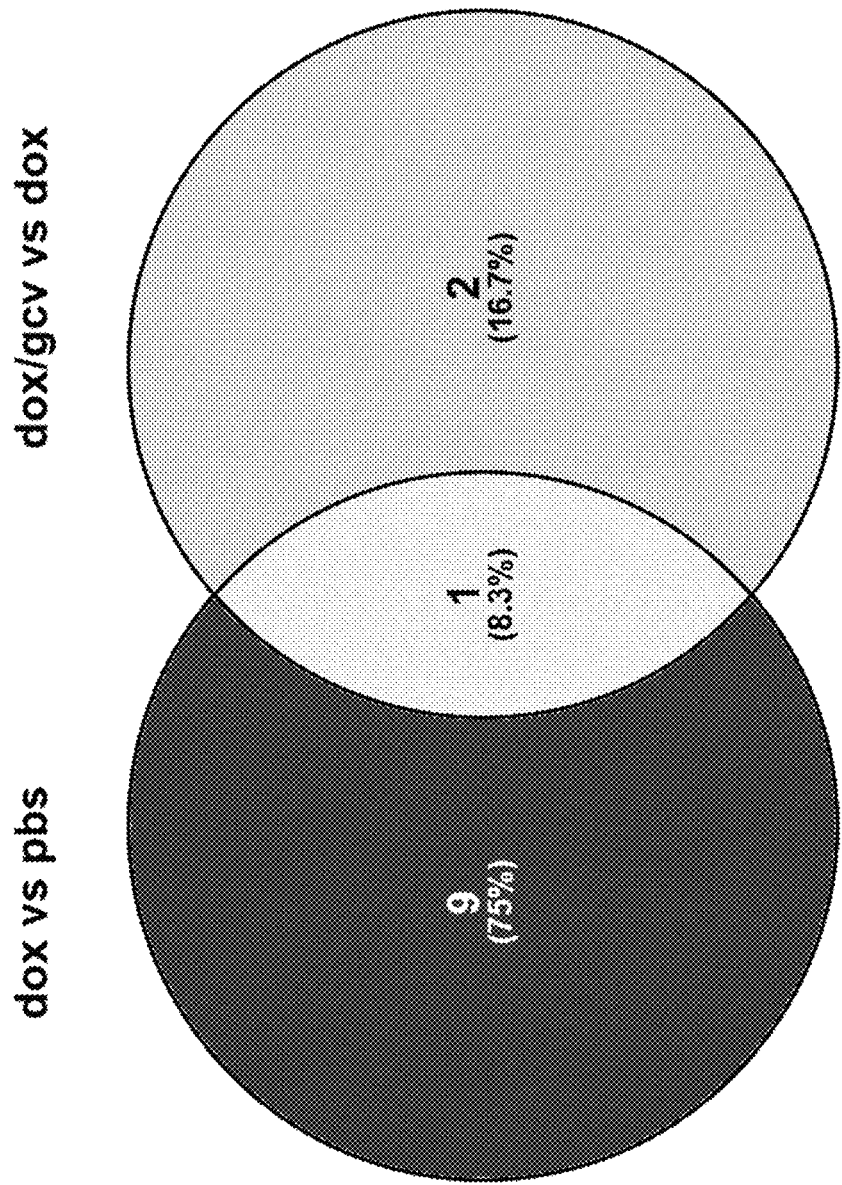
Figure 4:
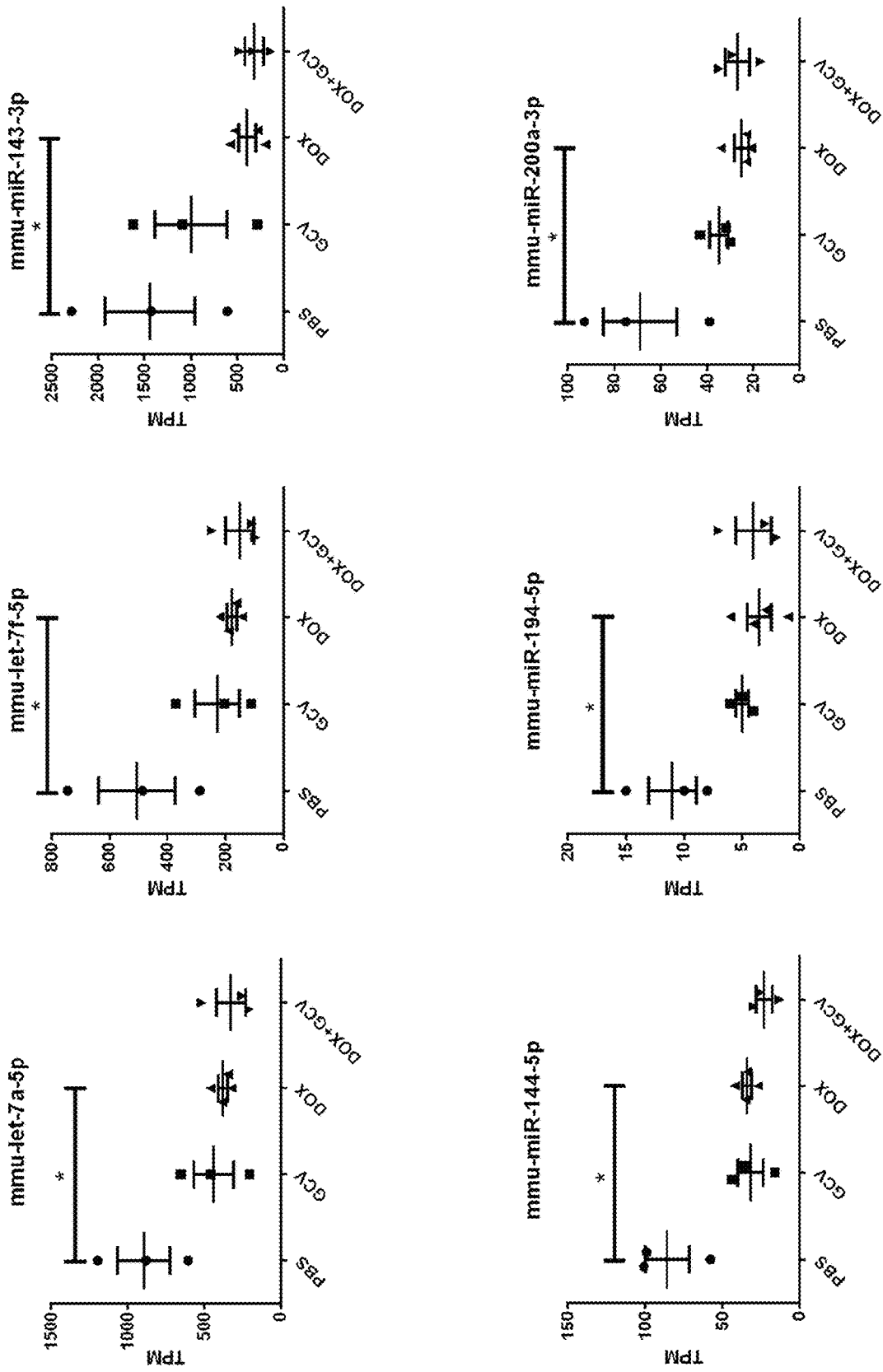
Figure 4:
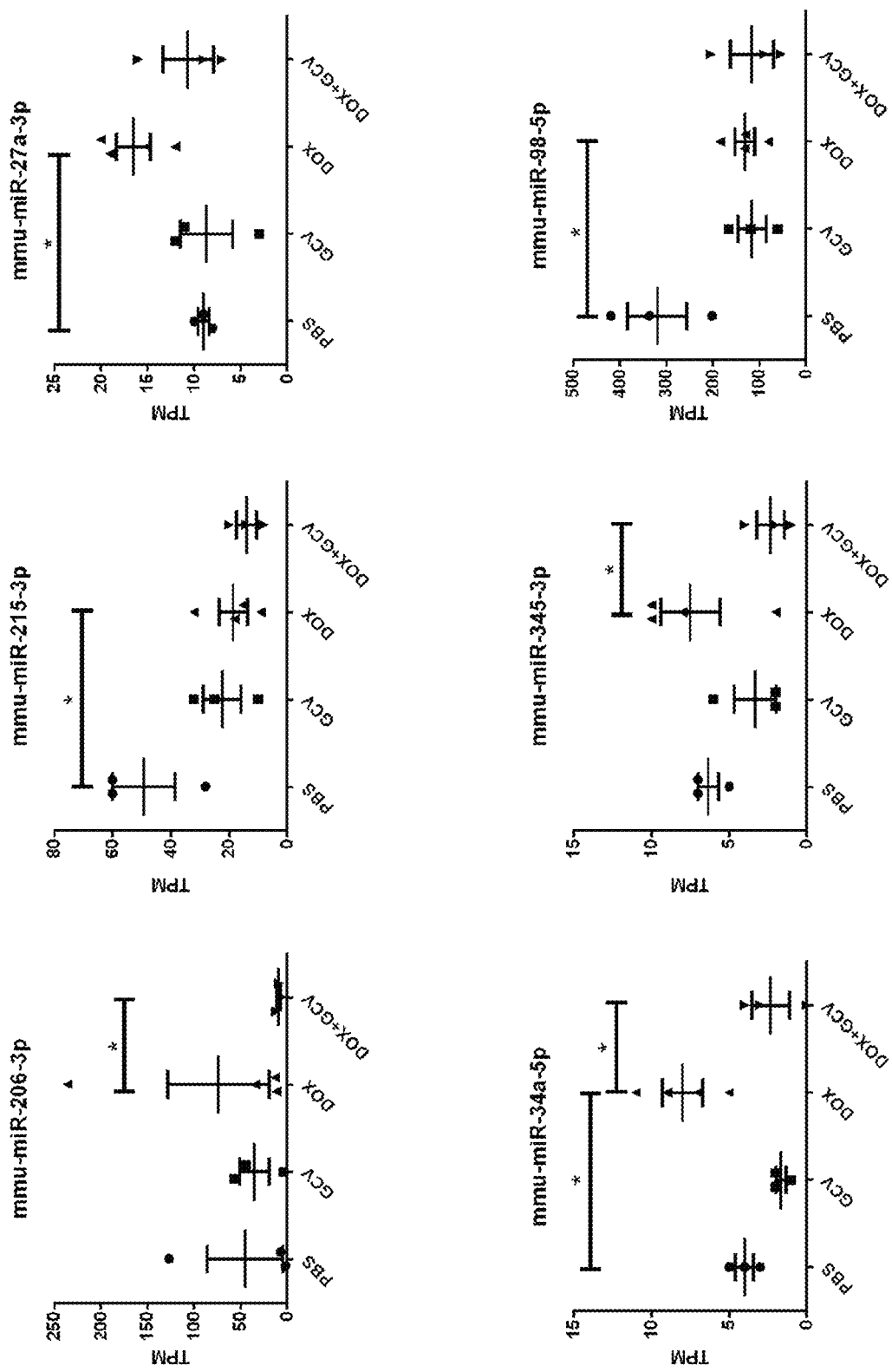
Figure 5:
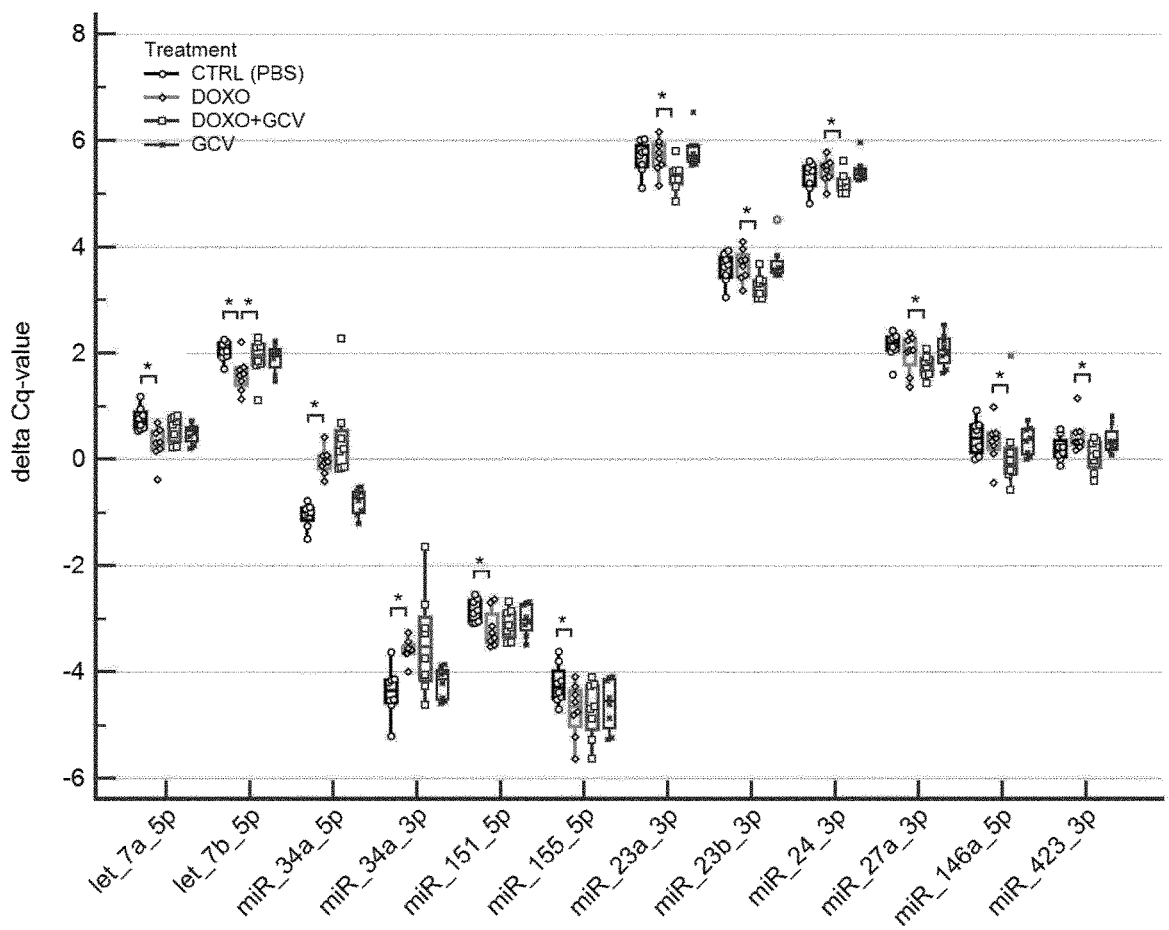
Figure 5:
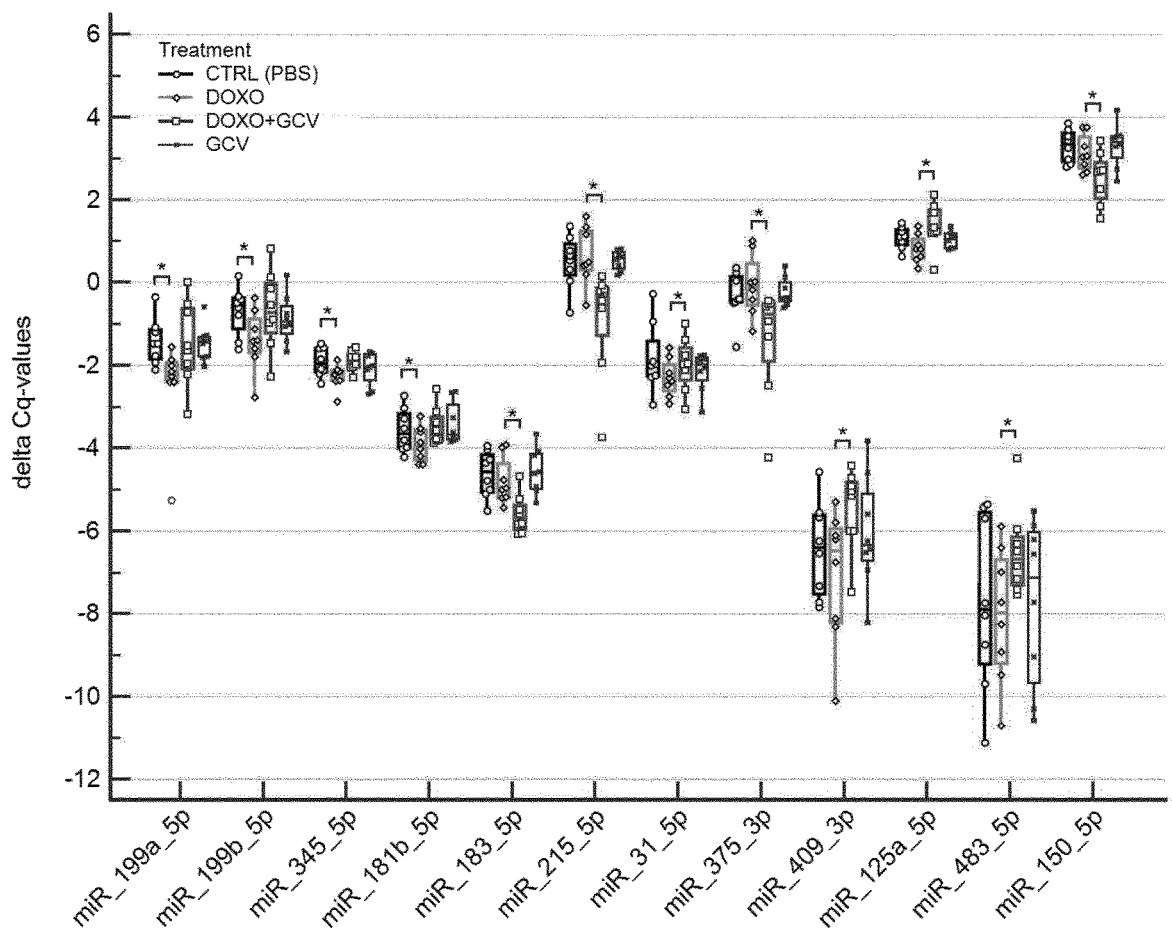

FIG. 3: VENN overlap of differentially regulated miRNAs after induction of senescence (dox vs pbs) and rescue of senescence using ganciclovir (dox/gcv vs dox). List of microRNAs contained in the VENN diagram:

dox vs. pbs: mmu-letf-5p, mmu-miR143-3p, mmu-miR-27a-3p, mmu-miR-144-5p, mmu-miR-34a-5p, mmu-miR-200a-3p, mmu-miR-98-5p, mmu-let-7a-5p, mmu-miR-194-5p, mmu-miR-215-3p dox/gcv vs dox: mmu-miR-34a-5p, mmu-miR-206-3p, mmu-miR-345-3p overlapping zone: mmu-miR-34a-5p FIG. 4: Scatterplots of normalized read counts (TPM) of differentially regulated microRNAs in serum of p16-3MR mice in the control (pbs), ganciclovir (gcv), doxorubicin (dox) and dox+gcv treated animals. Significant differences are highlighted (*). * $p<0.05$, two-tailed t-test FIG. 5: Boxplots of normalized delta Cq-values (dCq) derived from RT-qPCR based verification of NGS results in an independent set of mouse serum samples (n=8 per group), comprising both male and female mice. For the sake of clarity data for 24 microRNAs were split into two graphs, A) and B). One-way ANOVA with post-hoc tests was performed to identify statistically significant changes between groups (*<0.05).

Figure 6:
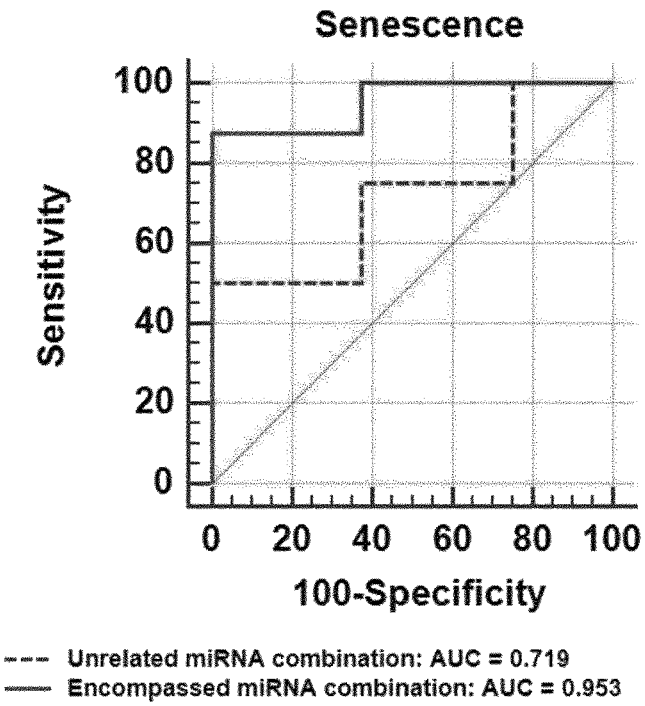
Figure 6:
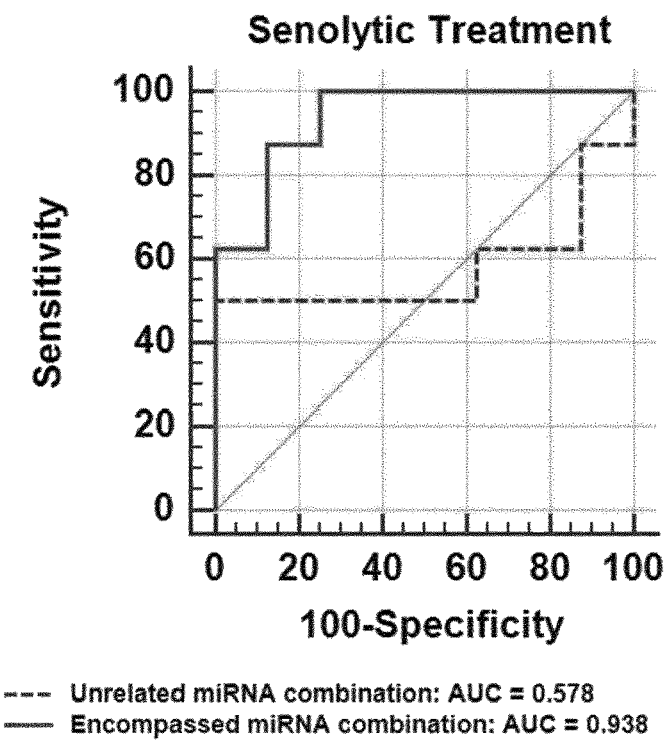

FIG. 6: Direct comparison of the diagnostic performance of encompassed microRNA combinations (let-7a-5p, miR-125a-5p, miR-199a-5p, miR-345-5p, miR-423-3p) versus unrelated microRNA combinations (miR-221-3p, miR-222-3p, miR-22-3p, miR-378a-3p, miR-582-5p) for A) diagnosis of cellular senescence, and B) monitoring of senolytic treatment. AUC-values calculated from ROC-curves are given in the plot legends.

DETAILED DESCRIPTION OF THE INVENTION

Specific terms as used throughout the specification have the following meaning.

The term "comprise", "contain", "have" and "include" as used herein can be used synonymously and shall be understood as an open definition, allowing further members or parts or elements. "Consisting" is considered as a closest definition without further elements of the consisting definition feature. Thus "comprising" is broader and contains the "consisting" definition.

As used in this specification and the appended claims, the singular forms "a", "an", and "the" include plural referents, unless the content clearly dictates otherwise.

The term "about" as used herein refers to the same value or to a value differing by +/−10% of the given value.

Cellular senescence occurs in culture and in vivo as a response to extracellular or intracellular stress. The senescence response locks cells into a cell-cycle arrest that prevents the propagation of damaged cells and precludes potential malignant transformation.

Senescence refers to an array of changes that occurs over time. Compared to a reference cell or sample or subject (e.g., a cell or sample of the same type or age known to be non-senescent), a senescent cell, sample or subject is defined as a cell or subject that shows one, two, three, four, five, six or more or all of any of the following features: a decrease in cell proliferation ability; an accumulation of lipofuscin (e.g., increase in lipofuscin accumulation); an increase in beta-galactosidase activity; an increase of mitochondrial-derived reactive oxygen species; an increase in nuclear DNA damage foci; a shortening of telomeres; increased expression of p16 or p21 or any combination thereof; or a cell or subject shows a process that causes those described above.

The senescent cell or subject may further show a decrease in autophagy activity or a decrease in mitochondrial membrane potential, or shows a process that causes those described above. Compared to a cell or subject such as a known senescent cell or subject, a non-senescent cell or subject may show an increase in cell proliferation ability, a decrease in lipofuscin accumulation, a decrease in β-galactosidase activity, or a combination thereof. In the case of a human, a cell or sample that is taken from a person about 30 years or older, about 40 years or older, about 50 years or older, about 60 years or older, about 70 years or older, about 80 years or older, about 90 years or older, may be defined as a senescent cell or sample.

The terms "cellular senescence" and "senescent cells" thus refer to the essentially irreversible growth arrest that occurs when cells that can divide encounter critically short telomeres, oncogenic stress or DNA damage or experience strong mitogenic signals, such as but not limited to oncogenes or highly expressed pro-proliferative genes and a senescent cell which is a potentially persisting cell that is metabolically active and has undergone widespread changes in protein expression, and secretion, ultimately developing the SASP. This phenotype has also been termed the senescence-messaging secretome, which means that many different proteins have been identified as more abundantly secreted than by quiescent cells. So far, >89 proteins have been described as SASP factors including IL6, IL8 (CXCL8), IGFBPs, or metalloproteinases (MMP1, 2, 3, 10, 12, 13).

Specifically, said proteins can be, but are not limited to Adiponectin (ADIPOQ), Angiogenin (ANG), Amphiregulin (AREG), receptor tyrosine kinase AXL, Probetacellulin (BTC), C-C motif chemokine 1 (CCL1), Eotaxin (C-C motif chemokine 11) (CCL11), C-C motif chemokine 13 (CCL13), C-C motif chemokine 16 (CCL16), C-C motif chemokine 2 (CCL2), C-C motif chemokine 20 (CCL20), C-C motif chemokine 25 (CCL25), C-C motif chemokine 26 (CCL26), C-C motif chemokine 27 (CCL27), C-C motif chemokine 3 (CCL3), C-C motif chemokine 5 (CCLS), C-C motif chemokine 8 (CCL8), Granulocyte-macrophage colony-stimulating factor (CSF2), Cathepsin B (CTSB), Growth-regulated alpha protein (C-X-C motif chemokine 1) (CXCL1), C-X-C motif chemokine 11 (CXCL11), Stromal cell-derived factor 1 (C-X-C motif chemokine 12) (CXCL12), C-X-C motif chemokine 13 (CXCL13), C-X-C motif chemokine 5 (CXCL5), Interleukin 8 (C-X-C motif chemokine 8) (CXCL8), Epidermal Growth Factor (EGF), Epidermal Growth Factor Receptor (EGFR), Epiregulin (EREG), Tumor necrosis factor receptor superfamily member 6 (FAS), Fibroblast Growth Factor 2 (FGF2), Fibroblast Growth Factor 7 (FGF7), Glial cell line-derived neurotrophic factor (GDNF), Hepatocyte growth factor (HGF), Intercellular adhesion molecule 1 (ICAM1), Intercellular adhesion molecule 3 (ICAM3), Interferon Gamma (IFNG), Insulin-like growth factor-binding protein 1 (IGFBP1), Insulin-like growth factor-binding protein 2 (IGFBP2), Insulin-like growth factor-binding protein 3 (IGFBP3), Insulin-like growth factor-binding protein 4 (IGFBP4), Insulin-like growth factor-binding protein 5 (IGFBP5), Insulin-like growth factor-binding protein 6 (IGFBP6), Insulin-like growth factor-binding protein 7 (IGFBP7), Interleukin-11 (IL11), Interleukin-13 (IL13), Interleukin-15 (IL15), Interleukin-1 alpha (IL1A), Interleukin-1 beta (IL1B), Interleukin-1 receptor type 1 (IL1 R1), Interleukin-2 receptor subunit alpha (IL2RA), Interleukin-6 (IL6), Interleukin-6 receptor subunit beta (I L6ST), Interleukin-7 (IL7), Inhibin beta A chain (INHBA), Kit ligand (KITLG), Leptin (LEP), Leukemia inhibitory factor (LIF), Macrophage migration inhibitory factor (MIF), Interstitial collagenase (MMP1), Stromelysin-2 (MMP10), Macrophage metalloelastase (MMP12), Collagenase 3 (MMP13), Matrix metalloproteinase-14 (MMP14), 72 kDa type IV collagenase (MMP2), Stromelysin-1 (MMP3), Nucleosome assembly protein 1-like 4 (NAP1L4), Beta-nerve growth factor (NGF), Neuregulin-1 (NRG1), Oncostatin-M (OSM), Platelet-derived growth factor subunit B (PDGFB), Phosphatidylinositol-glycan biosynthesis class F protein (PIGF), Tissue-type plasminogen activator (PLAT), Urokinase-type plasminogen activator (PLAU), Urokinase plasminogen activator surface receptor (PLAUR), Plasminogen activator inhibitor 2 (SERPINB2), Plasminogen activator inhibitor 1 (SERPINE1), Serine/threonine-protein kinase 4 (STK4), Thrombopoietin (THPO), Metalloproteinase inhibitor 1 (TIMP1), Metalloproteinase inhibitor 2 (TIMP2), Tumor necrosis factor receptor superfamily member 10C (TNFRSF10C), Tumor necrosis factor receptor superfamily member 11B (TNFRSF11B), Tumor necrosis factor receptor superfamily member 18 (TNFRSF18), Tumor necrosis factor receptor superfamily member 1A (TNFRSF1A), Gamma-tubulin complex component 2 (TUBGCP2), Vascular endothelial growth factor A (VEGFA).

Measuring the expression rate or secretion of one or more of above listed proteins may be a further element of the method as described herein, thus an increase or decrease of protein expression and secretion can be indicative for the presence of senescent cells, cellular senescence or response to senolytic treatment.

The term "senescent cells" specifically refers to cells that express a marker or combination of markers that are characteristic of senescence. Such markers include but are not limited to the $p16^{INK4a}$ tumor-suppressor protein, and increased expression relative to a reference, such as a non-senescent cell, in the levels of DNA-damage response (DDR) markers, co-localization of DNA damage proteins like 53BP1 or gammaH2AX with telomeres, as well as the cell cycle inhibitors $p16^{INK4A}$, $p15^{INK4B}$, $p21^{CIP1}$, and p53. DEC1, DCR2, and PAI1 can also be used as senescence biomarkers. In one embodiment, senescent cells express SA-beta-Gal (senescence-associated beta galactosidase) to an extent that staining with X-Gal results in a blue color, also referred to as "positive staining".

"Culture stress", the natural and in vivo equivalent of which are unknown, causes a senescence arrest without significant telomere erosion. These stresses may include inappropriate substrate, e.g., tissue culture plastic, serum (most cells experience plasma, not serum, in vivo), and oxidative stress, e.g., culture in atmospheric $O_2$, which is hyperphysiological. Cells also senesce upon loss of the PTEN tumor suppressor, a phosphatase that counteracts pro-proliferative/pro-survival kinases. Additionally, ectopic expression of the cyclin-dependent kinase inhibitors (CD-Kis) that normally enforce the senescence growth arrest, notably p21WAF1 and/or $p16^{INK4a}$, may cause senescence.

"Aging" according to this invention is a combination of processes of deterioration that follow the period of development of an organism. Aging is generally characterized by a declining adaptability to stress, increased homeostatic imbalance, increase in senescent cells, and increased risk of disease. Because of this, death is the ultimate consequence of aging.

Acceleration of the rate of aging may be induced by stress conditions including, but not limited to chemical, physical, and biological stresses. For example, accelerated aging can be induced by stresses caused by UV and IR irradiation, drugs and other chemicals, chemotherapy, intoxicants, such as but not limited to DNA intercalating and/or damaging agents, oxidative stressors etc; mitogenic stimuli, oncogenic stimuli, toxic compounds, hypoxia, oxidants, caloric restriction, exposure to environmental pollutants, for example, silica, exposure to an occupational pollutant, for example, dust, smoke, asbestos, or fumes. In some embodiments, the subject has smoked cigarettes. All these stressors alone or in combination can also cause cellular senescence.

Cellular senescence may also be caused by telomeric dysfunction (telomere uncapping) resulting from repeated cell division (termed replicative senescence), mitochondrial deterioration, oxidative stress, severe or irreparable DNA damage and chromatin disruption (genotoxic stress), and the expression of certain oncogenes (oncogene-induced senescence). Stresses that cause cellular senescence can be induced by external or internal chemical and physical insults encountered during the course of the life span, during therapeutic interventions (for example, X-irradiation or chemotherapy), or as a consequence of endogenous processes such as oxidative respiration and mitogenic signals. External mitogenic signals, for example growth-related oncogene alpha (GROα) secretion by tumor cells in close proximity to normal cells or circulating angiotensin II, have also been shown to induce cellular senescence. All somatic cells that have the ability to divide can undergo senescence. Regardless of the disparate mechanisms of senescence-inducing stresses, the senescence program is activated once a cell has sensed a critical level of damage or dysfunction. So far, the senescence growth arrest has been shown to depend on the activities of the major tumor-suppressor pathways controlled by $p16^{INK4a}$ and pRB (retinoblastoma protein), as well as by p53. Some of the molecules involved in pathways upstream and downstream of the senescence-associated phenotype have been used as markers to detect senescent cells in culture and in vivo.

Non-limiting examples of chemotherapeutic agents include anthracyclines, doxorubicin, daunorubicin, taxols, paclitaxel, gemcitabine, pomalidomide, and lenalidomide.

In some aspects of the invention, senescence is induced by combinations of stresses, e.g., two or more chemical and physical stresses; two or more chemical and biological stresses; two or more physical and biological stresses; chemical, physical, and biological stresses in combination, etc.

Circulating microRNAs in cell-free blood such as serum or plasma are a minimal or non-invasive source of biomarkers allowing minimal-invasive detection and therefore a broad applicability in clinics and research repositories.

The term "senolytic treatment" refers to the exposure of the cells or subjects to senolytic drugs or agents, which induce lysis of senescent cells and thereby can delay, prevent, alleviate, or reverse age-related or stress-induced diseases.

Senolytic agents or drugs are agents that selectively induce apoptosis of senescent cells by killing senescent cells. In other words, a senolytic agent destroys or kills a senescent cell in a biologically, clinically, and/or statistically significant manner compared with its capability to destroy or kill a non-senescent cell. In certain embodiments, the senolytic agents alter at least one signaling pathway in a manner that induces (initiates, stimulates, triggers, activates, promotes) and results in (i.e., causes, leads to) death of the senescent cell. The senolytic agent may alter, for example, either or both of a cell survival signaling pathway (e.g., Akt pathway) or an inflammatory pathway, for example, by antagonizing a protein within the cell survival and/or inflammatory pathway in a senescent cell. Senolytic agents alter (i.e., interfere with, affect) one or more cellular pathways that are activated during the senescence process of a cell. Senolytic agents may alter either a cell survival signaling pathway (e.g., Akt pathway) or an inflammatory pathway or alter both a cell survival signaling pathway and an inflammatory pathway in a senescent cell. Activation of certain cellular pathways during senescence decreases or inhibits the cell's capability to induce, and ultimately undergo apoptosis.

Such agents may be but are not limited to small molecules, HSP90 inhibitors, agents targeting Bcl-2 family of anti-apoptotic factors such as navitoclax and TW-37, murine double minute 2 (MDM2) inhibitors such as a cis-imidazoline compound, a spiro-oxindole compound, a benzodiazepine compound, a piperidinone compound, a tryptamine compound, and CGM097, and related analogs. In certain embodiments, the MDM2 inhibitor is also capable of binding to and inhibiting an activity of MDMX (murine double minute X, which is also known as HDMX in humans). The human homolog of MDM2 is called HDM2 (human double minute 2) in the art. Akt (Protein kinase B, PkB) kinase inhibitors, such as compounds that selectively inhibit its three isoforms Akt1, Akt2, and Akt3, relative to other protein kinases. Akt inhibitors have evolved from adenosine triphosphate (ATP)-competitive agents to alternative approaches employing allosteric sites in order to overcome the high degree of structural similarity between Akt isoforms in the catalytic domain, and considerable structural analogy to the AGC kinase family, resulting in inhibitors with greater specificity, reduced side-effects and lower toxicity, such as Uprosertib, Afuresertib, MK-2206, and Ipatasertib. Other agents such as ganciclovir (GCV) or AP20187 can also act as senolytics and are encompassed herein. In other embodiments, senolytic agents may be a polypeptide, peptide, antibody, antigen-binding fragment (i.e., peptides and polypeptides comprising at least one complementary determining region (CDR)), peptibody, recombinant viral vector, or a nucleic acid. In certain embodiments, a senolytic agent is an antisense oligonucleotide, siRNA, shRNA, or a peptide. For example, senolytic agents such as polypeptides, antibodies, nucleic acids, and the like, include, for example, MDM2 inhibitors, BCL-2 family inhibitors, or Akt kinase inhibitors. In other embodiments, polypeptides, peptides, antibodies (including antigen-binding fragments thereof) that specifically bind to a ligand or target protein of a small molecule senolytic agent described herein, may be used in assays and methods for characterizing or monitoring the use of the small molecule senolytic agent.

The term "sample" generally refers to tissue or organ sample, blood, cell-free blood such as serum and plasma, urine, saliva and cerebrospinal fluid sample.

The term "cell-free" as used herein refers to a sample that lacks any cells to an extent of 90% or more.

In case the original sample is a cell-containing sample, said sample can be subject to cell depletion methods which can be performed as known in the art, thus it can be, but is not limited to pheresis, centrifugation, precipitation, filtration, cell removal by FACS or magnetic activated cell sorting (MACS), chromatography, etc.

As used herein, the term "blood sample" refers to serum, plasma, cell-free blood, whole blood and its components, blood derived products or preparations. Plasma and serum are very useful as shown in the examples. Specifically, the blood sample is a cell-free blood sample.

As used herein, the term "subject" or "individual" or "patient" shall refer to a warm-blooded mammalian, particularly a human being. Alternatively, it may also be an animal, for example mouse, rat, dog, cat, swine, bovine, or a non-human primate.

The term "patient" includes human and other mammalian subjects that receive either prophylactic or therapeutic treatment or are diagnosed of cellular senescence or a senescence-associated disease.

As used therein, the term "pool of subjects" shall refer to a group of healthy individuals and may specifically refer to the samples received from said individuals. The number of individuals of a pool can vary, i.e. it may comprise 2, 3, 4, 5, 6, 7 or more individuals, however it also may be a larger group of subjects, like for example but not limited to 10, 50, 100 or more individuals. According to the embodiment of the invention the pool may also comprise large cohorts of 500 or more individuals.

As used herein, the term "companion diagnostic" shall refer to a diagnostic method, which produces a result that is derived from the analysis of one or more biomarkers as described herein, which is required for the safe and efficacious use of a corresponding drug or medical product.

As used herein, the term "complementary diagnostic" shall refer to a diagnostic method, which produces a result that is derived from the analysis of one or more biomarkers as described herein, which provides significant information regarding the safe and efficacious use of a drug or medical product.

Thus, the method described herein is useful as companion diagnostic and complementary diagnostic tool.

As described herein, the invention specifically provides an in vitro method of detecting senescent cells or diagnosing cellular senescence in a subject, the method comprising quantifying the level of one or more miRNAs selected from the group consisting of miRNAs listed in Table 1 and/or Table 19 or isoforms thereof in a sample from said subject, optionally in combination with any of miRNAs listed in Tables 2 to 15.

As used herein, the term "microRNA" or "miRNA" or "miR" designates a non-coding RNA molecule having a length of about 17 to 25 nucleotides, specifically having a length of 17, 18, 19, 20, 21, 22, 23, 24 or 25 nucleotides which hybridizes to and regulates the expression of a coding messenger RNA.

The term "miRNA molecule" refers to any nucleic acid molecule representing the miRNA, including natural miRNA molecules, i.e. the mature miRNA, pre-miRNA, pri-miRNA.

"miR precursor", "pre-miRNA" or "pre-miR" designates a non-coding RNA having a hairpin structure, which contains a miRNA. A pre-miRNA is the product of cleavage of a primary mi-RNA transcript, or "pri-miR" by the double-stranded RNA-specific ribonuclease (RNAse III) known as Drosha. The precursors may be forms of the respective polynucleotides as they occur during maturation of the respective polynucleotides.

Nucleotide sequences of mature miRNAs and their respective precursors are known in the art and available from the database miRBase or from Sanger database.

Identical polynucleotides as used herein in the context of a polynucleotide to be detected by the method as described herein may have a nucleic acid sequence with an identity of at least 90%, 95%, 97%, 98% or 99% or less than 3 or 2 single nucleotide modifications compared to a polynucleotide comprising or consisting of the nucleotide sequence of any one of SEQ ID Nos. 1-92. In an alternative embodiment, Furthermore, identical polynucleotides as used herein in the context of a polynucleotide to be detected by the method as described herein may have a nucleic acid sequence with an identity of at least 90%, 95%, 97%, 98% or 99% to a polynucleotide comprising or consisting of the nucleotide sequence of any one of SEQ ID Nos. 1-92 including one, two, three or more nucleotides of the corresponding pre-miRNA sequence at the 5"end and/or the 3"end of the respective seed sequence.

All of the specified miRNAs used according to the invention also encompass isoforms and variants thereof.

Although the specified miRNAs listed in Tables 1 to 15 and 19 to 22 are of human origin, the use of corresponding miRNAs from any other sources for the described inventive method shall be encompassed herein. Thus, exemplarily, miRNA miR-34a-5p from any origin is encompassed, wherein hsa-miR-34a-5p is explicitly mentioned in Table 1. The same reads for let-7f-5p, let-7a-5p, miR-143-3p, miR-27a-3p, miR-143-5p, miR-144-5p, miR-3058-3p, miR-30b-5p, miR-339-5p, miR-423-3p, miR-6395, miR-652-3p, miR-18b-5p, miR-92a-3p, miR-10a-3p, miR-151a-5p, miR-191-5p, miR-223-3p, miR-23a-3p, miR-24-3p, miR-29a-3p, miR-20b-5p, miR-93-5p, miR-106a-5p, miR-106b-5p, miR-18a-5p, miR-19a, miR-19b, miR-17-3p, miR-20a-3p, miR-20a-5p, miR-15a-5p, miR-15b-3p, miR-16-5p, miR-16-1-3p, let-7b-5p, let-7c-5p, let-7c-5p, let-7d-5p, let-7d-3p, let-7f, let-7g-3p, let-7i-3p, miR-23a-5p, miR-23b-3p, miR-24-1-5p, miR-27b-3p, miR-29b-3p, miR-29c-3p, miR-30a-3p, miR-30a-5p, miR-30c, miR-30d, miR-30e-3p, miR-34b-5p, miR-34c, miR-34a-3p, miR-34a-5p, miR-146a-5p, miR-146b-5p, miR-376a-3p, miR-376b-3p, miR-376c-3p, miR-663a, miR-663b, miR-181a-3p, miR-181a-5p, miR-181b-5p, miR-181c-5p, miR-21-5p, miR-21-3p, miR-137, miR-766-3p, miR-424-5p, miR-193a-3p, miR-193b-3p, miR-214-3p, miR-155-5p, miR-199b-5p, miR-345-5p, MIR181b-5p, miR-183-3p, miR-215-5p, miR-31-3p, miR-375-5p, miR-409-3p, miR-125a-5p, miR-483-5p, miR-150-5p which can be of any origin.

For the purpose of the invention, the terms "isoforms and variants" (which have also be termed "isomirs") of a reference miRNA include trimming variants (5' trimming variants in which the 5' dicing site is upstream or downstream from the reference miRNA sequence; 3' trimming variants: the 3' dicing site is upstream or downstream from the reference miRNA sequence), or variants having one or more nucleotide modifications (3' nucleotide addition to the 3' end of the reference miRNA; nucleotide substitution by changing nucleotides from the miRNA precursor), or the complementary mature microRNA strand including its isoforms and variants (for example for a given 5' mature microRNA the complementary 3' mature microRNA and vice-versa). With regard to nucleotide modification, the nucleotides relevant for RNA/RNA binding, i.e. the 5'-seed region and nucleotides at the cleavage/anchor side are excluded from modification.

In the following, if not otherwise stated, the term "miRNA" encompasses 3p and 5p strands and also its isoforms and variants.

Specifically, the term "miR-respective number-3p" as used herein in the specification also encompasses its complementary 5p miRNA and vice versa.

In specific embodiments, the miRNAs of interest are detected using a nucleic acid sequence that hybridizes, preferably under stringent conditions, with said miRNA of interest and measuring the hybridization signal.

Circulating microRNAs in cell-free blood such as serum or plasma are a minimal or non-invasive source of biomarkers allowing minimal-invasive detection and therefore a broad applicability in clinics and research repositories. This is especially advantageous for diseases affecting tissues that are not easily accessible for biopsies. Mitchell and others demonstrated that miRNA measurements in serum and plasma collected from the same healthy individuals from the same blood draw are highly correlated (Chen et al. 2008; Mitchell et al. 2008b). However, the choice of anticoagulant (Heparin, EDTA, sodium citrate or Natriumfluorid/potassium oxalat (NaF/KOx)) for plasma sample collection is important, since heparin interferes with enzyme activity in PCR-based assays (Garcia et al. 2002; Boeckel et al. 2013). Similar to heparin, also citrate exhibits an inhibitory effect on qPCR and both are therefore not recommended for miRNA quantitation by qPCR. Unlike heparin, EDTA is removable from the PCR mastermix and is therefore considered the anticoagulant of choice for PCR-based miRNA profiling (Zampetaki & Mayr, 2012). The use of NaF/KOx as anticoagulant resulted in increased miRNA detection rates and may be a suitable alternative if serum or EDTA blood is not at disposition (Kim et al. 2012). The time to centrifugation as well as centrifugation speeds have been shown to critically impact the detection of miRNAs in EDTA plasma samples since it affects the contamination with platelet-derived miRNAs (Cheng et al., 2013). In contrast, miRNA detection in serum was shown to be less sensitive towards pre-processing variations. In view of the state of the art, selecting the appropriate conditions for mi-RNA diagnosis can be done by a skilled person without undue burden.

The term "quantifying" or "quantification" as used herein refers to absolute quantification, i.e. determining the amount of the respective miRNA but also encompasses measuring the level of the respective miRNA and comparing said level with reference or control miRNA. Quantification of the respective miRNA as listed in the tables herein allow expression profiling of senescent cells and thus allow identification of signatures associated with senescence, as well as identification of signatures associated with prognosis and response to treatment. The quantity of miRNAs or difference in miRNA levels can be determined by any of the methods described herein.

In a specific embodiment the level of miRNAs of interest is determined by Next Generation Sequencing. The term "next-generation sequencing (NGS)" refers to the so-called parallelized sequencing by synthesis or sequencing by ligation platforms currently employed by Illumina, Life Technologies, Pacific Biosciences, Oxford Nanopores, and Roche etc. Next-generation sequencing methods may also include nanopore sequencing methods or electronic-detection based methods such as Ion Torrent technology commercialized by Life Technologies.

Specifically, NGS refers to a high-throughput sequencing technology that performs thousands or millions of sequencing reactions in parallel. Although the different NGS platforms use varying assay chemistries, they all generate sequence data from a large number of sequencing reactions running simultaneously on a large number of templates. Typically, the sequence data is collected using a scanner, and then assembled and analyzed bioinformatically. Thus, the sequencing reactions are performed, read, assembled, and analyzed in parallel; see, e.g. Behjati S and Tarpey, P., 2013 (Arch.Di.Child Educ Pract Ed 2013, 98, 236-238); Head S. et al., 2015 (Biotechniques, 56(2), 61-passim).

Some NGS methods require template amplification and some do not. Amplification requiring methods include pyrosequencing (e.g., U.S. Pat. No. 6,258,568; commercialized by Roche); the Solexa/Illumina platform (e.g., U.S. Pat. Nos. 6,833,246, 7,115,400, and 6,969,488); and the Supported Oligonucleotide Ligation and Detection (SOLiD) platform (Applied Biosystems; e.g., U.S. Pat. Nos. 5,912, 148 and 6,130,073). Methods that do not require amplification, e.g., single-molecule sequencing methods, include nanopore sequencing, HeliScope (U.S. Pat. Nos. 7,169,560; 7,282,337; 7,482,120; 7,501,245; 6,818,395; 6,911,345; and 7,501,245); real-time sequencing by synthesis (see, e.g., U.S. Pat. No. 7,329,492); single molecule real time (SMRT) DNA sequencing methods using zero-mode waveguides (ZMWs); and other methods, including those described in U.S. Pat. Nos. 7,170,050; 7,302,146; 7,313,308; and 7,476, 503, US 20130274147; US20140038831; and Metzker, Nat Rev Genet 11(1): 31-46 (2010). Alternatively, hybridization-based sequence methods or other high-throughput methods can also be used, e.g., microarray analysis, NANOSTRING, ILLUMINA, or other sequencing platforms.

In a further specific embodiment, the level of the miRNAs of interest is determined by polymerase chain reaction (PCR). In various embodiments, the nucleic acid is amplified. Any amplification method known in the art may be used. Examples of amplification techniques that can be used include, but are not limited to, PCR, quantitative PCR, quantitative fluorescent PCR (QF-PCR), multiplex fluorescent PCR (MF-PCR), real time PCR (RT-PCR), single cell PCR, restriction fragment length polymorphism PCR (PCR-RFLP), hot start PCR, nested PCR, in situ polony PCR, in situ rolling circle amplification (RCA), bridge PCR, picotiter PCR, and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR), and nucleic acid based sequence amplification (NABSA).

In the PCR methods useful in the present invention, the primers are usually based on the mature miRNA molecule, but may include chemical modifications to optimize hybridization behavior.

qRT-PCR methods may determine an absolute level of expression of a miRNA. Alternatively, qRT-PCR methods may determine the relative quantity of a miRNA. The relative quantity of a miRNA may be determined by normalizing the level of the miRNA to the level of one or more internal standard nucleic acid sequences (reference miRNA values). In general, such internal standard nucleic acid sequences should have a constant level in the analyzed blood or serum sample. For instance, internal standard nucleic acid sequences may be constitutively transcribed RNA nucleic acid sequences such as mRNAs like glyceraldehyde-3-phosphate-dehydrogenase (GAPDH), beta-actin (ACTB), or non-coding RNAs such as 5S and 18S ribosomal RNA, RNU48, RNU44, and RNU6. In addition, synthetic RNA sequences added in an equimolar amount during RNA isolation or cDNA synthesis can be used as references for relative quantification of specific miRNAs.

An overview of real time PCR quantification methods useful in the present invention is given by Schmittgen et al., 2008, Methods. January; 44(1): 31-38.

Primers for detection of miRNAs are commercially available, e.g. as microRNA LNA™ PCR primer sets from Exiqon.

Since miRNAs are relatively short molecules, it may be useful, as suggested, e.g. in WO201114476A, to lengthen them by adding adenosine monomers to the strand (a technique known as polyadenylation) before reverse transcription and amplification. Briefly, the RNA may be extracted from the sample by a suitable reagent (e.g. Trizol reagent), polyadenylated in the presence of ATP and poly(A) polymerase, reverse transcribed into cDNA using a poly(T) adapter and 5' RACE sequence, and amplified using a forward primer derived from the 3' end of the miRNA and a reverse RACE primer. Improvements of this technique include designing the RACE primer with a nucleotide at its 3' end (constituting an A, C, or G, but not a T, so to exclude priming anywhere on the polyA sequence and enforce priming on the miRNA sequence) or RACE primers which are anchored at the 3' cDNA end of a specific microRNA using 2, 3, 4, or more nucleotides with or without chemical modification.

The detection of a miRNA may also be achieved by other methods known in the art, e.g. those described in WO201114476A, like by the deep sequencing method, bead-based quantification, e.g. ILLUMINA™ immobilized oligonucleotide bead arrays, hydrogel-particle based quantification, e.g. FIREFLY™ particle-based flow cytometry assays, by microarray technology, e.g. the NCODE™ human miRNA array available from Invitrogen, chip arrays available from Affymetrix, Agilent, or microarrays which employ LNA-backbone capture probes such as miRCURY LNA™ miRNA PCR assays), e.g., from Exiqon.

The difference in miRNA levels can also be determined using multiplex chemiluminescence-based nucleic acid assays such as Panomics, or reporter plasmid assays ("biosensors") containing reporter proteins with microRNA-complementary regulatory sites, or other hybridization-based techniques known in the art.

Biomarkers are commonly defined as biological molecules found in body fluids, such as blood, or tissues that are signs of a normal or abnormal process, or of a condition or disease. The clinical utility of a biomarker is specifically dependent on its ability to differentiate two or more groups, which frequently include groups of healthy, diseased and treated subjects. The ability of a biomarker to differentiate between two or more groups can be assessed using several methods, most commonly analysis of variance (ANOVA) or receiver-operator characteristic analysis (ROC). ANOVA assess the statistical meaningfulness of the differences in biomarkers levels between three or more groups, where each group consists of at least three independent replicates. A p-value of <0.20 can be considered as a trend demonstrating a putative difference in the biomarker level between groups. A p-value of <0.05 is generally considered to indicate significant changes in biomarker level between groups. ROC analysis is performed to investigate the sensitivity and specificity of a biomarker level for the differentiation of two specific groups, for example healthy and diseased, or diseased and treated, where sensitivity means the probability of getting a positive test result in subjects with the disease, and where specificity means the probability of getting a negative test result in subjects without the disease. The ROC curve depicts the relation between sensitivity and specificity of a biomarker test in relation to a continuously increasing threshold for a positive test result. The discriminatory power of a biomarker is defined by the area under this ROC curve (AUC), where an AUC <0.6 indicates low, in the range of 0.6 to 0.7 medium, in the range of 0.7 to 0.8 good, and >0.8 very good discriminatory power. Furthermore an AUC value of 0.5 indicates random classification power, while an area of 1.0 indicates perfect classification without any errors.

A "control", "control sample", or "reference value" or "reference level" are terms which can be used interchangeably herein, and are to be understood as a sample or standard used for comparison with the experimental sample. The control may include a sample obtained from a healthy subject or a subject, which is not at risk of or suffering from senescence or is not exposed to stress conditions inducing senescence or which is exposed to treatment with a senolytic agent. Reference level specifically refers to the level of miRNA or miRNA expression quantified in a sample from a healthy subject, from a subject, which is not at risk of or suffering from senescence or is not exposed to stress conditions inducing senescence or, in case of senolytic treatment monitoring, said level could also be derived from a sample of a subject before starting senolytic treatment or during the course of senolytic treatment.

Specifically a more than 1.3, 1.4, 1.5, 1.6, 1.7, 1.8, 1.9 or 2.0 fold difference between the reference level of one or more miRNAs as defined herein obtained from a sample of a subject during or after senolytic treatment compared with a sample of the same subject from an earlier time point (intra-individual comparison or intra-individual difference) is indicative of the response to senolytic treatment.

Additionally, a control may also be a standard reference value or range of values, i.e. such as stable expressed miRNAs in the samples, for example the endogenous control U6 snRNA.

The reference level can also be determined as the average level of the corresponding miRNAs in a sample of a healthy subject and/or in a subject prior to a pharmacologic, dietary or life-style intervention. As an alternative, also a pool of samples from one or more subjects may be used or a reference disclosed in literature.

According to the embodiment, a difference by more than one standard deviations of the level comparison is indicative of the presence of senescent cells or cellular senescence.

In a specific embodiment, in addition to the herein described measurement of miRNA levels, the level of one or more proteins secreted by senescent cells is measured and compared to a protein reference level, wherein the magnitude of difference in the protein and miRNA levels when compared to the protein reference level and RNA reference level is indicative of the presence of senescent cells or cellular senescence.

The miRNAs to be quantified by the method described herein are listed in Table 1 below:

TABLE 1

| miRNA species | Sequence | SEQ ID |
|---|---|---|
| hsa-miR-34a-5p | UGGCAGUGUCUUAGCUGGUUGU | SEQ ID No. 1 |
| hsa-let-7f-5p | UGAGGUAGUAGAUUGUAUAGUU | SEQ ID No. 2 |
| hsa-let-7a-5p | UGAGGUAGUAGGUUGUAUAGUU | SEQ ID No. 3 |
| hsa-miR-143-3p | UGAGAUGAAGCACUGUAGCUC | SEQ ID No. 4 |
| hsa-miR-27a-3p | UUCACAGUGGCUAAGUUCCGC | SEQ ID No. 5 |
| hsa-miR-143-5p | GGUGCAGUGCUGCAUCUCUGGU | SEQ ID No. 6 |
| hsa-miR-144-5p | GGAUAUCAUCAUAUACUGUAAG | SEQ ID No. 7 |
| mmu-miR-3058-3p | UUCCUGUCAGCCGUGGGUGCC | SEQ ID No. 8 |
| hsa-miR-30b-5p | UGUAAACAUCCUACACUCAGCU | SEQ ID No. 9 |
| hsa-miR-339-5p | UCCCUGUCCUCCAGGAGCUCACG | SEQ ID No. 10 |
| hsa-miR-423-3p | AGCUCGGUCUGAGGCCCCUCAGU | SEQ ID No. 11 |
| mmu-miR-6395 | CUGGCCCUCUCUGCCCUGUUUA | SEQ ID No. 12 |
| hsa-miR-652-3p | AAUGGCGCCACUAGGGUUGUG | SEQ ID No. 13 |
| hsa-miR-18b-5p | UAAGGUGCAUCUAGUGCAGUUAG | SEQ ID No. 14 |
| hsa-miR-92a-3p | UGGCAGUGUCUUAGCUGGUUGU | SEQ ID No. 15 |

The miRNAs to be quantified by the method described herein are listed in Table 19 below. Specifically the expression levels of miRNAs of Table 19 are correlated with senescence and are significant for detecting senescent cells or determining senescence or stress induced senescence in a sample and/or are correlated with senolytic treatment and are significant for monitoring s senolytic treatment success in a sample.

TABLE 19

| mRNA species | Sequence | SEQ ID |
| --- | --- | --- |
| let-7a-5p | UGAGGUAGUAGGUUGUAUAGUU* | SEQ ID No. 3 |
| let-7b-5p | UGAGGUAGUAGGUUGUGUGGUU* | SEQ ID No. 38 |
| miR-34a-5p | UGGCAGUGUCUUAGCUGGUUGU | SEQ ID No. 1 |
| miR-34a-3p | CAAUCAGCAAGUAUACUGCCCU | SEQ ID No. 59 |
| miR-151-5p | UCGAGGAGCUCACAGUCUAGU | SEQ ID No. 17 |
| miR-155-5p | UUAAUGCUAAUCGUGAUAGGGGU | SEQ ID No. 80 |
| miR-199a-5p | CCCAGUGUUCAGACUACCUGUUC | SEQ ID No. 81 |
| miR-199b-5p | CCCAGUGUUUAGACUAUCUGUUC | SEQ ID No. 82 |
| miR-345-5p | GCUGACUCCUAGUCCAGGGCUC | SEQ ID No. 83 |
| miR-23a-3p | AUCACAUUGCCAGGGAUUUCC | SEQ ID No. 20 |
| miR-23b-3p | AUCACAUUGCCAGGGAUUACC | SEQ ID No. 47 |
| miR-24-3p | UGGCUCAGUUCAGCAGGAACAG | SEQ ID No. 21 |
| miR-27a-3p | UUCACAGUGGCUAAGUUCCGC | SEQ ID No. 5 |
| miR-146a-5p | UGAGAACUGAAUUCCAUGGGUU | SEQ ID No. 61 |
| miR-423-3p | AGCUCGGUCUGAGGCCCCUCAGU | SEQ ID No. 11 |
| miR-181b-5p | AACAUUCAUUGCUGUCGGUGGGU | SEQ ID No. 84 |
| miR-183-3p | GUGAAUUACCGAAGGGCCAUAA | SEQ ID No. 85 |
| mi R-215-5p | AUGACCUAUGAAUUGACAGAC | SEQ ID No. 86 |
| miR-31-5p | AGGCAAGAUGCUGGCAUAGCU | SEQ ID No. 87 |
| miR-375-5p | UUUGUUCGUUCGGCUCGCGUGA | SEQ ID No. 88 |
| miR-409-3p | GAAUGUUGCUCGGUGAACCCCU | SEQ ID No. 89 |
| miR-125a-5p | UCCCUGAGACCCUUUAACCUGUGA | SEQ ID No. 90 |
| miR-483-5p | AAGACGGGAGGAAAGAAGGGAG | SEQ ID No. 91 |
| miR-150-5p | UCUCCCAACCCUUGUACCAGUG | SEQ ID No. 92 |

The miRNAs to be quantified by the method described herein are listed in Table 20 below. Specifically the expression levels of miRNAs of Table 20 are significantly correlated with senescence and are useful for detecting senescent cells or determining senescence or stress induced senescence in a sample.

TABLE 20

| mRNA species | Sequence | SEQ ID |
| --- | --- | --- |
| let-7a-5p | UGAGGUAGUAGGUUGUAUAGUU* | SEQ ID No. 3 |
| let-7b-5p | UGAGGUAGUAGGUUGUGUGGUU* | SEQ ID No. 38 |
| miR-34a-5p | UGGCAGUGUCUUAGCUGGUUGU | SEQ ID No. 1 |
| miR-34a-3p | CAAUCAGCAAGUAUACUGCCCU | SEQ ID No. 59 |
| miR-151-5p | UCGAGGAGCUCACAGUCUAGU | SEQ ID No. 17 |

TABLE 20-continued

| mRNA species | Sequence | SEQ ID |
|---|---|---|
| miR-155-5p | UUAAUGCUAAUCGUGAUAGGGGU | SEQ ID No. 80 |
| miR-199a-5p | CCCAGUGUUCAGACUACCUGUUC | SEQ ID No. 81 |
| miR-199b-5p | CCCAGUGUUUAGACUAUCUGUUC | SEQ ID No. 82 |
| miR-345-5p | GCUGACUCCUAGUCCAGGGCUC | SEQ ID No. 83 |

The miRNAs to be quantified by the method described herein are listed in Table 21 below. Specifically the expression levels of miRNAs of Table 21 are significantly correlated with senolytic treatment and are significant for monitoring senolytic treatment success in a sample.

TABLE 21

| mRNA species | Sequence | SEQ ID |
|---|---|---|
| miR-23a-3p | AUCACAUUGCCAGGGAUUUCC | SEQ ID No. 20 |
| miR-23b-3p | AUCACAUUGCCAGGGAUUACC | SEQ ID No. 47 |
| miR-24-3p | UGGCUCAGUUCAGCAGGAACAG | SEQ ID No. 21 |
| miR-27a-3p | UUCACAGUGGCUAAGUUCCGC | SEQ ID No. 5 |
| miR-146a-5p | UGAGAACUGAAUUCCAUGGGUU | SEQ ID No. 61 |
| miR-423-3p | AGCUCGGUCUGAGGCCCCUCAGU | SEQ ID No. 11 |
| miR-181b-5p | AACAUUCAUUGCUGUCGGUGGGU | SEQ ID No. 84 |
| miR-183-3p | GUGAAUUACCGAAGGGCCAUAA | SEQ ID No. 85 |
| miR-215-5p | AUGACCUAUGAAUUGACAGAC | SEQ ID No. 86 |
| miR-31-5p | AGGCAAGAUGCUGGCAUAGCU | SEQ ID No. 87 |
| miR-375-5p | UUUGUUCGUUCGGCUCGCGUGA | SEQ ID No. 88 |
| miR-409-3p | GAAUGUUGCUCGGUGAACCCCU | SEQ ID No. 89 |
| miR-125a-5p | UCCCUGAGACCCUUUAACCUGUGA | SEQ ID No. 90 |
| miR-483-5p | AAGACGGGAGGAAAGAAGGGAG | SEQ ID No. 91 |
| miR-150-5p | UCUCCCAACCCUUGUACCAGUG | SEQ ID No. 92 |

A panel of selected discriminators of senescence miRNAs to be quantified by the method described herein are listed in Table 22 below. Discriminators encompass miRNAs whose expression is correlated with senescence and with senolytic treatment success.

TABLE 22

| mRNA species | Sequence | SEQ ID |
|---|---|---|
| let-7a-5p | UGAGGUAGUAGGUUGUAUAGUU | SEQ ID No. 3 |
| let-7b-5p | UGAGGUAGUAGGUUGUGUGGUU* | SEQ ID No. 38 |
| miR-199a-5p | CCCAGUGUUCAGACUACCUGUUC | SEQ ID No. 81 |
| miR-199b-5p | CCCAGUGUUUAGACUAUCUGUUC | SEQ ID No. 82 |
| miR-345-5p | GCUGACUCCUAGUCCAGGGCUC | SEQ ID No. 83 |
| miR-423-3p | AGCUCGGUCUGAGGCCCCUCAGU | SEQ ID No. 11 |
| miR-125a-5p | UCCCUGAGACCCUUUAACCUGUGA | SEQ ID No. 90 |

According to a specific embodiment, the level of (i) miR-34a-5p (ii) miR-27a-3p, and (iii) one or more further miRNAs listed in Table 1 is quantified.

According to a further embodiment, the level of one or more further miRNAs selected from the group consisting of miRNAs listed in Table 2 below is quantified.

TABLE 2

| miRNA species | Sequence | SEQ ID No. |
|---|---|---|
| hsa-miR-10a-3p | CAAAUUCGUAUCUAGGGGAAUA | SEQ ID No. 16 |
| hsa-miR-151a-5p | UCGAGGAGCUCACAGUCUAGU | SEQ ID No. 17 |
| hsa-miR-191-5p | CAACGGAAUCCCAAAAGCAGCUG | SEQ ID No. 18 |
| hsa-miR-223-3p | UGUCAGUUUGUCAAAUACCCCA | SEQ ID No. 19 |
| hsa-miR-23a-3p | AUCACAUUGCCAGGGAUUUCC | SEQ ID No. 20 |
| hsa-miR-24-3p | UGGCUCAGUUCAGCAGGAACAG | SEQ ID No. 21 |
| hsa-miR-29a-3p | UAGCACCAUCUGAAAUCGGUUA | SEQ ID No. 22 |
| hsa-miR-20b-5p | CAAAGUGCUCAUAGUGCAGGUAG | SEQ ID No. 23 |
| hsa-miR-93-5p | CAAAGUGCUGUUCGUGCAGGUAG | SEQ ID No. 24 |
| hsa-miR-106a-5p | AAAAGUGCUUACAGUGCAGGUAG | SEQ ID No. 25 |
| hsa-miR-106b-5p | UAAAGUGCUGACAGUGCAGAU | SEQ ID No. 26 |
| hsa-miR-18a-5p | UAAGGUGCAUCUAGUGCAGAUAG | SEQ ID No. 27 |

According to a further embodiment, the level of one or more further miRNAs selected from the group consisting of miRNAs listed in Table 3 below is quantified.

TABLE 3

| miRNA species | Sequence | SEQ ID No. |
|---|---|---|
| hsa-miR-19a | UGUGCAAAUCUAUGCAAAACUGA | SEQ ID No. 28 |
| hsa-miR-19b | UGUGCAAAUCCAUGCAAAACUGA | SEQ ID No. 29 |
| hsa-miR-17-3p | ACUGCAGUGAAGGCACUUGUAG | SEQ ID No. 30 |
| hsa-miR-17-5p | CAAAGUGCUUACAGUGCAGGUAG | SEQ ID No. 31 |
| hsa-miR-20a-3p | ACUGCAUUAUGAGCACUUAAAG | SEQ ID No. 32 |
| hsa-miR-20a-5p | UAAAGUGCUUAUAGUGCAGGUAG | SEQ ID No. 33 |

According to a further embodiment, the level of one or more further miRNAs selected from the group consisting of miRNAs listed in Table 4 below is quantified.

TABLE 4

| miRNA species | Sequence | SEQ ID No. |
|---|---|---|
| hsa-miR-15a-5p | UAGCAGCACAUAAUGGUUUGUG | SEQ ID No. 34 |
| hsa-miR-15b-3p | CAGGCCAUAUUGUGCUGCCUCA | SEQ ID No. 35 |
| hsa-miR-16-5p | UAGCAGCACGUAAAUAUUGGCG | SEQ ID No. 36 |
| hsa-miR-16-1-3p | CCAGUAUUAACUGUGCUGCUGA | SEQ ID No. 37 |

According to a further embodiment, the level of one or more further miRNAs selected from the group consisting of miRNAs listed in Table 5 below is quantified.

TABLE 5

| miRNA species | Sequence | SEQ ID No. |
|---|---|---|
| hsa-let-7b-5p | UGAGGUAGUAGGUUGUGUGGUU | SEQ ID No. 38 |
| hsa-let-7c-5p | UGAGGUAGUAGGUUGUAUGGUU | SEQ ID No. 39 |
| hsa-let-7c-5p | UGAGGUAGUAGGUUGUAUGGUU | SEQ ID No. 40 |
| hsa-let-7d-5p | AGAGGUAGUAGGUUGCAUAGUU | SEQ ID No. 41 |
| hsa-let-7d-3p | CUAUACGACCUGCUGCCUUUCU | SEQ ID No. 42 |
| hsa-let-7f | UGAGGUAGUAGAUUGUAUAGUU | SEQ ID No. 43 |
| hsa-let-7g-3p | CUGUACAGGCCACUGCCUUGC | SEQ ID No. 44 |
| hsa-let-7i-3p | CUGCGCAAGCUACUGCCUUGCU | SEQ ID No. 45 |

According to a further embodiment, the level of one or more further miRNAs selected from the group consisting of miRNAs listed in Table 6 below is quantified.

TABLE 6

| miRNA species | Sequence | SEQ ID No. |
|---|---|---|
| hsa-miR-23a-5p | GGGGUUCCUGGGGAUGGGAUUU | SEQ ID No. 46 |
| hsa-miR-23b-3p | AUCACAUUGCCAGGGAUUACC | SEQ ID No. 47 |
| hsa-miR-24-1-5p | UGCCUACUGAGCUGAUAUCAGU | SEQ ID No. 48 |
| hsa-miR-27b-3p | UUCACAGUGGCUAAGUUCUGC | SEQ ID No. 49 |

According to a further embodiment, the level of one or more further miRNAs selected from the group consisting of miRNAs listed in Table 7 below is quantified.

TABLE 7

| miRNA species | Sequence | SEQ ID No. |
|---|---|---|
| hsa-miR-29b-3p | UAGCACCAUUUGAAAUCAGUGUU | SEQ ID No. 50 |
| hsa-miR-29c-3p | UAGCACCAUUUGAAAUCGGUUA | SEQ ID No. 51 |

According to a further embodiment, the level of one or more further miRNAs selected from the group consisting of miRNAs listed in Table 8 below is quantified.

TABLE 8

| miRNA species | Sequence | SEQ ID No. |
|---|---|---|
| hsa-miR-30a-3p | CUUUCAGUCGGAUGUUUGCAGC | SEQ ID No. 52 |
| hsa-miR-30a-5p | UGUAAACAUCCUCGACUGGAAG | SEQ ID No. 53 |
| hsa-miR-30c | UGUAAACAUCCUACACUCUCAGC | SEQ ID No. 54 |
| hsa-miR-30d | UGUAAACAUCCCCGACUGGAAG | SEQ ID No. 55 |
| hsa-miR-30e-3p | CUUUCAGUCGGAUGUUUACAGC | SEQ ID No. 56 |

According to a further embodiment, the level of one or more further miRNAs selected from the group consisting of miRNAs listed in Table 9 below is quantified.

TABLE 9

| miRNA species | Sequence | SEQ ID No. |
|---|---|---|
| hsa-miR-34b-5p | UAGGCAGUGUCAUUAGCUGAUUG | SEQ ID No. 57 |
| hsa-miR-34c | AGGCAGUGUAGUUAGCUGAUUGC | SEQ ID No. 58 |
| hsa-miR-34a-3p | CAAUCAGCAAGUAUACUGCCCU | SEQ ID No. 59 |
| hsa-miR-34a-5p | UGGCAGUGUCUUAGCUGGUUGU | SEQ ID No. 60 |

According to a further embodiment, the level of one or more further miRNAs selected from the group consisting of miRNAs listed in Table 10 below is quantified.

TABLE 10

| miRNA species | Sequence | SEQ ID No. |
|---|---|---|
| hsa-miR-146a-5p | UGAGAACUGAAUUCCAUGGGUU | SEQ ID No. 61 |
| hsa-miR-146b-5p | UGAGAACUGAAUUCCAUAGGCU | SEQ ID No. 62 |

According to a further embodiment, the level of one or more further miRNAs selected from the group consisting of miRNAs listed in Table 11 below is quantified.

TABLE 11

| miRNA species | Sequence | SEQ ID No. |
|---|---|---|
| hsa-miR-376a-3p | AUCAUAGAGGAAAAUCCACGU | SEQ ID No. 63 |
| hsa-miR-376b-3p | AUCAUAGAGGAAAAUCCAUGUU | SEQ ID No. 64 |
| hsa-miR-376c-3p | AACAUAGAGGAAAUUCCACGU | SEQ ID No. 65 |

According to a further embodiment, the level of one or more further miRNAs selected from the group consisting of miRNAs listed in Table 12 below is quantified.

TABLE 12

| miRNA species | Sequence | SEQ ID No. |
|---|---|---|
| hsa-miR-663a | AGGCGGGGCGCCGCGGGACCGC | SEQ ID No. 66 |
| hsa-miR-663b | GGUGGCCCGGCCGUGCCUGAGG | SEQ ID No. 67 |

According to a further embodiment, the level of one or more further miRNAs selected from the group consisting of miRNAs listed in Table 13 below is quantified.

TABLE 13

| miRNA species | Sequence | SEQ ID No. |
|---|---|---|
| hsa-miR-181a-3p | ACCAUCGACCGUUGAUUGUACC | SEQ ID No. 68 |
| hsa-miR-181a-5p | AACAUUCAACGCUGUCGGUGAGU | SEQ ID No. 69 |
| hsa-miR-181b-5p | AACAUUCAUUGCUGUCGGUGGGU | SEQ ID No. 70 |
| hsa-miR-181c-5p | AACAUUCAACCUGUCGGUGAGU | SEQ ID No. 71 |

According to a further embodiment, the level of one or more further miRNAs selected from the group consisting of miRNAs listed in Table 14 below is quantified.

TABLE 14

| miRNA species | Sequence | SEQ ID No. |
|---|---|---|
| hsa-miR-21-5p | UAGCUUAUCAGACUGAUGUUGA | SEQ ID No. 72 |
| hsa-miR-21-3p | CAACACCAGUCGAUGGGCUGU | SEQ ID No. 73 |

According to a further embodiment, the level of one or more further miRNAs selected from the group consisting of miRNAs listed in Table 15 below is quantified.

TABLE 15

| miRNA species | Sequence | SEQ ID No. |
|---|---|---|
| hsa-miR-137 | UUAUUGCUUAAGAAUACGCGUAG | SEQ ID No. 74 |
| hsa-miR-766-3p | ACUCCAGCCCCACAGCCUCAGC | SEQ ID No. 75 |
| hsa-miR-424-5p | CAGCAGCAAUUCAUGUUUUGAA | SEQ ID No. 76 |
| hsa-miR-193a-3p | AACUGGCCUACAAAGUCCCAGU | SEQ ID No. 77 |
| hsa-miR-193b-3p | AACUGGCCCUCAAAGUCCCGCU | SEQ ID No. 78 |
| hsa-miR-214-3p | ACAGCAGGCACAGACAGGCAGU | SEQ ID No. 79 |
| hsa-miR-155-5p | UUAAUGCUAAUCGUGAUAGGGGU | SEQ ID No. 80 |

According to a specific embodiment, the level of one or more miRNAs from Table 1 is quantified in combination with one or more different miRNAs from any of Tables 2 to 15.

Specifically, the level of miR-34a-5p and/or miR-27a-3p is quantified in combination with one or more different miRNAs from Tables 2 to 15, e.g. miR-93-5p, miR-19a, miR-17, miR-23a-5p, miR-30a-3p, or miR-376a.

Specifically, the level of miR-137, miR-766-3p and/or miR-424-5p is quantified in combination with one or more different miRNAs from any of Tables 2 to 15.

According to a further specific embodiment, the level of one or more miRNAs from Table 1 or Table 19 is quantified in combination with two or more miRNAs from at least 2, 3, 4, 5, 6, 7, 8, 9, 10, 11, 12, 13, 14, 15, 16, 17, or 18 different groups listed in any one of Tables 2 to 15 and Tables 19 to 22.

Specifically, the level of miR-34a-5p and/or miR-27a-3p is quantified in combination with two or more miRNAs from at least 2, 3, 4, 5, 6, 7, 8, 9, 10, 11, 12, 13 or 14 different miRNAs listed in any one of Tables 2 to 15.

Specifically, miRNAs let-7a-5p, let-7b-5p, miR-199a-5p, miR-345-5p, miR-423-3p, and miR-125a-5p are quantified according to the method described herein. Specifically, let-7a-5p is quantified in combination with 1, 2, 3, 4, 5, 6, 7, 8, or all of let-7b-5p, miR-199a-5p, miR-345-5p, miR-423-3p, and miR-125a-5p. Specifically let-7b-5p is quantified in combination with 1, 2, 3, 4, 5, or all of let-7a-5p, miR-199a-5p, miR-345-5p, miR-423-3p, and miR-125a-5p. Specifically miR-199a-5p is is quantified in combination with 1, 2, 3, 4, 5, or all of let-7a-5p, let-7b-5p, miR-345-5p, miR-423-3p, and miR-125a-5p. Specifically miR-345-5p is quantified in combination with 1, 2, 3, 4, 5, or all of let-7a-5p, let-7b-5p, miR-199a-5p, miR-423-3p, and miR-125a-5p. Specifically miR-423-3p is quantified in combination with 1, 2, 3, 4, 5, or all of let-7a-5p, let-7b-5p, miR-199a-5p, miR-345-5p, and miR-125a-5p. Specifically miR-125a-5p is quantified in combination with 1, 2, 3, 4, 5, or all of let-7a-5p, let-7b-5p, miR-199a-5p, miR-345-5p, and miR-423-3p. Said miRNAs can also be quantified in combination with one or more of miRNAs of Table 20 or 21.

Specifically, miRNAs let-7a-5p, let-7b-5p, miR-34a-5p, miR-34a-3p, miR-151-5p, miR-155-5p, miR-199a-5p, miR-199b-5p and miR-345-5p are quantified according to the method described herein. Specifically let-7a-5p is quantified in combination with 1, 2, 3,4, 5, 6, 7, or all of let-7b-5p, miR-34a-5p, miR-34a-3p, miR-151-5p, miR-155-5p, miR-199a-5p, miR-199b-5p and miR-345-5p. Specifically let-7b-5p is quantified in combination with 1, 2, 3, 4, 5, 6, 7, or all of let-7a-5p, miR-34a-5p, miR-34a-3p, miR-151-5p, miR-155-5p, miR-199a-5p, miR-199b-5p and miR-345-5p. Specifically miR-34a-5p is quantified in combination with 1, 2, 3, 4, 5, 6, 7, or all of let 7a-5p, let-7b-5p, miR-34a-5p, miR-34a-3p, miR-151-5p, miR-155-5p, miR-199a-5p, miR-199b-5p and miR-345-5p. Specifically miR-34a-3p is quantified in combination with 1, 2, 3, 4, 5, 6, 7, or all of let 7a-5p, let-7b-5p, miR-34a-5p, miR-151-5p, miR-155-5p, miR-199a-5p, miR-199b-5p and miR-345-5p. Specifically miR-151-5p is quantified in combination with 1, 2, 3, 4, 5, 6, 7, or all of let 7a-5p, let-7b-5p, miR-34a-5p, miR-34a-3p, miR-155-5p, miR-199a-5p, miR-199b-5p and miR-345-5p. Specifically miR-155-5p is quantified in combination with 1, 2, 3, 4, 5, 6, 7, or all of let 7a-5p, let-7b-5p, miR-34a-5p, miR-34a-3-p, miR-151-5p, miR-199a-5p, miR-199b-5p and miR-345-5p. Specifically miR-199a-5p is quantified in combination with 1, 2, 3, 4, 5, 6, 7, or all of let 7a-5p, let-7b-5p, miR-34a-5p, miR-34a-3p, miR-151-5p, miR-155-5p, miR-199b-5p and miR-345-5p. Specifically miR-199b-5p is quantified in combination with 1, 2, 3, 4, 5, 6, 7, or all of let 7a-5p, let-7b-5p, miR-34a-5p, miR-34a-3p, miR-151-5p, miR-155-5p, miR-199a-5p, and miR-345-5p. Specifically miR-345-5p is quantified in combination with 1, 2, 3, 4, 5, 6, 7, or all of let 7a-5p, let-7b-5p, miR-34a-5p, miR-34a-3p, miR-151-5p, miR-155-5p, miR-199a-5p and miR-199b-5p. Said miRNAs can also be quantified in combination with one or more of miRNAs of Table 21 or 22.

Specifically, miR-23a-3p, miR-23b-3p, miR-24-3p, miR-27a-3p, and miR-146a-5p, miR-423-3p, miR-181b-5p, miR- 183-3p, miR-215-5p, miR-31-5p, miR-375-5p, miR-409-3p, miR-125a-5p, miR-483-5p, and miR-150-5p are quantified according to the method described herein. Specifically miR-23a-3p is quantified in combination with 1, 2, 3, 4, 5, 6, 7, 8, 9, 10, 11, 12, 13, or all of miR-23b-3p, miR-24-3p, miR-27a-3p, and miR-146a-5p, miR-423-3p, miR-181b-5p, miR-183-3p, miR-215-5p, miR-31-5p, miR-375-5p, miR-409-3p, miR-125a-5p, miR-483-5p, and miR-150-5p. Specifically miR-23b-3p is quantified in combination with 1, 2, 3, 4, 5, 6, 7, 8, 9, 10, 11, 12, 13, or all of miR-23a-3p, miR-24-3p, miR-27a-3p, miR-146a-5p, miR-423-3p, miR-181b-5p, miR-183-3p, miR-215-5p, miR-31-5p, miR-375-5p, miR-409-3p, miR-125a-5p, miR-483-5p, and miR-150-5p. Specifically miR-24-3p is quantified in combination with 1, 2, 3, 4, 5, 6, 7, 8, 9, 10, 11, 12, 13, or all of miR-23a-3p, miR-23b-3p, miR-27a-3p, miR-146a-5p, miR-423-3p, miR-181b-5p, miR-183-3p, miR-215-5p, miR-31-5p, miR-375-5p, miR-409-3p, miR-125a-5p, miR-483-5p, and miR-150-5p. Specifically miR-27a-3p is quantified in combination with 1, 2, 3, 4, 5, 6, 7, 8, 9, 10, 11, 12, 13, or all of miR-23a-3p, miR-23b-3p, miR-24-3p, miR-146a-5p, miR-423-3p, miR-181b-5p, miR-183-3p, miR-215-5p, miR-31-5p, miR-375-5p, miR-409-3p, miR-125a-5p, miR-483-5p, and miR-150-5p. Specifically miR-146a-5p is quantified in combination with 1, 2, 3, 4, 5, 6, 7, 8, 9, 10, 11, 12, 13 or all of miR-23a-3p, miR-23b-3p, miR-24-3p, miR-27a-3p, miR-423-3p, miR-181b-5p, miR-183-3p, miR-215-5p, miR-31-5p, miR-375-5p, miR-409-3p, miR-125a-5p, miR-483-5p, and miR-150-5p. Specifically miR-423-3p is quantified in combination with 1, 2, 3, 4, 5, 6, 7, 8, 9, 10, 11, 12, 13 or all of miR-23a-3p, miR-23b-3p, miR-24-3p, miR-27a-3p, miR-146a-5p, miR-181b-5p, miR-183-3p, miR-215-5p, miR-31-5p, miR-375-5p, miR-409-3p, miR-125a-5p, miR-483-5p, and miR-150-5p. Specifically miR-181b-5p is quantified in combination with 1, 2, 3, 4, 5, 6, 7, 8, 9, 10, 11, 12, 13 or all of miR-23a-3p, miR-23b-3p, miR-24-3p, miR-27a-3p, and miR-146a-5p, miR-423-3p, miR-183-3p, miR-215-5p, miR-31-5p, miR-375-5p, miR-409-3p, miR-125a-5p, miR-483-5p, and miR-150-5p. Specifically miR-183-3p is quantified in combination with 1, 2, 3, 4, 5, 6, 7, 8, 9, 10, 11, 12, 13 or all of miR-23a-3p, miR-23b-3p, miR-24-3p, miR-27a-3p, miR-146a-5p, miR-423-3p, miR-181b-5p, miR-215-5p, miR-31-5p, miR-375-5p, miR-409-3p, miR-125a-5p, miR-483-5p, and miR-150-5p. Specifically miR-215-5p is quantified in combination with 1, 2, 3, 4, 5, 6, 7, 8, 9, 10, 11, 12, 13 or all of miR-23a-3p, miR-23b-3p, miR-24-3p, miR-27a-3p, miR-146a-5p, miR-423-3p, miR-181b-5p, miR-183-3p, miR-31-5p, miR-375-5p, miR-409-3p, miR-125a-5p, miR-483-5p, and miR-150-5p. Specifically miR-31-5p is quantified in combination with 1, 2, 3, 4, 5, 6, 7, 8, 9, 10, 11, 12, 13 or all of miR-23a-3p, miR-23b-3p, miR-24-3p, miR-27a-3p, miR-146a-5p, miR-423-3p, miR-181b-5p, miR-183-3p, miR-215-5p, miR-375-5p, miR-409-3p, miR-125a-5p, miR-483-5p, and miR-150-5p. Specifically miR-375-5p is quantified in combination with 1, 2, 3, 4, 5, 6, 7, 8, 9, 10, 11, 12, 13, or all of miR-23a-3p, miR-23b-3p, miR-24-3p, miR-27a-3p, miR-146a-5p, miR-423-3p, miR-181b-5p, miR-183-3p, miR-215-5p, miR-31-5p, miR-409-3p, miR-125a-5p, miR-483-5p, and miR-150-5p. Specifically miR-409-3p is quantified in combination with 1, 2, 3, 4, 5, 6, 7, 8, 9, 10, 11, 12, 13 or all of miR-23a-3p, miR-23b-3p, miR-24-3p, miR-27a-3p, miR-146a-5p, miR-423-3p, miR-181b-5p, miR-183-3p, miR-215-5p, miR-31-5p, miR-375-5p, miR-125a-5p, miR-483-5p, and miR-150-5p. Specifically miR-125a-5p is quantified in combination with 1, 2, 3, 4, 5, 6, 7, 8, 9, 10, 11, 12, 13 or all of miR-23a-3p, miR-23b-3p, miR-24-3p, miR-27a-3p, miR-146a-5p, miR-423-3p, miR-181b-5p, miR-183-3p, miR-215-5p, miR-31-5p, miR-375-5p, miR-409-3p, miR-483-5p, and miR-150-5p. Specifically miR-483-5p is quantified in combination with 1, 2, 3, 4, 5, 6, 7, 8, 9, 10, 11, 12, 13 or all of miR-23a-3p, miR-23b-3p, miR-24-3p, miR-27a-3p, miR-146a-5p, miR-423-3p, miR-181b-5p, miR-183-3p, miR-215-5p, miR-31-5p, miR-375-5p, miR-409-3p, miR-125a-5p, and miR-150-5p. Specifically miR-150-5p is quantified in combination with 1, 2, 3, 4, 5, 6, 7, 8, 9, 10, 11, 12, 13 or all of miR-23a-3p, miR-23b-3p, miR-24-3p, miR-27a-3p, miR-146a-5p, miR-423-3p, miR-181b-5p, miR-183-3p, miR-215-5p, miR-31-5p, miR-375-5p, miR-409-3p, miR-125a-5p, and miR-483-5p. Said miRNAs can also be quantified in combination with one or more of miRNAs of Table 20 or 22.

Specifically, the level of at 2, 3, 4, 5, 6, 7, 8, 9, 10, 11, 12, 13, 14, 15, 16, 17, 18, 19, 20, 21, 22, 23, 24, 25, 26, 27, 28, 29, 30 or more miRNAs or a quantified.

The present invention specifically provides a set of miRNAs that represent a diagnostic signature or expression pattern applicable both over a broad range of senescence of various cell types including but not limited to fibroblasts, endothelial cells, kidney epithelial cells, liver cells, neuronal cells, skin cells, lung epithelial cells, or colon epithelial cells. In particular, detection of miRNAs, which are differentially regulated in the blood or serum of young subjects or subjects not being exposed to senescence inducing stress conditions and old subjects or subjects being exposed to senescence inducing stress conditions provides a diagnostic and predictive tool that has a higher significance for early diagnosis, long-term prognosis, and screening of patients with cellular senescence. The method as described herein also provides diagnostic tool for monitoring treatment with senolytic agents.

The method of detecting senescent cells or diagnosing cellular senescence in a subject can be specifically used for determining the presence of senescent cells in context of diagnosing senescence-related diseases or diagnosing the risk of senescence-related diseases in a subject.

The senescent cell-associated condition can be a cardiovascular condition, including but not limited to angina, arrhythmia, atherosclerosis, cardiomyopathy, congestive heart failure, coronary artery disease (CAD), carotid artery disease, endocarditis, coronary thrombosis, carotid thrombosis, myocardial infarction (MI), high blood pressure/hypertension, aortic aneurysm, brain aneurysm, cardiac fibrosis, cardiac diastolic dysfunction, hypercholesterolemia/hyperlipidemia, mitral valve prolapse, peripheral vascular disease, peripheral artery disease (PAD), cardiac stress resistance, and stroke.

The senescent cell-associated condition can be a neurological condition. Neurological conditions include, but are not limited to, Parkinson's disease, Alzheimer's disease, dementia, amyotrophic lateral sclerosis (ALS), bulbar palsy, pseudobulbar palsy, primary lateral sclerosis, motor neuron dysfunction (MND), mild cognitive impairment (MCI), Huntington's disease, ocular diseases, macular degeneration (wet and dry), glaucoma, vision loss, presbyopia, cataracts, progressive muscular atrophy, lower motor neuron disease, spinal muscular atrophy (SMA), Werdnig-Hoffman Disease (SMA1), SMA2, Kugelberg-Welander Disease (SM3), Kennedy's disease, post-polio syndrome, hereditary spastic paraplegia, age-related memory decline, and depression and mood disorders.

The senescent cell-associated condition can be an inflammatory condition. Inflammatory conditions include, but are not limited to, musculoskeletal diseases, osteoarthritis, osteoporosis, sarcopenia, lupus, interstitial cystitis, scleroderma, alopecia, oral mucositis, rheumatoid arthritis, inflammatory bowel disease, kyphosis, herniated intervertebral disc, ulcerative colitis, Crohn's disease, ulcerative asthma, renal fibrosis including post-transplant renal fibrosis, liver fibrosis, pancreatic fibrosis, cardiac fibrosis, skin wound healing including diabetes related wound healing, and oral submucosa fibrosis.

The senescent cell-associated condition can be a macular degeneration, dry (non-neovascular) or wet (neovascular) macular degeneration.

The senescent cell-associated condition can be a pulmonary condition. Pulmonary conditions include, but are not limited to, idiopathic pulmonary fibrosis (TPF), chronic obstructive pulmonary disease (COPD), asthma, cystic fibrosis, bronchiectasis, emphysema, age-related loss of pulmonary function, and age-associated sleep apnea.

The senescent cell-associated condition can be a dermatological condition. Dermatological conditions include, but are not limited to, psoriasis, eczema, rhytides, pruritus, dysesthesia, papulosquamous disorders, erythroderma, lichen planus, lichenoid dermatosis, atopic dermatitis, eczematous eruptions, eosinophilic dermatosis, rashes, photosensitivity and photoaging related diseases and disorders, reactive neutrophilic dermatosis, pemphigus, pemphigoid, immunobullous dermatosis, fibrohistocytic proliferations of skin, skin nevi, urticaria, hyperpigmentation, cutaneous lymphomas, psoriasis, and cutaneous lupus.

The embodiment of the invention also encompasses the use of the method described herein for predicting transplant organ function or predicting organ transplant failure.

The method of the invention can be performed as single measurement but may also be performed by repetitive determinations.

The herein described method can also be used for detecting a decline of senescent cells or reduction of cellular senescence, wherein the level of said miRNAs is compared with the level of corresponding miRNAs prior to a treatment with senolytics, anti-aging agents or any anti-aging intervention. Specifically, the signature can indicate the removal of senescent cells e.g. during use of senolytics, anti-aging agents (e.g. rapamycin, spermidine, metformin), or any other anti-aging intervention like diet, exercise, etc. This signature can also be used to identify subjects that would benefit from any senolytic intervention.

Specifically, the method is useful for monitoring a subject, specifically for measuring the response of a subject to senolytic treatments. Therefore, the expression signature may be also used for indication of efficient drug doses (dose finding, e.g. during development of any type of intervention, or in terms of identifying personalized treatment options or dosing).

The method described herein can be used for monitoring therapies and treatment success, or monitoring exposure to senescence inducing agents (intoxicants, including oxidative stressors, DNA damaging agents, etc.).

The signature of miRNAs according to the tables included herein can indicate the presence of senescent cells in any mammalian species in e.g. aging, age-associated diseases, progeroid syndromes, during chemotherapy, intoxications, or any other treatment/accident that increases the amount of senescent cells.

Further items are encompassed herein:

1. An in vitro method of detecting senescent cells, diagnosing cellular senescence and/or monitoring senolytic treatment success in a subject, the method comprising the steps of:
   a) providing a cell-free sample from said subject,
   b) quantifying the level of one or more miRNAs selected from the group consisting of miRNAs listed in Table 1 or isoforms thereof in said sample, and
   c) optionally comparing the level of b) with the reference level of said one or more miRNAs in a reference sample, wherein a difference between said levels is indicative of the presence of senescent cells or cellular senescence.

2. The method of item 1, wherein the level of (i) miR-34a-5p (ii) miR-27a-3p, and (iii) one or more further miRNAs listed in Table 1 is quantified.

3. An in vitro method of detecting senescent cells, diagnosing cellular senescence and/or monitoring senolytic treatment success in a subject, the method comprising the steps of:
   a) providing a cell-free sample from said subject,
   b) quantifying the level of one or more miRNAs selected from the group consisting of miRNAs listed in Table 19 or isoforms thereof in said sample, and
   c) optionally comparing the level of b) with the reference level of said one or more miRNAs in a reference sample wherein a difference between said levels is indicative of the presence of senescent cells or cellular senescence.

4. The method of item 3, wherein the level of one or more of miRNAs selected from the group consisting of let-7a-5p, let-7b-5p, miR-199a-5p, miR-345-5p, miR-423-3p, and miR-125a-5p is quantified.

5. The method of items 3 or 4 for detecting senescent cells or diagnosing cellular senescence, wherein the level of one or more miRNAs selected from the group consisting of let-7a-5p, let-7b-5p, miR-34a-5p, miR-34a-3p, miR-151-5p, miR-155-5p, miR-199a-5p, miR-199b-5p and miR-345-5p is quantified.

6. The method of items 3 or 4 for monitoring senolytic treatment, wherein the level of one or more miRNAs selected from the group consisting of miR-23a-3p, miR-23b-3p, miR-24-3p, miR-27a-3p, miR-146a-5p, miR-423-3p, miR-181b-5p, miR-183-3p, miR-215-5p, miR-31-5p, miR-375-5p, miR-409-3p, miR-125a-5p, miR-483-5p, and miR-150-5p is quantified.

7. The method of any one of items 1 to 6, wherein the level of one or more further miRNAs selected from the group consisting of miRNAs listed in Table 2 is quantified.

8. The method of any one of items 1 to 7, wherein the level of one or more further miRNAs selected from the group consisting of miRNAs listed in any one of Tables 3 to 15 is quantified.

9. The method of any one of items 1 to 8, wherein the level of two or more miRNAs from at least 2, 3, 4, 5, 6, 7, 8, 9, 10 and up to 15 different groups listed in any one of Tables 2 to 15 and 19 to 22 is quantified.

10. The method of any one of items 1 to 9, wherein the level of 2, 3, 4, 5, 6, 7, 8, 9, 10, 11, 12, 13,14, 15, 16, 17, 18, 19, 20, 21, 22, 23, 24 or more miRNAs is quantified.

11. The method according to any one of items 1 to 10, wherein the reference level is the level of the corresponding one or more miRNAs in a sample of a healthy subject or of a subject to a pharmacologic, dietary or life-style intervention or a group thereof.

12. The method according to any one of items 1 to 11, wherein a difference by more than one standard deviations of the level comparison is indicative of the presence of senescent cells or cellular senescence.

13. The method for monitoring senolytic treatment response in a subject according to any one of items 1 to 11, comprising the steps a) providing a cell-free sample from said subject,
b) quantifying the level of one or more miRNAs selected from the group consisting of miRNAs listed in Tables 1, 19 or 21 or isoforms thereof in said sample, and
c) comparing the level of b) with the reference level of said one or more miRNAs in an earlier sample from said subject, wherein a more than 1.5 fold difference between said levels is indicative of the response to senolytic treatment.

14. The method of any one of items 1 to 13, wherein the miRNA levels are determined by quantitative or digital PCR, sequencing, microarray, LUMINEX™M bead-based immunoassay for the detection of analytes, or other hybridization-based techniques.

15. The method of any one of items 1 to 14, wherein the subject is at least 30, 40, 50, 60, 70, 80 or 90 years of age, specifically is a subject at risk of an age-associated disease and/or at risk of SASP.

16. The method of any one of items 1 to 15, wherein the sample is a blood sample, specifically a cell-free blood sample.

17. The method of any one of items 1 to 16 for detecting a decline of senescent cells or reduction of cellular senescence, wherein the level of said miRNAs is compared with the level of corresponding miRNAs prior to a treatment with senolytics, anti-aging agents or any anti-aging intervention.

18. The method of any one of items 1 to 17, wherein further the level of one or more proteins secreted by senescent cells is measured and compared to a protein reference level, wherein the magnitude of difference in said protein level when compared to the protein reference level is indicative of the presence of senescent cells or cellular senescence.

19. A diagnostic device comprising a panel of miRNAs for detecting senescent cells, diagnosing cellular senescence and/or monitoring senolytic treatment success comprising miRNAs let-7a-5p, let-7b-5p, miR-199a-5p, miR-345-5p, miR-423-3p, miR-125a-5p and optionally further comprising one or more of the miRNAs listed in Tables 19, 20 and/or 21.

20. A diagnostic device comprising a panel of miRNAs for detecting senescent cells, diagnosing cellular senescence and/or monitoring senolytic treatment success comprising one or more of the miRNAs listed in Tables 19, 20 and/or 21.

The examples which follow are set forth to aid in the understanding of the invention but are not intended to, and should not be construed to limit the scope of the invention in any way. The examples do not include detailed descriptions of conventional methods. Such methods are well known to those of ordinary skill in the art.

EXAMPLES

The inventors identified secreted miRNAs as part of the SASP and therefore hypothesised that cell-free blood-derived, circulating miRNAs might be the basis of a non-invasive, specific biomarker of senescent cell removal. In order to identify such a biomarker, they used the p16-3MR mouse (Demaria et al, 2014, Developmental Cell 31:722-733), induced senescence as well as senescent cell removal and isolated small RNAs out of the serum for next generation sequencing (see example 1) as well as reverse-transcription quantitative PCR (RT-qPCR, see example 2) analysis.

Indeed, they identified several miRNAs, including miR-34a-5p, which is well known to be upregulated in mouse and human cell senescence, as differentially circulating after induction and subsequent removal of senescent cells.

Their data suggest that circulating miRNAs might be valuable tools to estimate the level of senescent cell presence, to monitor senescent cell killing and thus to be an indispensable tool for the translation of senolytic substances to the clinics. In addition, these miRNAs could be used as therapeutic targets, whenever SASP factors need to be inactivated.

Example 1

1. Materials and methods
1.1. Mouse Work and Serum Sampling
p16-3MR (Demaria et al, 2014, Developmental Cell 31:722-733) mice were bred in house and maintained in the AALAC-accredited Buck Institute for Research on Aging (Novato, Calif.) animal facility. 10 to 12-week-old p16-3MR male mice were used for experiments. Mice were divided in 4 groups and each group consisted of 3 animals. In group A, control mice were injected with PBS. In group B, mice were treated with Ganciclovir (GCV) (Sigma-Aldrich) dissolved in PBS for 5 consecutive days. In group C, mice were treated with one dose of Doxorubicine hydrochloride (Sigma-Aldrich) dissolved in PBS. In group D, mice were first treated with Doxorubicine and then treated 10 days later with GCV. Mice were intraperitoneally injected with one dose of 10 mg/kg of Doxorubicine hydrochloride, and GCV was administered daily by intraperitoneal injections for 5 consecutive days at concentration of 25 mg/kg in PBS. 4 days after the last GCV dose, animals were euthanized with $CO_2$ and blood was withdrawn immediately. Blood was then incubated for 30 min at room temperature and centrifuged at 3400×g for 10 min. Serum was carefully collected in a sterile tube without disturbing the cell pellet and stored at −80° C. for further experiments.

1.2. Next Generation Sequencing
Total RNA extraction was performed from 200 μl of serum using the Qiagen miRNeasy™ extraction kit (Qiagen, Germany). RNA yield was quality checked for homogenous extraction efficiency and hemolysis on the basis qPCR amplification of spiked-in as well as hemolysis-responsive RNAs (Blondal et al). In total 2 μl total RNA were used for library preparation using the CleanTag library preparation protocol (Trilink Biotechnologies, USA), which uses chemically modified adapters to prevent adapter self-ligation. Library quality and yield was controlled using Bioanalyzer DNA-1000 chips. Due to the high purity, libraries were not purified prior to sequencing on an ILLUMINA™ NextSeq 500 sequencing system with 50 bp single-end reads.

1.3. Bioinformatics
Next-generation sequencing was performed at Exiqon (Denmark). Raw reads were quality filtered for a Q-score of 30 or higher. Adapter sequences were trimmed and the remaining reads were mapped against the mouse genome, miRBase, non-coding RNA databases and classified as either microRNAs, small RNAs, genome mapping RNAs or outmapped RNA sequences. Read counts were added for all microRNA isoforms (isomiRs) and normalized by dividing the microRNA read count by the total number of mapped reads and multiplying by 1 million (Tags Per Million). Tags per millions were used for data mining (PCA and hierarchical clustering) using the web-tool clustvis (Metsalu and Vilo 2015).

For differential expression analysis, the EdgeR statistical software package was used. For normalization, the trimmed mean of M-values method was used based on log-fold and absolute gene wise changes in expression levels between samples (TMM normalization). This normalization is primarily compensates for sample specific effects (generally caused by the variation in sequencing depth between samples). Additionally, the normalization step offsets undersampling effects (due to highly expressed microRNAs dominating the read set) by identifying scaling factors that minimize log-fold changes between samples across the majority of microRNAs. MicroRNAs with a p-value of <0.05 were considered significantly regulated.

2. Results 2.1. Characterization of

In order to identify differentially circulating RNA after induction or removal of senescent cells, animals were treated and serum was sampled 4 days after the last treatment as outlined in the experiment overview (FIG. 1A).

For expression analysis, the overall microRNA read counts (sum of all isomiRs) were normalized to total mapped reads per library ("tags per million, TPM"). We identified 179 miRNAs with one or more TPMs in each of the 13 samples, 94 of which were present at least with 10 TPM in each of the 13 samples. These 94 miRNAs were included in further analyses.

2.2. Circulating miRNAs Differentiate Between the Groups

For exploratory data analysis we applied principal component analysis (PCA) to the dataset of 50 most variable microRNAs according to the coefficient of variation. The PCA plot clearly indicates an effect of doxycycline (dox) treatment on circulating microRNA levels in p16-3MR mice compared to the PBS treated control animals (FIG. 2). This indicates that circulating miRNA levels are significantly changed upon the induction of senescence using doxycycline treatment. Analysis of differentially circulating miRNAs was focused on changes between dox treated versus control (PBS) to identify those miRNAs that are modulated by induction of senescence, as well as dox-GCV vs dox, in order to identify miRNAs that change after removal of senescent cells. A p-value threshold of <0.05 without correction for multiple testing was used. Thereby, we identified 10 significantly regulated miRNAs for dox versus control (Table 17) and 3 for dox-GCV versus Dox (Table 18), with one miRNA, miR-34a-5p as an overlap as visualized by a Venn diagram (FIGS. 3A and B). Serum levels of each single differentially expressed miRNA are shown in FIG. 4 as tags per million. Interestingly, ganciclovir treatment (GCV) resulted in a consistent decrease of serum miRNAs compared to PBS treated animals. GCV-treated animals are supposed to have a reduced number of senescent cells compared to PBS due to forced apoptosis. In case of miR-34a-5p, miR-27a-3p and miR-345-3p, levels in dox-treated animals are higher compared to PBS controls, but are decreased after rescue with dox+GCV.

The results are shown in FIG. 2, Principal component analysis. 50 microRNAs with the highest variation across all 13 samples were used for the analysis. The first two principal components explain 66.7% of the variation.

TABLE 16

Differentially secreted microRNAs after treatment with senescence-activating agents (dox vs pbs)

| microRNA ID | log fold change | p-value | FDR | avg TPM dox | avg TPM PBS |
|---|---|---|---|---|---|
| mmu-let-7f-5p | −1.29 | 0.004 | 0.406 | 178.25 | 506.00 |
| mmu-miR-143-3p | −1.57 | 0.005 | 0.406 | 393.00 | 1439.00 |
| mmu-miR-27a-3p | 1.08 | 0.008 | 0.406 | 16.50 | 9.00 |
| mmu-miR-144-5p | −1.06 | 0.008 | 0.406 | 34.50 | 86.00 |
| mmu-miR-34a-5p | 1.13 | 0.011 | 0.406 | 8.00 | 4.00 |
| mmu-miR-200a-3p | −1.11 | 0.013 | 0.406 | 25.25 | 69.00 |
| mmu-miR-98-5p | −1.06 | 0.014 | 0.406 | 132.00 | 319.33 |
| mmu-let-7a-5p | −1.01 | 0.015 | 0.406 | 379.25 | 894.33 |
| mmu-miR-194-5p | −1.24 | 0.018 | 0.406 | 3.50 | 11.00 |
| mmu-miR-215-3p | −1.14 | 0.024 | 0.500 | 18.50 | 49.33 |

TABLE 17

Differentially secreted microRNAs after rescue of senescence-activating agents (dox + gcv vs gcv)

| microRNA ID | log fold change | p-value | FDR | avg TPM dox + GCV | avg TPM GCV |
|---|---|---|---|---|---|
| mmu-miR-34a-5p | −1.34 | 0.005 | 0.481 | 2.33 | 8.00 |
| mmu-miR-206-3p | −2.38 | 0.006 | 0.481 | 9.00 | 73.75 |
| mmu-miR-345-3p | −1.10 | 0.037 | 1.000 | 2.33 | 7.50 |

These data suggest that circulating levels of these 12 miRNAs can be considered as a signature of senescent cell killing.

In order to extend these finding to potential additional miRNAs, we performed Pearson correlation to miR-34a-5p and miR-27a-3p, resulting in additional potential biomarkers (Table 18).

TABLE 18 microRNAs with high Pearson Correlation (>0.7) to miR-34a-5p and miR-27a

| Biomarker Candidate | Pearson Correlcation coefficient | |
|---|---|---|
| | miR-27a-3p | miR44a-5p |
| mmu-miR-10a-3p | 0.90 | 0.52 |
| mmu-miR-151-5p | 0.37 | 0.73 |
| mmu-miR-191-5p | 0.81 | 0.32 |
| mmu-miR-223-3p | 0.83 | 0.55 |
| mmu-miR-23a-3p | 0.63 | 0.65 |
| mmu-miR-243p | 0.89 | 0.61 |
| mmu-miR-29a-3p | 0.74 | 0.74 |
| mmu-miR-3058-3p | 0.54 | 0.80 |
| mmu-miR-30b-5p | 0.65 | 0.70 |
| mmu-miR-339-5p | 0.87 | 0.64 |
| mmu-miR-423-3p | 0.86 | 0.59 |
| mmu-miR-6395 | 0.81 | 0.61 |
| mmu-miR-652-3p | 0.66 | 0.77 |
| mmu-miR-671-3p | 0.60 | 0.71 |
| mmu-miR-93-3p | 0.69 | 0.78 |

Discussion

Here we describe circulating miRNAs that react to an increase of senescent cells in a mouse model, and to a decrease of senescent cells, identified as by NGS. Circulating miRNAs have recently gained attention as biomarkers, as they are protected from RNAses present in serum and plasma by either being packaged into EVs or by being protected by proteins or lipoprotein particles and thus can stably be detected in biofluids even after decades of blood sampling and storage at −80° C. (Hackl et al. 2015). Due to the small amounts of mouse serum samples, we here isolated total RNA from cell-free blood, and thus cannot differentiate between vesicle packaged or protein bound miRNAs. However, several miRNAs clearly show differential levels after induction or removal of senescent cells in vivo. We observed that the majority of microRNAs decreased after the exposure to a senescence-inducing agent except miR-27a-3p and miR-34a-5p, which were found to be increased. Accordingly, after removing senescent cells, a significant decline in the levels of miR-34a in mouse serum was observed, which suggests that there is a link between the serum levels of miR-34a-5p and systemic cellular senescence.

This miRNA has been the first to be identified as upregulated in cellular senescence by p53 induction and to be sufficient to also induce a senescence-like growth arrest in human fibroblasts (Tazawa et al. 2007), (He et al. 2007), (Maes et al. 2009), endothelial cells (Ito et al. 2010), and renal proximal tubular epithelial cells (Hackl et al. 2010). It is also upregulated during mouse kidney aging (Bai et al. 2011), as well as in bone marrow derived mesenchymal stem cells and skin derived from elderly versus young donors (Hackl et al. 2010). It modulates apoptotic behaviour (Tarasov et al. 2007), (Yamakuchi et al. 2008), also independently of p53 (Christoffersen et al. 2009). In line with its function within the p53 regulatory network, it is differentially expressed in many cancer cell types and functionally involved in regulating cancer cell proliferation, chemoresistance or apoptosis. Finally, since several types of cancer have been identified to lack miR-34, it has been used to induce apoptosis in tumors in mouse models (Xue et al. 2014), and by now has even reached clinical phase I trials against solid tumors (Adams et al. 2016).

In the context of aging, miR-34 family members were found to be increased in the circulation in age associated diseases including type 2 diabetes (Kong et al. 2011), hearing loss (Pang et al. 2016), non-alcoholic fatty liver disease (Salvoza et al. 2016), (Yamada et al. 2013), (Cermelli et al. 2011), Alzheimer's disease (Bhatnagar et al. 2014) and patients with coronary heart disease (Han et al. 2015) or during left ventricular remodelling after myocard infarction (Lv et al. 2014). In this context, it seems functionally involved in promoting cardiomyocyte apoptosis (Fan et al. 2013). It is also elevated in obesity, where it has been found to act on the FGF21 and klotho axis (Fu and Kemper 2016) and is also classified as an inflammamiR (Rippo et al. 2014), (de Gonzalo-Calvo et al. 2015). Interestingly, nutritional supplementation of T2D with grape wine extract and resveratrol decreases miR-34a levels in the serum (Tome-Carneiro et al. 2013). High tissue levels of miR-34a-5p in osteoarthritis might contribute to loss of chondrocytes at least in a rat model (Grillari and Grillari-Voglauer 2010), (Abouheif et al. 2010), while osteoporosis is diminished in miR-34 overexpressing transgenic mice (Krzeszinski et al. 2014). Additionally, in a model of kidney fibrosis, renal fibroblasts secrete miR-34a-5p (Zhou et al. 2014) in vitro, and we also find members of the miR-34 family to be secreted by senescent human skin fibroblasts (our unpublished results).

Chronic HIV infection and highly active anti-retroviral therapies (HAART) has recently been postulated to bear some resemblance to premature aging (Gustafson et al. 2016) and indeed, miR-34-5p has been observed to increase in patients with a decrease in T cell numbers (Reynoso et al. 2014).

In all of these conditions, an increase of senescent cells has been observed in the respective tissues as reviewed recently (Muñoz-Espín and Serrano 2014). Therefore, an increase of miR-34 family members, especially of miR-34a-5p might well be caused by an increase of senescent cells in vivo, which are in consequence secreting miR-34a-5p to the tissue microenvironment and the circulation. It is likely that thereby miR-34a-5p is packaged into extracellular vesicles, as it has been found in EVs in several studies (Corcoran et al. 2014).

MiR-27a-3p is also a promising marker in the circulation, as it is also upregulated intracellularly in senescent endothelial cells (Dellago et al. 2013) as well as in replicative aging of T cells (Hackl et al. 2010).

The miRNAs here identified do not seem not be derived from chronological T cell aging, as we did not observe miR-34-5p or the other miRNAs detected here in T cells from healthy elderly versus young individuals, in addition, they have not been found in signatures of aging in serum (Noren Hooten et al. 2013), nor in B cells (Gombar et al. 2012) or mononuclear cells (Serna et al. 2012).

Finally, the induction of senescence in our mouse model is based on doxorubicin, one of several chemotherapeutics shown to induce senescence in vitro and in vivo, and indeed, especially miR-34 family members are induced upon various chemotherapeutics including cisplatin, pemetrexed (Franchina et al. 2014) or neoadjuvant therapies in vivo and by doxorubicin in vitro.

Taken together, we propose the here identified serum based miRNAs to act as biomarkers for the presence of senescent cells as well as for their removal. This will be of specific value as a companion diagnostic in the development of senolytics.

Example 2

1. Materials and Methods
1.1. Mouse Work and Serum Sampling p16-3MR (Demaria et al, 2014, Developmental Cell 31:722-733) mice were bred in house and maintained in the AALAC-accredited Buck Institute for Research on Aging (Novato, Calif.) animal facility. 10 to 12-week-old p16-3MR male mice were used for experiments. Mice were divided in 4 groups and each group consisted of 8 animals, 5 female, and 3 male, respectively. In group A, control mice were injected with PBS. In group B, mice were treated with Ganciclovir (GCV) (Sigma-Aldrich) dissolved in PBS for 5 consecutive days. In group C, mice were treated with one dose of Doxorubicine hydrochloride (Sigma-Aldrich) dissolved in PBS. In group D, mice were first treated with Doxorubicine and then treated 10 days later with GCV. Mice were intraperitoneally injected with one dose of 10 mg/kg of Doxorubicine hydrochloride, and GCV was administered daily by intraperitoneal injections for 5 consecutive days at concentration of 25 mg/kg in PBS. 4 days after the last GCV dose, animals were euthanized with $CO_2$ and blood was withdrawn immediately. Blood was then incubated for 30 min at room temperature and centrifuged at 3400×g for 10 min. Serum was carefully collected in a sterile tube without disturbing the cell pellet and stored at −80° C. for further experiments.

1.2. RT-qPCR Analysis

Total RNA extraction was performed from 200 μl of serum using the Qiagen miRNeasy extraction kit (Qiagen, Germany). RNA yield was quality checked for homogenous extraction efficiency and hemolysis on the basis qPCR amplification of spiked-in as well as hemolysis-responsive RNAs (Blondal et al). In total 2 μl total RNA were used for reverse transcription using the Exiqon Universal RT kit II (Exiqon, Denmark). The obtained cDNA samples were pre-diluted 1:40 and subsequently mixed with SYBR Green® Mix (Exiqon, Denmark) to achieve a 1:100 dilution. The mix was distributed to primer-coated 384-well plates containing dried primer pairs for 96 selected microRNA or quality control assays. QPCR amplification was performed on a Roche LightCycler 480 II, using the manufacturer's recommendation for annealing, extension and denaturation.

1.3. Bioinformatics

Raw Cq-values were computed using the $2^{nd}$ derivative method. Melting curves were checked for peaks to ensure specificity of the amplification reactions. Cq-values were subsequently normalized using Spike-In controls as references, to reduce technical noise in the data.

Statistical analysis was performed using Medcalc (version 18.2.1). Normal distribution was assessed using D'Agostino-Pearson test, where normality was accepted at p>0.05. One-way ANOVA together together with Student-Newman-Keuls test for all pairwise comparisons (post-hoc tests) was used to identify significant changes between groups (p<0.05). To assess the discriminatory power of individual microRNAs, receiver operating characteristic (ROC) analysis was applied. ROC curves were plotted using sensitivity (y-axis) and 1-specificity (x-axis) and the area under the ROC curve (AUC) was calculated. MicroRNAs with AUC-values of >0.7 were considered as good discriminators/biomarkers. MicroRNAs with AUC-values >0.8 were considered very good discriminators/biomarkers.

2. Results 2.1. RT-qPCR Verification of Serum Circulating microRNA Changes Following the Induction of Senescence and Senolytic Treatment.

Using the above described statistical analyses, we demonstrate that the following microRNAs are indeed significantly regulated in serum of animals exposed to senescence-inducing agents (DOX) compared to negative control (PBS), independent of gender: let-7a, let-7b, miR-34a-5p, miR-34a-3p, miR-151-5p, miR-155-5p, miR-199a-5p, miR-199b-5p and miR-345-5p were found to be significantly (up- or down-regulated) in serum of animals after exposure to DOX (Table 23).

Vice-versa, the analysis of serum samples from female and male mice following the inactivation of senescence via GCV-treatment (DOX/GCV), and compared to stressed control animals (DOX), confirmed up- or down-regulation of the following microRNA biomarkers (p<0.05): serum levels of miR-23a-3p, miR-23b-3p, miR-24-3p, miR-27a-3p, and miR-146a-5p, miR-423-3p, miR-181b-5p, miR-183-3p, miR-215-5p, miR-31-5p, miR-375-5p, miR-409-3p, miR-125a-5p, miR-483-5p, and miR-150-5p were found to significantly changed (up- or down-regulated) following senolytic treatment.

FIG. 5A depicts the serum levels of confirmed microRNAs (let-7a-5p, let-7b-5p, miR-34a-5p, miR-34a-3p, miR-151-5p, miR-155-5p, miR-23a-3p, miR-23b-3p, miR-24-3p, miR-27a-3p, miR-146a-5p, miR-423-3p) across all 4 groups. FIG. 5B depicts the serum levels of microRNAs miR-199a-5p, miR-199b-5p, miR-345-5p, miR-181b-5p, miR-183-5p, miR-215-5p, miR-31-5p, miR-375-3p, miR-409-3p, miR-125a-5p, miR-483-5p, miR-150-5p across all 4 groups.

2.2. ROC Analysis to Assess Discriminatory Power of Circulating microRNAs for Diagnosis of Senescence and Senolytic Treatment.

In order to assess the diagnostic power of circulating microRNAs for the exposure with senescence inducing substances (DOX) as well as the efficacy of senolytic treatment, ROC analysis was performed and the area-under-the-curve (AUC) was calculated. Commonly, a biomarker with an AUC value >0.8 is considered to exhibit very good diagnostic performance, while a biomarker with an AUC >0.7 is considered to have good diagnostic performance. Table 23 below summarizes AUC values as well as 95% confidence intervals for 24 selected circulating microRNAs.

TABLE 23

| | | One-way ANOVA | | ROC Analysis | | | |
|---|---|---|---|---|---|---|---|
| | | Senescence | Senolytic | | | | |
| # | MicroRNA | (DOX vs PBS) | Treatment (DOX/GCV) | AUC Senescence | 95% CI | AUC Senolytic Treatment | 95% CI |
| 1 | let-7a-5p | * | + | 0.922* | 0.676 to 0.996 | 0.781* | 0.509 to 0.944 |
| 2 | let-7b-5p | * | * | 0.883* | 0.626 to 0.987 | 0.789* | 0.518 to 0.948 |
| 3 | miR-34a-5p | * | ○ | 1.000* | 0.794 to 1.000 | 0.672° | 0.398 to 0.880 |
| 4 | miR-34a-3p | * | ○ | 0.953* | 0.720 to 1.000 | 0.5° | 0.247 to 0.753 |
| 5 | miR-151-5p | * | ○ | 0.828* | 0.561 to 0.967 | 0.609° | 0.340 to 0.837 |
| 6 | miR-155-5p | * | ○ | 0.781* | 0.509 to 0.944 | 0.508° | 0.253 to 0.760 |
| 7 | miR-199a-5p | * | + | 0.906* | 0.656 to 0.993 | 0.781* | 0.509 to 0.944 |
| 8 | miR-199b-5p | * | + | 0.750+ | 0.476 to 0.927 | 0.734+ | 0.460 to 0.918 |
| 9 | miR-345-5p | * | * | 0.781* | 0.509 to 0.944 | 0.875* | 0.617 to 0.984 |
| 10 | miR-23a-3p | ○ | * | 0.516° | 0.259 to 0.766 | 0.844* | 0.579 to 0.973 |
| 11 | miR-23b-3p | ○ | * | 0.563° | 0.299 to 0.802 | 0.875* | 0.617 to 0.984 |
| 12 | miR-24-3p | ○ | * | 0.609° | 0.340 to 0.837 | 0.789* | 0.518 to 0.948 |
| 13 | miR-27a-3p | ○ | * | 0.664° | 0.391 to 0.875 | 0.719+ | 0.444 to 0.909 |
| 14 | miR-146a-5p | ○ | * | 0.531° | 0.272 to 0.778 | 0.742+ | 0.468 to 0.923 |
| 15 | miR-423-3p | + | * | 0.758+ | 0.484 to 0.932 | 0.828* | 0.561 to 0.967 |
| 16 | miR-181b-5p | + | + | 0.680+ | 0.406 to 0.885 | 0.75+ | 0.476 to 0.927 |
| 17 | miR-183-3p | ○ | * | 0.563° | 0.299 to 0.802 | 0.891* | 0.636 to 0.989 |
| 18 | miR-215-5p | ○ | * | 0.531° | 0.272 to 0.778 | 0.922* | 0.676 to 0.996 |
| 19 | miR-31-5p | + | ○ | 0.688+ | 0.413 to 0.890 | 0.672° | 0.398 to 0.880 |
| 20 | miR-375-5p | ○ | * | 0.570° | 0.306 to 0.808 | 0.859* | 0.598 to 0.979 |
| 21 | miR-409-3p | ○ | * | 0.609° | 0.340 to 0.837 | 0.859* | 0.598 to 0.979 |
| 22 | miR-125a-5p | + | * | 0.742+ | 0.468 to 0.923 | 0.789* | 0.518 to 0.948 |
| 23 | miR-483-5p | ○ | * | 0.563° | 0.299 to 0.802 | 0.766* | 0.493 to 0.936 |
| 24 | miR-150-5p | ○ | + | 0.602° | 0.333 to 0.831 | 0.734+ | 0.460   0.918 |

*significant p < 0.05
+by trend p < 0.2
°no trend 2.3. Combinations of specific microRNAs show increased diagnostic performance compared to individual microRNAs or unrelated microRNAs We performed multiple logistic regression analysis and ROC analysis to compare the performance of combinations of encompassed microRNA against that of individual encompassed microRNAs (Table 23) as well as combinations of microRNAs that are unrelated to senescence-associated microRNAs ("unrelated microRNAs").

FIG. 6A clearly shows the difference in diagnostic performance of microRNAs encompassed in Table 23 (let-7a-5p, miR-125a-5p, miR-199a-5p, miR-345-5p, miR-423-3p) to that of unrelated microRNAs (miR-221-3p, miR-222-3p, miR-22-3p, miR-378a-3p, miR-582-5p) for diagnosis of senescence: AUC of 0.953 compared to AUC of 0.719 (p=0.1).

FIG. 6B clearly shows the difference in diagnostic performance of the same encompassed microRNAs (let-7a-5p, miR-125a-5p, miR-199a-5p, miR-345-5p, miR-423-3p) to that of unrelated microRNAs (miR-221-3p, miR-222-3p, miR-22-3p, miR-378a-3p, miR-582-5p) for the effectiveness of senolytic treatment: AUC of 0.938 compared to AUC of 0.578 (p=0.015).

The AUC-values of a specific microRNA combination for diagnosis of cellular senescence as well as monitoring of senolytic treatment (both AUC >0.9) are clearly superior to the individual performance of microRNAs, since no individual microRNA reaches an AUC >0.9 for both diagnosis of cellular senescent and senolytic treatment monitoring (Table 23).

3. Discussion

Analytical technologies for the detection and quantification of circulating microRNAs have inherent biases, which can ultimately result in the selection of false-positive or false-negative biomarker candidates. To avoid this pitfall, we have applied RT-qPCR analysis to an extended set of male and female animals that were derived the same four groups as in the original NGS-based discovery study, to assess the comparability of the results and hence increase confidence in our findings.

Our analysis shows that 24 microRNAs are significantly regulated in senescent cells and in cells following senolytic treatment. Specifically let-7a, let-7b, miR-34a-5p, miR-34a-3p, miR-151-5p, miR-155-5p, miR-199a-5p, miR-199b-5p and miR-345-5p were found to be significantly up- or down-regulated in serum of animals after exposure to senescence inducing compounds.

Vice-versa, inactivation of senescence, i.e as a result of senolytic treatment, resulted in significant up- or downregulation of miR-23a-3p, miR-23b-3p, miR-24-3p, miR-27a-3p, and miR-146a-5p, miR-423-3p, miR-181b-5p, miR-183-3p, miR-215-5p, miR-31-5p, miR-375-5p, miR-409-3p, miR-125a-5p, miR-483-5p, and miR-150-5p We also found several microRNAs that show significant regulation (p<0.05), or at least a trend for regulation (p<0.20) in both states, senescence and senolytic treatment, respectively. Therefore, these microRNAs are considered very good discriminators of senescence (AUC>0.8): let-7a-5p, let-7b-5p, miR-199a-5p, miR-345-5p, miR-423-3p, miR-125a-5p.

Finally, we demonstrate that the combination of these microRNAs in the form of a multiple regression model yields a score, which is highly sensitive and specific for the presence of senescent cells (FIG. 6A) as well as efficacy of senolytic therapy (FIG. 6B), and outperforms individual encompassed microRNAs as well as combinations of unrelated microRNAs.

CITED REFERENCES

Abouheif M M, Nakasa T, Shibuya H, Niimoto T, Kongcharoensombat W & Ochi M (2010) Silencing microRNA-34a inhibits chondrocyte apoptosis in a rat osteoarthritis model in vitro. Rheumatology (Oxford). 49, 2054-60.

Adams B D, Parsons C & Slack FJ (2016) The tumor-suppressive and potential therapeutic functions of miR-34a in epithelial carcinomas. Expert Opin. Ther. Targets 20, 737-53.

Bai X Y, Ma Y, Ding R, Fu B, Shi S & Chen X M (2011) miR-335 and miR-34a Promote renal senescence by suppressing mitochondrial antioxidative enzymes. J Am Soc Nephrol 22, 1252-1261.

Baar M P, Brandt R M, Putavet D A, Klein J D, Derks K W, Bourgeois B R, Stryeck S, Rijksen Y, van Willigenburg H, Feijtel D A, van der Pluijm I, Essers J, van Cappellen W A, van Ikken W F, Houtsmuller A B, Pothof J, de Bruin R W, Madl T, Hoeijmakers J H, Campisi J, de Keizer P L (2017) Targeted Apoptosis of Senescent Cells Restores Tissue Homeostasis in Response to Chemotoxicity and Aging. Cell 169(1), 132-147 Behjati S and Tarpey P (2013) What is next generation sequencing? Arch.Di-.Child Educ Pract Ed. 98, 236-238.

Baker D J, Childs B G, Durik M, Wijers M E, Sieben C J, Zhong J, A. Saltness R, Jeganathan K B, Verzosa G C, Pezeshki A, Khazaie K, Miller J D & van Deursen J M (2016) Naturally occurring p16Ink4a-positive cells shorten healthy lifespan. Nature 530, 184-189.

Baker D J, Wijshake T, Tchkonia T, LeBrasseur N K, Childs B G, van de Sluis B, Kirkland J L & van Deursen J M (2011) Clearance of p16Ink4a-positive senescent cells delays ageing-associated disorders. Nature 479, 232-236.

Demaria M, Ohtani N, Youssef S A, Rodier F, Toussaint W, Mitchell J R, Laberge R M, Vijg J, van Steeg H, Dolle M E, Hoeijmakers J H, de Bruin A, Hara E, Campisi J. 2014. An essential role for senescent cells in optimal wound healing through secretion of PDGF-AA. Dev Cell 31:722-733.

Beyer C, Zampetaki A, Lin N-Y, Kleyer A, Perricone C, lagnocco A, Distler A, Langley S R, Gelse K, Sesselmann S, Lorenzini R, Niemeier A, Swoboda B, Distler J H W, Santer P, Egger G, Willeit J, Mayr M, Schett G & Kiechl S (2015) Signature of circulating microRNAs in osteoarthritis. Ann. Rheum. Dis. 74, e18.

Bhatnagar S, Chertkow H, Schipper H M, Yuan Z, Shetty V, Jenkins S, Jones T & Wang E (2014) Increased microRNA-34c abundance in Alzheimer's disease circulating blood plasma. Front. Mol. Neurosci. 7, 2.

Blondal T, Jensby Nielsen S, Baker A, Andreasen D, Mouritzen P, Wrang Teilum M & Dahlsveen I K (2013) Assessing sample and miRNA profile quality in serum and plasma or other biofluids. Methods 59, S1-6.

Boeckel J N, Thomé C E, Leistner D, Zeiher A M, Fichtlscherer S, Dimmeler S., Heparin selectively affects the quantification of microRNAs in human blood samples, Clin Chem. 2013 July; 59(7):1125-7. doi: 10.1373/clinchem.2012.199505. Epub 2013 Apr. 23

Cermelli S, Ruggieri A, Marrero J A, loannou G N & Beretta L (2011) Circulating microRNAs in patients with chronic hepatitis C and non-alcoholic fatty liver disease. PLoS One 6, e23937.

Chang J, Wang Y, Shao L, Laberge R M, Demaria M, Campisi J, Janakiraman K, Sharpless N E, Ding S, Feng W, Luo Y, Wang X, Aykin-Burns N, Krager K, Ponnappan U, Hauer-Jensen M, Meng A & Zhou D (2016) Clearance of senescent cells by ABT263 rejuvenates aged hematopoietic stem cells in mice. Nat Med 22, 78-83. Available at: www.ncbi.nlm.nih.gov/pubmed/26657143.

Chen X, Ba Y, Ma L, Cai X, Yin Y, Wang K, Guo J, Zhang Y, Chen J, Guo X, Li Q, Li X, Wang W, Zhang Y, Wang J, Jiang X, Xiang Y, Xu C, Zheng P, Zhang J, Li R, Zhang H, Shang X, Gong T, Ning G, Wang J, Zen K, Zhang J, Zhang CY. Characterization of microRNAs in serum: a novel class of biomarkers for diagnosis of cancer and other diseases. Cell Res. 2008 October; 18(10):997-1006. doi: 10.1038/cr.2008.282.

Cheng H H, Yi H S, Kim Y, Kroh E M, Chien J W, Eaton K D, Goodman M T, Tait J F, Tewari M, Pritchard C C. Plasma processing conditions substantially influence circulating microRNA biomarker levels. PLoS One. 2013 Jun. 7; 8(6):e64795. doi: 10.1371/journal.pone.0064795. Print 2013. PMID:23762257.Christoffersen NR, Shalgi R, Frankel LB, Leucci E, Lees M, Klausen M, Pilpel Y, Nielsen FC, Oren M & Lund AH (2009) p53-independent upregulation of miR-34a during oncogene-induced senescence represses MYC. Cell Death Differ.

Corcoran C, Rani S & O'Driscoll L (2014) miR-34a is an intracellular and exosomal predictive biomarker for response to docetaxel with clinical relevance to prostate cancer progression. Prostate 74, 1320-34.

Dellago H, Preschitz-Kammerhofer B, Terlecki-Zaniewicz L, Schreiner C, Fortschegger K, Chang M W, Hackl M, Monteforte R, Kuhnel H, Schosserer M, Gruber F, Tschachler E, Scheideler M, Grillari-Voglauer R, Grillari J & Wieser M (2013) High levels of oncomiR-21 contribute to the senescence induced growth arrest in normal human cells and its knock-down increases the replicative life span. Aging Cell.

Demaria M, Ohtani N, Youssef S A, Rodier F, Toussaint W, Mitchell J R, Laberge R M, Vijg J, van Steeg H, Dolle M E, Hoeijmakers J H, de Bruin A, Hara E, Campisi J. 2014. An essential role for senescent cells in optimal wound healing through secretion of PDGF-AA. Dev Cell 31:722-733.

Fan F, Sun A, Zhao H, Liu X, Zhang W, Jin X, Wang C, Ma X, Shen C, Zou Y, Hu K & Ge J (2013) MicroRNA-34a promotes cardiomyocyte apoptosis post myocardial infarction through down-regulating aldehyde dehydrogenase 2. Curr. Pharm. Des. 19, 4865-73.

Franchina T, Amodeo V, Bronte G, Savio G, Ricciardi G R R, Picciotto M, Russo A, Giordano A & Adamo V (2014) Circulating miR-22, miR-24 and miR-34a as novel predictive biomarkers to pemetrexed-based chemotherapy in advanced non-small cell lung cancer. J. Cell. Physiol. 229, 97-9.

Fu T & Kemper J K (2016) MicroRNA-34a and Impaired FGF19/21 Signaling in Obesity. Vitam. Horm. 101, 175-96.

Gombar S, Jung H, Dong F, Calder B, Atzmon G, Barzilai N, Tian X-L, Pothof J, Hoeijmakers J H, Campisi J, Vijg J & Suh Y (2012) Comprehensive microRNA profiling in B-cells of human centenarians by massively parallel sequencing. BMC Genomics 13, 353.

de Gonzalo-Calvo D, Dávalos A, Montero A, García-González Á, Tyshkovska I, González-Medina A, Soares S M A, Martínez-Camblor P, Casas-Agustench P, Rabadán M, Díaz-Martínez Á E, Úbeda N & Iglesias-Gutiérrez E (2015) Circulating inflammatory miRNA signature in response to different doses of aerobic exercise. J. Appl. Physiol. 119, 124-34.

Garcia M E, Blanco J L, Caballero J, Gargallo-Viola D. Anticoagulants interfere with PCR used to diagnose invasive aspergillosis. J Clin Microbiol. 2002 April; 40(4): 1567-8. No abstract available. PMID: 11923400

Grillari J & Grillari-Voglauer R (2010) Novel modulators of senescence, aging, and longevity: Small non-coding RNAs enter the stage. Exp Gerontol 45, 302-311.

Gustafson D R, Shi Q, Thurn M, Holman S, Minkoff H, Cohen M, Plankey M W, Havlik R, Sharma A, Gange S, Gandhi M, Milam J & Hoover D (2016) Frailty and Constellations of Factors in Aging HIV-infected and Uninfected Women—The Women's Interagency HIV Study. J. frailty aging 5, 43-8.

Hackl M, Brunner S, Fortschegger K, Schreiner C, Micutkova L, Muck C, Laschober G T, Lepperdinger G, Sampson N, Berger P, Herndler-Brandstetter D, Wieser M, Kuhnel H, Strasser A, Rinnerthaler M, Breitenbach M, Mildner M, Eckhart L, Tschachler E, Trost A, Bauer J W, Papak C, Trajanoski Z, Scheideler M, Grillari-Voglauer R, Grubeck-Loebenstein B, Jansen-Durr P, Grillari J, Mück C, Kühnel H & Jansen-Dürr P (2010) miR-17, miR-19b, miR-20a and miR-106a are down-regulated in human aging. Aging Cell 9, 291-296.

Hackl M, Heilmeier U, Weilner S & Grillari J (2015) Circulating microRNAs as novel biomarkers for bone diseases—Complex signatures for multifactorial diseases? Mol. Cell. Endocrinol.

Han H, Qu G, Han C, Wang Y, Sun T, Li F, Wang J & Luo S (2015) MiR-34a, miR-21 and miR-23a as potential biomarkers for coronary artery disease: a pilot microarray study and confirmation in a 32 patient cohort. Exp. Mol. Med. 47, e138.

He X, He L & Hannon G J (2007) The guardian's little helper: microRNAs in the p53 tumor suppressor network. Cancer Res 67, 11099-11101.Head S. R., H., Komori K., LaMere S. A., Whisenant, T., Van Nieuwerburgh, Salomon, D. R., and Ordoukhanian P., Library construction for next-generation sequencing: Overviews and challenges, Biotechniques. Author manuscript; available in PMC 2015 March Ito T, Yagi S & Yamakuchi M (2010) MicroRNA-34a regulation of endothelial senescence. Biochem Biophys Res Commun 398, 735-740.

Kim D J, Linnstaedt S, Palma J, Park J C, Ntrivalas E, Kwak-Kim J Y, Gilman-Sachs A, Beaman K, Hastings M L, Martin J N, Duelli D M. Plasma components affect accuracy of circulating cancer-related microRNA quantitation. J Mol Diagn. 2012 January; 14(1):71-80. doi: 10.1016/j.jmoldx.2011.09.002. Epub 2011 Nov. 30. PMID: 22154918

Kong L, Zhu J, Han W, Jiang X, Xu M, Zhao Y, Dong Q, Pang Z, Guan Q, Gao L, Zhao J & Zhao L (2011) Significance of serum microRNAs in pre-diabetes and newly diagnosed type 2 diabetes: a clinical study. Acta Diabetol. 48, 61-9.

Krzeszinski J Y, Wei W, Huynh H, Jin Z, Wang X, Chang T-C, Xie X-J, He L, Mangala L S, Lopez-Berestein G, Sood A K, Mendell J T & Wan Y (2014) miR-34a blocks osteoporosis and bone metastasis by inhibiting osteoclastogenesis and Tgif2. Nature 512, 431-5.

Lv P, Zhou M, He J, Meng W, Ma X, Dong S, Meng X, Zhao X, Wang X & He F (2014) Circulating miR-208b and miR-34a are associated with left ventricular remodeling after acute myocardial infarction. Int. J. Mol. Sci. 15, 5774-88.

Maes O C, Sarojini H & Wang E (2009) Stepwise upregulation of microRNA expression levels from replicating to reversible and irreversible growth arrest states in WI-38 human fibroblasts. J Cell Physiol 221, 109-119.

Matjusaitis M, Chin G, Sarnoski E A & Stolzing A (2016) Biomarkers to identify and isolate senescent cells. Ageing Res. Rev.

Metsalu T & Vilo J (2015) ClustVis: a web tool for visualizing clustering of multivariate data using Principal Component Analysis and heatmap. Nucleic Acids Res. 43, W566-70.

Mitchell P S, Parkin R K, Kroh E M, Fritz B R, Wyman S K, Pogosova-Agadjanyan E L, Peterson A, Noteboom J, O'Briant K C, Allen A, Lin D W, Urban N, Drescher C W, Knudsen B S, Stirewalt D L, Gentleman R, Vessella R L, Nelson P S, Martin DB & Tewari M (2008) Circulating microRNAs as stable blood-based markers for cancer detection. Proc Natl Acad Sci U S A 105, 10513-10518.

Metzker M L (2010) Sequencing technologies—the next generation. Nat Rev Genet 11(1), 31-46.

Muñoz-Espin D & Serrano M (2014) Cellular senescence: from physiology to pathology. Nat. Rev. Mol. Cell Biol. 15, 482-96.

Noren Hooten N, Fitzpatrick M, Wood W H, De S, Ejiogu N, Zhang Y, Mattison J a, Becker K G, Zonderman A B & Evans M K (2013) Age-related changes in microRNA levels in serum. Aging (Albany. NY). 5, 725-40.

Pang J, Xiong H, Yang H, Ou Y, Xu Y, Huang Q, Lai L, Chen S, Zhang Z, Cai Y & Zheng Y (2016) Circulating miR-34a levels correlate with age-related hearing loss in mice and humans. Exp. Gerontol. 76, 58-67.

Reynoso R, Laufer N, Hackl M, Skalicky S, Monteforte R, Turk G, Carobene M, Quarleri J, Cahn P, Werner R, Stoiber H, Grillari-Voglauer R & Grillari J (2014) MicroRNAs differentially present in the plasma of HIV elite controllers reduce HIV infection in vitro. Sci. Rep. 4,5915.

Rippo M R, Olivieri F, Monsurrò V, Prattichizzo F, Albertini M C & Procopio A D (2014) MitomiRs in human inflamm-aging: a hypothesis involving miR-181a, miR-34a and miR-146a. Exp. Gerontol. 56, 154-63.

Schraml E & Grillari J (2012) From cellular senescence to age-associated diseases: the miRNA connection. Longev. Heal. 1, 10.

Salvoza N C, Klinzing D C, Gopez-Cervantes J & Baclig M O (2016) Association of Circulating Serum miR-34a and miR-122 with Dyslipidemia among Patients with Non-Alcoholic Fatty Liver Disease. PLoS One 11, e0153497.

Serna E, Gambini J, Borras C, Abdelaziz K M, Mohammed K, Belenguer A, Sanchis P, Avellana J A, Rodriguez-Mañas L & Vina J (2012) Centenarians, but not octogenarians, up-regulate the expression of microRNAs. Sci. Rep. 2, 961.

Tarasov V, Jung P, Verdoodt B, Lodygin D, Epanchintsev A, Menssen A, Meister G & Hermeking H (2007) Differential regulation of microRNAs by p53 revealed by massively parallel sequencing: miR-34a is a p53 target that induces apoptosis and G1-arrest. Cell Cycle 6, 1586-1593.

Tazawa H, Tsuchiya N, Izumiya M & Nakagama H (2007) Tumor-suppressive miR-34a induces senescence-like growth arrest through modulation of the E2F pathway in human colon cancer cells. Proc Natl Acad Sci U S A 104, 15472-15477.

Tomé-Carneiro J, Larrosa M, Yáñez-Gascón M J, Dávalos A, Gil-Zamorano J, Gonzálvez M, García-Almagro F J, Ruiz Ros J A, Tomás-Barberán F A, Espín JC & García-Conesa M-T (2013) One-year supplementation with a grape extract containing resveratrol modulates inflammatory-related microRNAs and cytokines expression in peripheral blood mononuclear cells of type 2 diabetes and hypertensive patients with coronary artery disease. Pharmacol. Res. 72, 69-82.

Turchinovich A, Samatov T R, Tonevitsky A G & Burwinkel B (2013) Circulating miRNAs: cell-cell communication function? Front. Genet. 4, 1-10. Xue W, Dahlman J E, Tammela T, Khan O F, Sood S, Dave A, Cai W, Chirino L M, Yang GR, Bronson R, Crowley D G, Sahay G, Schroeder A, Langer R, Anderson D G & Jacks T (2014) Small RNA combination therapy for lung cancer. Proc. Natl. Acad. Sci. U.S.A. 111, E3553-61.

Yamada H, Suzuki K, Ichino N, Ando Y, Sawada A, Osakabe K, Sugimoto K, Ohashi K, Teradaira R, Inoue T, Hamajima N & Hashimoto S (2013) Associations between circulating microRNAs (miR-21, miR-34a, miR-122 and miR-451) and non-alcoholic fatty liver. Clin. Chim. Acta. 424, 99-103.

Yamakuchi M, Ferlito M & Lowenstein C J (2008) miR-34a repression of SIRT1 regulates apoptosis. Proc Natl Acad Sci U S A 105, 13421-13426.

Zampetaki A, Kiechl S, Drozdov I, Willeit P, Mayr U, Prokopi M, Mayr A, Weger S, Oberhollenzer F, Bonora E, Shah A, Willeit J & Mayr M (2010) Plasma microRNA profiling reveals loss of endothelial miR-126 and other microRNAs in type 2 diabetes. Circ Res 107, 810-817.

Zampetaki A, Willeit P, Tilling L, Drozdov I, Prokopi M, Renard J M, Mayr A, Weger S, Schett G, Shah A, Boulanger C M, Willeit J, Chowienczyk P J, Kiechl S & Mayr M (2012) Prospective Study on Circulating MicroRNAs and Risk of Myocardial Infarction. J Am Coll Cardiol 60, 290-299.

Zhou Y, Xiong M, Niu J, Sun Q, Su W, Zen K, Dai C & Yang J (2014) Secreted fibroblast-derived miR-34a induces tubular cell apoptosis in fibrotic kidney. J. Cell Sci. 127, 4494-4506.

Zhu Y, Tchkonia T, Fuhrmann-Stroissnigg H, Dai H M, Ling Y Y, Stout M B, Pirtskhalava T, Giorgadze N, Johnson K O, Giles C B, Wren J D, Niedernhofer L J, Robbins P D & Kirkland J L (2016) Identification of a novel senolytic agent, navitoclax, targeting the Bcl-2 family of anti-apoptotic factors. Aging Cell 15, 428-35.

Zhu Y, Tchkonia T, Pirtskhalava T, Gower A, Ding H, Giorgadze N, Palmer A K, Ikeno Y, Borden G, Lenburg M, O'Hara S P, LaRusso N F, Miller J D, Roos C M, Verzosa G C, LeBrasseur N K, Wren J D, Farr J N, Khosla S, Stout M B, McGowan S J, Fuhrmann-Stroissnigg H, Gurkar A U, Zhao J, Colangelo D, Dorronsoro A, Ling Y Y, Barghouthy A S, Navarro D C, Sano T, Robbins P D, Niedernhofer L J & Kirkland J L (2015) The Achilles' Heel of Senescent Cells: From Transcriptome to Senolytic Drugs. Aging Cell 14, n/a-n/a.

---

The invention claimed is:

1. A method of treating cellular senescence in a subject with senescent cells, comprising the sequential steps of:
   a) providing a first cell-free sample from said subject,
   b) quantifying levels of miRNAs in said sample, wherein the miRNAs are let-7a-5p, miR-199a-5p, miR-345-5p, miR-423-3p and miR-125a-5p,
   c) comparing the levels of b) with reference levels of said miRNAs in a reference sample to detect the presence of the senescent cells, and detecting a difference between the levels of b) and the levels of the reference sample, wherein the difference between the levels of b) and the levels of the reference sample is indicative of the presence of the senescent cells, and
   d) treating said subject with a senolytic agent or an anti-aging agent in order to treat the cellular senescence when a difference in miRNA levels which indicates the presence of the senescent cells in the subject is detected in step c).

2. The method of claim 1, wherein the level of 6, 7, 8, 9, 10, 11, 12, 13,14, 15, 16, 17, 18, 19, 20, 21, 22, 23, 24 or more miRNAs is quantified.

3. The method according to claim 1, wherein the reference levels are levels of the corresponding miRNAs in a sample of a healthy subject or of a subject participating in a pharmacologic, dietary or life-style intervention or of a group of subjects thereof.

4. The method according to claim 1, wherein a difference by more than one standard deviation between the levels of b) and the levels of the reference sample is indicative of the presence of the senescent cells.

5. The method according to claim 1, further comprising the steps of providing a second cell-free sample from said subject after treating said subject with the senolytic agent or anti-aging agent, quantifying levels of let-7a-5p, miR-199a-5p, miR-345-5p, miR-423-3p, and miR-125a-5p in said second cell-free sample, and comparing the levels in said second cell-free sample with levels of said miRNAs in the first cell-free sample from said subject in order to determine the subject's response to treatment, wherein a more than 1.5 fold difference between the quantified miRNA levels of the first cell-free sample and the quantified miRNA levels of the second cell-free sample is indicative of a response to the treatment.

6. The method of claim 1, wherein the miRNA levels are determined by quantitative or digital PCR, sequencing, microarray analysis, a nucleic acid assay, or other hybridization-based technique.

7. The method of claim 1, wherein the subject is at least 30, 40, 50, 60, 70, 80 or 90 years of age, and is a subject at risk of an age-associated disease and/or at risk of senescence-associated secretory phenotype (SASP).

8. The method of claim 1, wherein the sample is a blood sample.

9. The method of claim 1, further comprising the step of detecting a decline of senescent cells or reduction of cellular senescence, wherein the level of said miRNAs is compared with a level of corresponding miRNAs in a sample of the subject obtained prior to a treatment with the senolytic agent or the anti-aging agent.

10. The method of claim 1, wherein the senolytic agent is one or more of an HSP90 inhibitor, an inhibitor of a Bcl-2 anti-apoptotic factor, a murine double minute 2 (MDM2) inhibitor, a spiro-oxindole compound, a benzodiazepine compound, a piperidinone compound, a tryptamine compound, CGM097, a MDM2 or HDM2 inhibitor, a protein kinase B inhibitor, ganciclovir (GCV), AP20187, quercetin, dasatinib, or a FOXO4 inhibiting peptide.

11. The method of claim 10, wherein the senolytic agent is one or more of navitoclax, TW-37, a cis-imidazoline compound, uprosertib, afuresertib, MK-2206, or ipatasertib.

12. The method of claim 1, wherein the anti-aging agent is one or more of rapamycin, spermidine, or metformin.

* * * * *